United States Patent
Manley et al.

(10) Patent No.: US 10,238,670 B2
(45) Date of Patent: Mar. 26, 2019

(54) 9-AMINOMETHYL MINOCYCLINE COMPOUNDS AND METHODS OF USE THEREOF IN URINARY TRACT INFECTION (UTI) TREATMENT

(71) Applicant: Paratek Pharmaceuticals, Inc., Boston, MA (US)

(72) Inventors: Amy L. Manley, Phoenixville, PA (US); Evangelos L. Tzanis, Newtown Square, PA (US); Lynne Garrity-Ryan, Melrose, MA (US); S. Ken Tanaka, Bellevue, WA (US); Judith N. Steenbergen, Newtown, PA (US); Stephen Bai, Newark, DE (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 9 days.

(21) Appl. No.: 15/584,679

(22) Filed: May 2, 2017

(65) Prior Publication Data
US 2017/0333455 A1 Nov. 23, 2017

Related U.S. Application Data

(60) Provisional application No. 62/422,852, filed on Nov. 16, 2016, provisional application No. 62/415,988, filed on Nov. 1, 2016, provisional application No. 62/350,332, filed on Jun. 15, 2016, provisional application No. 62/330,436, filed on May 2, 2016.

(51) Int. Cl.
*A61K 9/00* (2006.01)
*A61K 9/20* (2006.01)
*A61K 31/65* (2006.01)

(52) U.S. Cl.
CPC ............ *A61K 31/65* (2013.01); *A61K 9/0019* (2013.01); *A61K 9/0053* (2013.01); *A61K 9/20* (2013.01)

(58) Field of Classification Search
CPC combination set(s) only.
See application file for complete search history.

(56) References Cited

U.S. PATENT DOCUMENTS

| | | | |
|---|---|---|---|
| 7,553,828 B2 * | 6/2009 | Nelson | C07D 317/66 514/152 |
| 2010/0113399 A1 | 5/2010 | Cvetovich et al. | |
| 2013/0109657 A1 | 5/2013 | Zhou et al. | |
| 2014/0255339 A1 | 9/2014 | Sommadossi et al. | |

OTHER PUBLICATIONS

Parak Pharmaceuticals, Form S-1 Registration Statement under the Securities Act of 1933, Publicly available on Aug. 10, 2013.*
Cristina d'Urso de Souza Mendes. Antibiotics 2013, 2(4), 500-534.*
Noel et al, Antimicrob. Agents Chemother. Nov. 2012 vol. 56 No. 11, pp. 5650-5654.*
Kattan, Cleveland Clinic, published Nov. 2013.*
Flamm et al, Poster C-614, Jan. 2015.*

* cited by examiner

*Primary Examiner* — Jean P Cornet
(74) *Attorney, Agent, or Firm* — McCarter & English, LLP; Jonathan M. Sparks; Yu Lu

(57) ABSTRACT

The invention disclosed herein provides a method for treating urinary tract infection (UTI) using 9-[(2,2-dimethyl-propyl amino)-methyl]-minocycline or a salt thereof, in either oral or IV doses or a combination of both.

22 Claims, 6 Drawing Sheets

9-AMINOMETHYL MINOCYCLINE COMPOUNDS AND METHODS OF USE THEREOF IN URINARY TRACT INFECTION (UTI) TREATMENT

REFERENCE TO RELATED APPLICATIONS

This application claims the benefit of the filing dates of U.S. Provisional Application No. 62/330,436, filed on May 2, 2016, to U.S. Provisional Application No. 62/350,332, filed on Jun. 15, 2016, U.S. Provisional Application No. 62/415,988, filed on Nov. 1, 2016, and U.S. Provisional Application No. 62/422,852, filed on Nov. 16, 2016, the entire contents of each of which are incorporated herein by reference.

BACKGROUND OF THE INVENTION

The development of the tetracycline antibiotics was the direct result of a systematic screening of soil specimens collected from many parts of the world for evidence of microorganisms capable of producing bactericidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of minocycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced minocycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsia; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., Pneumococci and Salmonella). The rise of tetracycline-resistant organisms has resulted in a general decline in use of tetracyclines and tetracycline analogue compositions as antibiotics of choice. In addition, other antibacterial agents have also been over used creating strains of multiple drug resistant bacteria. Therefore, there is a need for effective antibacterial agents for the treatment of bacterial infections in general, particularly antibacterial agents with no or less severe resistance by disease-responsible pathogens.

Urinary tract infections (UTIs) are bacterial infections of the urinary tract and are one of the most common conditions for which patients are prescribed antibiotics (Mazzulli, *The Canadian Journal of Urology* 19(s1):42-48, 2012). When it affects the lower urinary tract, it is known as a simple cystitis (a bladder infection). When it affects the upper urinary tract, it is known as pyelonephritis (a kidney infection). Symptoms from a lower urinary tract include painful urination and either frequent urination or urge to urinate (or both); while the symptoms of pyelonephritis include fever and flank pain in addition to the symptoms of a lower UTI. In some cases, a painful burning sensation in the urethra may be present even when not urinating.

UTIs are fairly common in the general population with nearly 50% of women (and 12% of men) having at least one UTI in their lifetime, making UTIs the most common bacterial infection in women. UTIs have a high recurrence rate with about 25% of women experiencing a second episode within 6 months of their first UTI (Foxman, *Disease-a-Month* 49(2):53-70, 2003). About 15% of all community-prescribed antibiotics in the US are dispensed for UTIs, which is estimated to total over $1 billion annually. Direct and indirect costs due to UTIs total $1.6 billion annually.

UTIs are categorized into uncomplicated and complicated UTIs (cUTI). Uncomplicated UTIs are usually diagnosed in healthy premenopausal women with normal functioning urinary tracts. cUTIs are found in patients with structural or functional abnormalities in their urinary tract who may possess other underlying risk factors such as antibiotic-resistant organisms, comorbid illnesses, or recurrent UTIs. In addition, if a urinary tract infection involves the upper tract, and the person has diabetes mellitus, is pregnant, is male, or immunocompromised, it is considered complicated. To diagnose either an uncomplicated or complicated UTI, a clinician must perform a history and a physical examination and send samples for urinalysis. Acute symptoms consist of urinary frequency, pain or burning on urination, urgency, or foul smelling or cloudy urine. More severe UTIs that involve the upper urinary tract can present additionally with patient discomfort, flank pain, and fever.

Although urine cultures are not always performed with uncomplicated UTIs, they are mandatory when a cUTI is suspected. The presence of certain biomarkers such as nitrites and leukocyte esterase in the urine are indicators of UTIs. If the infection is suspected to have spread to the kidneys, urine cultures are then recommended. Urine cultures are also recommended for patients whose symptoms do not resolve or recur 2-4 weeks after treatment. Computed tomography (CT) or ultrasound scans are usually performed to rule out correctable, anatomical causes of cUTIs. If UTIs are left untreated or are treated inadequately, patients can develop complications such as recurrent infections, renal failure, or sepsis (Nicolle, *The Canadian Journal of Infectious Disease and Medical Microbiology* 16(6):349-360, 2005).

There are approximately 7 million and 0.9 million uncomplicated and complicated UTI cases each year. Quality of life is affected and daily activity is interrupted, with the patient missing work or school due to UTIs.

The pathogen responsible for nearly all UTIs is uropathogenic *Escherichia coli* (UPEC), which is isolated in greater than 75% of cases. Complicated UTIs (cUTIs) have more varied, less predictable bacterial etiologies, although UPEC is still found in roughly 50% of cases. Pathogens responsible for cUTIs, including MRSA, methicillin-resistant coagulase-negative staphylococci (MRCoNS), vancomycin-resistant enterococci (VRE), and bacteria producing extended spectrum beta lactamases (ESBLs), tend to be more resistant to current antibiotic therapies (Pallett and Hand, *Journal of Antimicrobial Chemotherapy* 65(s3):iii25-33, 2010). The most common route of infection is for UPEC to enter the urethra and ascend into the bladder. After infection, UPEC migrate into deeper urothelial layers and proliferate intracellularly in clusters, eventually forming biofilms capable of defending against the body's immune response.

As to treatment, IDSA recommends co-trimoxazole twice daily for three days as the first line treatment for uncomplicated UTIs in premenopausal women. Alternatives to co-trimoxazole include nitrofurantoin, amoxicillin-clavulanic acid, cephalosporin, fosfomycin, ofloxacin, and ciprofloxacin. Unfortunately, bacteria have exhibited increasing resistance against these first- and second-line antibiotics. Beta-lactam antibiotics are no longer recommended as a first-line therapy because *E. coli* resistance rates now exceed 20%. Fluoroquinolones have lower resistance rates, under 10%, but these resistance rates have been trending upward.

Treatment for cUTIs, however, is not as clearly defined. Currently, recommendations for first-line antibiotics in treating cUTIs are IV therapy with a fluoroquinolone, a carbapenem, a third generation cephalosporin, or piperacillin-tazobactam. Resistance to co-trimoxazole is seen in most cases of cUTIs so it is not recommended. For patients with sepsis most likely caused by ESBL-producing bacteria, imipenem or meropenem is recommended. In recent years, the efficacy of cephalosporins and piperacillin-tazobactam has decreased due to rising resistance, leaving few treatment options when resistant pathogens are present.

The FDA has approved several antibiotics specifically for cUTIs, DORIBAX (doripenem) in 2007, ZERBAXA (ceftolozane/tazobactam) in 2014, and AVYCAZ (ceftazidime-avibactam) in 2015. Several other marketed drugs (such as Levofloxacin, ertapenem, ceftriaxone, ceftazidime, imipenem/cilastatin) also have cUTI indications in their product labels/full prescribing information. Although DORIBAX is stable to beta-lactamases, it is labile to carbapenemases. This drug also carries a low risk of seizures, which is common to the carbapenem family, and increases the risk of *C. difficile* infections. ZERBAXA carries a warning of reduced effectiveness in patients with kidney impairment, which may limit its use in the most severe cUTI cases.

Further complicating the treatment of UTI is the fact that many antibiotics bind proteins, thus severely limiting their bioavailability in the unitary tract and their effectiveness against UTI. For example, glycylcyclines are a new class of antibiotics derived from tetracycline. Glycylcyclines (such as tigecycline and eravacycline) are specifically designed to overcome two common mechanisms of tetracycline resistance—resistance mediated by acquired efflux pumps and/or ribosomal protection. Presently, tigecycline is the only glycylcycline approved for clinical use. Although the precise mechanism is unclear, tigecycline has been observed to exhibit increased protein binding with increasing tigecycline concentrations. At tigecycline concentrations of 0.1 and 1.0 µg/mL, protein binding was 71% and 87%, respectively, as determined by use of an ultrafiltration technique, and was 73% and 79%, respectively, as determined by use of ultracentrifugation (Meagher et al., *Clinical Infectious Diseases* Vol. 41, Supp. 5: S333-S340, 2005). This apparent limitation in bioavailability in the urinary tract is further compounded by the inability to increase dose, partly due to the many undesirable side effects associated with tetracycline class antibiotics such as nausea, vomiting, diarrhea, and other GI tract adverse events (AEs).

Another glycylcycline, eravacycline, was recently announced to have failed to achieve its primary endpoint of statistical non-inferiority compared to the comparator drug levofloxacin, in the IGNITE2 phase 3 clinical trial of eravacycline administered as an IV to oral transition therapy for the treatment of complicated urinary tract infections (cUTI). This is despite the previously reported positive data from the IGNITE1 phase 3 clinical trial of eravacycline administered intravenously (IV) in complicated intra-abdominal infections (cIAI) which did meet its primary endpoint (Tetraphase Press Release, Sep. 8, 2015).

The developer of the candidate drug eravacycline—Tetraphase Pharmaceuticals—has since shown analysis that subjects treated with IV alone, or stayed on IV longer, responded better than those switching to oral, suggesting that the failed clinical trial is likely due to insufficient exposure with the oral formulation. Tetraphase has also announced plans to conduct an IV only cUTI study.

Thus overall, resistant bacteria have complicated the treatment landscape for UTIs. Due to the co-expression of resistance mechanisms, these bacteria may also be resistant to non-beta lactam antibiotics like fluoroquinolones, trimethoprim, and gentamicin. Increasing resistance has led clinicians to rely on older drugs that are less effective and often carry greater safety risks. Alternative options are limited highlighting the need for next generation treatments for cUTIs.

Furthermore, there are no oral antibiotics that are reliably effective treatments for UTI in the current environment of antibiotic resistance in uropathogenic bacteria. Current treatment may require the use of intravenous (IV) drugs, which necessitates hospital visits and drives up the total cost of treatment, not to mention the relative inflexibility in dosing options. The vast majority of physicians recognize the need for an oral antibiotic solution to this problem and an effective oral antibiotic that does not sacrifice safety would likely be widely used.

SUMMARY OF THE INVENTION

The invention described herein provides 9-aminomethyl minocyclines, such as 9-[(2,2-dimethyl-propyl amino)-methyl]-minocycline (Compound 1, also known as Omadacycline), for use in the treatment of UTI. The invention is partly based on the discovery that 9-aminomethyl minocyclines, such as Compound 1, has very low or minimal level of protein binding, and thus may have a high bioavailability in urinary tract for the treatment of UTI. In particular, the study assessed the in vitro plasma protein binding (concentration dependency) of Compound 1 in mouse, rat, monkey, and human. The results showed that Compound 1 was weakly bound to plasma proteins of all tested species with no major species differences. In the concentration range of 10-10,000 ng/mL of Compound 1, no obvious concentration dependency of plasma protein binding was found. The following mean unbound protein fractions (fu) in plasma were determined: rat ($73.9 \pm 12.1\%$)≤monkey ($78.8 \pm 7.26\%$)≈human ($78.7 \pm 9.72\%$)≤mouse ($84.7 \pm 5.31\%$).

In addition, in a recent Phase I study, Applicant discovered high levels of Compound 1 in the urine of patients, indicating that it may be an effective front-line therapy in the treatment of UTIs, including uUTI (cystitis) and cUTI, and UTI resulting from *E. coli* attached to the bladder wall and forming an immune response-resistant biofilm. The high bioavailability of Compound 1 in the urinary tract is further enhanced by the fact that Compound 1 has relatively mild or low GI tract AEs, such as nausea, vomiting, and diarrhea.

The invention is also partly based on the discovery that 9-aminomethyl minocyclines, such as Compound 1, can be provided as oral dosage form for the treatment of UTI, either alone or in combination with IV dosage form (such as an oral step down after initial IV doses). In a related aspect, the invention provides the use of 9-aminomethyl minocyclines, such as Compound 1, as IV dosage form for the treatment of UTI, particularly for treating cUTI.

The invention is further based on the discovery that 9-aminomethyl minocyclines, such as Compound 1, has a relatively broad spectrum against a wide variety of pathogens associated with UTI, including multidrug-resistant (MDR) pathogens including MRSA and E. coli (e.g., ESBL+ E. coli). Thus 9-aminomethyl minocyclines, such as Compound 1, are advantageous for treatment of UTI associated with antibiotic-resistant pathogens, including community-acquired UTI where resistance is a concern. Due to its efficacy against resistant pathogens, 9-aminomethyl minocyclines, such as Compound 1, can also be used as a front-line therapeutic agent in cases in which known or suspected drug-resistant bacteria may be the causative pathogen. On the other hand, 9-aminomethyl minocyclines, such as Compound 1, can also be used as a therapeutic agent in patients who have previously been treated by other antibiotics, but have had inadequate response or have developed/exhibited unacceptable or undesirable AEs, such as GI tract AEs.

Thus one aspect of the invention provides a method of treating urinary tract infection (UTI) in a subject in need of treatment thereof, comprising administering to the subject an oral dose of 300-600 mg of 9-[(2,2-dimethyl-propyl amino)-methyl]-minocycline or a salt thereof, such that the subject is treated.

In certain embodiments, the oral dose is 300-450 mg of 9-[(2,2-dimethyl-propyl amino)-methyl]-minocycline or salt thereof.

In certain embodiments, the method comprises administering to the subject one oral dose of 300 mg of 9-[(2,2-dimethyl-propyl amino)-methyl]-minocycline or salt thereof once every 24 hours, for a total of 4 or 5 days.

In certain embodiments, the method comprises administering to said subject one oral dose of 300 mg of 9-[(2,2-dimethyl-propyl amino)-methyl]-minocycline or salt thereof once every 24 hours, for a total of 5-14 days.

In certain embodiments, the method comprises administering to said subject one oral dose of 450 mg of 9-[(2,2-dimethyl-propyl amino)-methyl]-minocycline or salt thereof once every 24 hours, for a total of 5-14 days.

In certain embodiments, the method comprises administering to the subject one oral dose of 300 mg of 9-[(2,2-dimethyl-propyl amino)-methyl]-minocycline or salt thereof once every 24 hours, for a total of 5 days, and further comprising administering to the subject an additional oral dose of 300 mg of 9-[(2,2-dimethyl-propyl amino)-methyl]-minocycline or salt thereof about 12 hours after the first oral dose.

In certain embodiments, the method comprises administering to the subject one oral dose of 300 mg of 9-[(2,2-dimethyl-propyl amino)-methyl]-minocycline or salt thereof once every 24 hours, for a total of 5-14 days, and further comprising administering to the subject an additional oral dose of 300 mg of 9-[(2,2-dimethyl-propyl amino)-methyl]-minocycline or salt thereof about 12 hours after the first oral dose.

In certain embodiments, the method comprises administering to the subject one oral dose of 450 mg of 9-[(2,2-dimethyl-propyl amino)-methyl]-minocycline or salt thereof once every 24 hours, for a total of 5 days, and further comprising administering to the subject an additional oral dose of 450 mg of 9-[(2,2-dimethyl-propyl amino)-methyl]-minocycline or salt thereof about 12 hours after the first oral dose.

In certain embodiments, the method comprises administering to the subject one oral dose of 450 mg of 9-[(2,2-dimethyl-propyl amino)-methyl]-minocycline or salt thereof once every 24 hours, for a total of 5-14 days, and further comprising administering to the subject an additional oral dose of 450 mg of 9-[(2,2-dimethyl-propyl amino)-methyl]-minocycline or salt thereof about 12 hours after the first oral dose.

In certain embodiments, the method comprises administering to the subject one oral dose of 600 mg of 9-[(2,2-dimethyl-propyl amino)-methyl]-minocycline or salt thereof once every 24 hours, for a total of 5 days, and further comprising administering to the subject an additional oral dose of 600 mg of 9-[(2,2-dimethyl-propyl amino)-methyl]-minocycline or salt thereof about 12 hours after the first oral dose.

In certain embodiments, the method comprises administering to the subject: (1) one or more loading doses of 9-[(2,2-dimethyl-propyl amino)-methyl]-minocycline or salt thereof at the first day of treatment; followed by, (2) one or more maintenance doses of 9-[(2,2-dimethyl-propyl amino)-methyl]-minocycline or salt thereof, wherein the maintenance doses are administered about 24 hours apart.

In certain embodiments, the one or more loading doses are two intravenous (IV) doses of about 100 mg of 9-[(2,2-dimethyl-propyl amino)-methyl]-minocycline or salt thereof, administered about 12 hours apart.

In certain embodiments, the one or more loading doses is one intravenous (IV) dose of about 200 mg of 9-[(2,2-dimethyl-propyl amino)-methyl]-minocycline or salt thereof.

In certain embodiments, the one or more loading doses are two intravenous (IV) doses of about 200 mg of 9-[(2,2-dimethyl-propyl amino)-methyl]-minocycline or salt thereof, administered about 12 hours apart.

In certain embodiments, the one or more loading doses is one oral dose of about 300 mg of 9-[(2,2-dimethyl-propyl amino)-methyl]-minocycline or salt thereof.

In certain embodiments, the one or more loading doses are two oral doses of about 300 mg of 9-[(2,2-dimethyl-propyl amino)-methyl]-minocycline or salt thereof, administered about 12 hours apart.

In certain embodiments, the one or more loading doses are two oral doses of about 450 mg of 9-[(2,2-dimethyl-propyl amino)-methyl]-minocycline or salt thereof, administered about 12 hours apart.

In certain embodiments, the one or more loading doses are two oral doses of about 600 mg of 9-[(2,2-dimethyl-propyl amino)-methyl]-minocycline or salt thereof, administered about 12 hours apart.

In certain embodiments, the one or more loading doses are one intravenous (IV) dose of about 100 mg of 9-[(2,2-dimethyl-propyl amino)-methyl]-minocycline or salt thereof, and one oral dose of about 300 mg of 9-[(2,2-dimethyl-propyl amino)-methyl]-minocycline or salt thereof, administered about 12 hours apart.

In certain embodiments, the one IV dose is administered before said one oral dose.

In certain embodiments, each of the one or more maintenance doses comprises about 300 mg of 9-[(2,2-dimethyl-propyl amino)-methyl]-minocycline or salt thereof.

In certain embodiments, each of the one or more maintenance doses comprises about 450 mg of 9-[(2,2-dimethyl-propyl amino)-methyl]-minocycline or salt thereof.

In certain embodiments, each of the one or more maintenance doses comprises about 600 mg of 9-[(2,2-dimethyl-propyl amino)-methyl]-minocycline or salt thereof.

In certain embodiments, the one or more maintenance doses comprise one or more intravenous (IV) maintenance doses of about 100 mg of 9-[(2,2-dimethyl-propyl amino)-methyl]-minocycline or salt thereof, and one or more oral maintenance doses of about 300 mg or 450 mg of 9-[(2,2-dimethyl-propyl amino)-methyl]-minocycline or salt thereof.

In certain embodiments, the IV maintenance doses are administered before the oral maintenance doses.

In certain embodiments, the one or more maintenance doses are administered on the $2^{nd}$-$5^{th}$ day of treatment.

In certain embodiments, the one or more maintenance doses are administered on the $2^{nd}$-$14^{th}$ day of treatment.

Another aspect of the invention provides a method of treating urinary tract infection (UTI) in a subject in need of treatment thereof, comprising administering to the subject an intravenous (IV) dose of about 200 mg of 9-[(2,2-dimethyl-propyl amino)-methyl]-minocycline or a salt thereof, followed by four oral doses of 300 mg of 9-[(2,2-dimethyl-propyl amino)-methyl]-minocycline or salt thereof, such that the subject is treated, wherein the IV dose and the four oral doses are administered about 24 hrs apart from one another.

A related aspect of the invention provides a method of treating urinary tract infection (UTI) in a subject in need of treatment thereof, comprising administering to the subject an intravenous (IV) dose of about 200 mg of 9-[(2,2-dimethyl-propyl amino)-methyl]-minocycline or a salt thereof, followed by 4-13 oral doses of 300 mg of 9-[(2,2-dimethyl-propyl amino)-methyl]-minocycline or salt thereof, such that the subject is treated, wherein the IV dose and the 4-13 oral doses are administered about 24 hrs apart from one another.

A related aspect of the invention provides a method of treating urinary tract infection (UTI) in a subject in need of treatment thereof, comprising administering to the subject two intravenous (IV) doses administered 12 hours apart, each about 100 mg of 9-[(2,2-dimethyl-propyl amino)-methyl]-minocycline or a salt thereof, followed by 4-13 oral doses of 300 mg of 9-[(2,2-dimethyl-propyl amino)-methyl]-minocycline or salt thereof, such that the subject is treated, wherein the first of the two IV doses and the 4-13 oral doses are administered about 24 hrs apart from one another.

A related aspect of the invention provides a method of treating urinary tract infection (UTI) in a subject in need of treatment thereof, comprising administering to the subject an intravenous (IV) dose of about 100 mg of 9-[(2,2-dimethyl-propyl amino)-methyl]-minocycline or a salt thereof, followed by 4-13 oral doses of 300 mg of 9-[(2,2-dimethyl-propyl amino)-methyl]-minocycline or salt thereof, wherein the IV dose and the 4-13 oral doses are administered about 24 hrs apart from one another; further comprising administering to the subject an additional oral dose of 300 mg of 9-[(2,2-dimethyl-propyl amino)-methyl]-minocycline or salt thereof, administered about 12 hrs from the IV dose, such that the subject is treated.

A related aspect of the invention provides a method of treating urinary tract infection (UTI) in a subject in need of treatment thereof, comprising administering to the subject an intravenous (IV) dose of about 200 mg of 9-[(2,2-dimethyl-propyl amino)-methyl]-minocycline or a salt thereof, followed by four oral doses of 450 mg of 9-[(2,2-dimethyl-propyl amino)-methyl]-minocycline or salt thereof, such that the subject is treated, wherein the IV dose and the four oral doses are administered about 24 hrs apart from one another.

A related aspect of the invention provides a method of treating urinary tract infection (UTI) in a subject in need of treatment thereof, comprising administering to the subject an intravenous (IV) dose of about 200 mg of 9-[(2,2-dimethyl-propyl amino)-methyl]-minocycline or a salt thereof, followed by 4-13 oral doses of 450 mg of 9-[(2,2-dimethyl-propyl amino)-methyl]-minocycline or salt thereof, such that the subject is treated, wherein the IV dose and the 4-13 oral doses are administered about 24 hrs apart from one another.

A related aspect of the invention provides a method of treating urinary tract infection (UTI) in a subject in need of treatment thereof, comprising administering to the subject two intravenous (IV) doses administered 12 hours apart, each about 100 mg of 9-[(2,2-dimethyl-propyl amino)-methyl]-minocycline or a salt thereof, followed by 4-13 oral doses of 450 mg of 9-[(2,2-dimethyl-propyl amino)-methyl]-minocycline or salt thereof, such that the subject is treated, wherein the first of the two IV doses and the 4-13 oral doses are administered about 24 hrs apart from one another.

A related aspect of the invention provides a method of treating urinary tract infection (UTI) in a subject in need of treatment thereof, comprising administering to the subject an intravenous (IV) dose of about 100 mg of 9-[(2,2-dimethyl-propyl amino)-methyl]-minocycline or a salt thereof, followed by 4-13 oral doses of 450 mg of 9-[(2,2-dimethyl-propyl amino)-methyl]-minocycline or salt thereof, wherein the IV dose and the 4-13 oral doses are administered about 24 hrs apart from one another; further comprising administering to the subject an additional oral dose of 450 mg of 9-[(2,2-dimethyl-propyl amino)-methyl]-minocycline or salt thereof, administered about 12 hrs from the IV dose, such that the subject is treated.

Another aspect of the invention provides a method of treating urinary tract infection (UTI) in a subject in need of treatment thereof, comprising administering to the subject five oral doses of about 300 mg each of 9-[(2,2-dimethyl-propyl amino)-methyl]-minocycline or a salt thereof, administered about 24 hrs apart from one another; and further comprising administering to the subject an additional oral dose of 300 mg of 9-[(2,2-dimethyl-propyl amino)-methyl]-minocycline or salt thereof, administered about 12 hrs from the first of said five oral doses, such that said subject is treated.

A related aspect of the invention provides a method of treating urinary tract infection (UTI) in a subject in need of treatment thereof, comprising administering to the subject 5-14 oral doses of about 300 mg each of 9-[(2,2-dimethyl-propyl amino)-methyl]-minocycline or a salt thereof, administered about 24 hrs apart from one another; and further comprising administering to the subject an additional oral dose of 300 mg of 9-[(2,2-dimethyl-propyl amino)-methyl]-minocycline or salt thereof, administered about 12 hrs from the first of the 5-14 oral doses, such that the subject is treated.

Yet another aspect of the invention provides a method of treating urinary tract infection (UTI) in a subject in need of treatment thereof, comprising administering to the subject five oral doses of about 450 mg each of 9-[(2,2-dimethyl-propyl amino)-methyl]-minocycline or a salt thereof, administered about 24 hrs apart from one another; and further comprising administering to the subject an additional oral dose of 450 mg of 9-[(2,2-dimethyl-propyl amino)-methyl]-minocycline or salt thereof, administered about 12 hrs from the first of the five oral doses, such that the subject is treated.

A related aspect of the invention provides a method of treating urinary tract infection (UTI) in a subject in need of treatment thereof, comprising administering to the subject 5-14 oral doses of about 450 mg each of 9-[(2,2-dimethyl-propyl amino)-methyl]-minocycline or a salt thereof, administered about 24 hrs apart from one another; and further comprising administering to the subject an additional oral dose of 450 mg of 9-[(2,2-dimethyl-propyl amino)-methyl]-minocycline or salt thereof, administered about 12 hrs from the first of the 5-14 oral doses, such that the subject is treated.

Still another aspect of the invention provides a method of treating urinary tract infection (UTI) in a subject in need of treatment thereof, comprising administering to the subject five oral doses of about 600 mg each of 9-[(2,2-dimethyl-propyl amino)-methyl]-minocycline or a salt thereof, administered about 24 hrs apart from one another; and further comprising administering to the subject an additional oral dose of 600 mg of 9-[(2,2-dimethyl-propyl amino)-methyl]-minocycline or salt thereof, administered about 12 hrs from the first of the five oral doses, such that the subject is treated.

In certain embodiments, the UTI is uncomplicated urinary tract infection (uUTI) or cystitis. In certain embodiments, the UTI is complicated urinary tract infection (cUTI) or pyelonephritis. In certain embodiments, the UTI is community-acquired. In certain embodiments, the UTI is hospital-acquired or healthcare-associated (e.g., acquired during urinary catheterization).

In certain embodiments, the UTI is characterized by the presence of a pathogen selected from the group consisting of: *Escherichia coli* (ESBL$^+$, ESBL$^-$, FQS, FQR, Carbapenem-resistant, Carbapenem-susceptible), *Staphylococcus saprophyticus*, *Klebsiella pneumoniae* (ESBL$^+$, ESBL$^-$, FQS, FQR), and *Enterococcus* (*E. faecalis* VS, *E. faecalis* VNS, *E. faecalis* Vancomycin-Resistant (VRE), *E. faecium* VS, *E. faecium* VNS, *E. faecium* Vancomycin-Resistant (VRE)), MSSA, MRSA, MSCoNS, MRCoNS, *Streptococcus agalactiae* (group B streptococci), *K. oxytoca, E. cloacae* CeftazS, *E. cloacae* CeftazR, *Citrobacter* spp., *S. marcescens*, and *Acinetobacter*. The pathogen comprises extended spectrum beta-lactamase (ESBL)-producing *E. coli* (e.g., those that are resistant to multiple antibiotics).

In certain embodiments, the pathogen has a titer of ≥$10^5$ CFU/mL in a urine culture from said subject.

In certain embodiments, the subject has two or more of the clinical signs and symptoms of a UTI selected from: (1) chills or rigors or warmth associated with fever (e.g., oral temperature greater than 38° C.); (2) flank pain (pyelonephritis) or pelvic pain (cUTI); (3) nausea or vomiting; (4) dysuria, urinary frequency, or urinary urgency; (4) costovertebral angle tenderness on physical examination; (5) urine specimen with evidence of pyuria (e.g., dipstick analysis positive for leukocyte esterase, or at least 10 white blood cells per cubic millimeter); and (6) suprapubic pain.

In certain embodiments, the subject is treated as demonstrated by a post treatment reduction of at least 10-fold in pathogen titer of a urine culture from said subject.

In certain embodiments, the subject has a post treatment pathogen titer of less than $10^4$ CFU/mL on the urine culture from said subject.

In certain embodiments, the subject is a female. For example, the female may be diabetic, pregnant, have multiple sclerosis, and/or have a condition that affects urine flow (such as kidney stones, stroke, and spinal cord injury).

In certain embodiments, each of the oral dose is administered independently as two or three 150-mg tablets.

In certain embodiments, each of the IV dose is administered continuously over about 30 minutes (e.g., at least 30 minutes and not more than 45 minutes).

Another aspect of the invention provides a method of treating urinary tract infection (UTI) in a subject in need of treatment thereof, comprising administering to the subject an IV dose of about 100-200 mg of 9-[(2,2-dimethyl-propyl amino)-methyl]-minocycline or a salt thereof, such that the subject is treated.

In certain embodiments, the subject is not administered oral dose of 9-[(2,2-dimethyl-propyl amino)-methyl]-minocycline or a salt thereof.

In certain embodiments, the IV dose is about 100 mg or about 200 mg of 9-[(2,2-dimethyl-propyl amino)-methyl]-minocycline or a salt thereof.

In certain embodiments, the method comprises administering to the subject one IV dose of about 100 mg of 9-[(2,2-dimethyl-propyl amino)-methyl]-minocycline or salt thereof, once every 24 hours, for a total of 3, 4, 5, 6, 7, 8, 9, 10, 11, 12, 13, or 14 days.

In certain embodiments, the method comprises administering to the subject one IV dose of about 100 mg of 9-[(2,2-dimethyl-propyl amino)-methyl]-minocycline or salt thereof, once every 24 hours, for a total of 5-14 days.

In certain embodiments, the method further comprises administering to the subject an additional IV dose of about 100 mg of 9-[(2,2-dimethyl-propyl amino)-methyl]-minocycline or salt thereof, about 12 hours after the first IV dose.

In certain embodiments, the UTI is cUTI or pyelonephritis.

It should be understood that any one embodiments described herein, including those described only in the Example section, can be combined with any one or more other embodiments unless expressly disclaimed or otherwise improper.

DETAILED DESCRIPTION OF THE INVENTION

Figure 1:
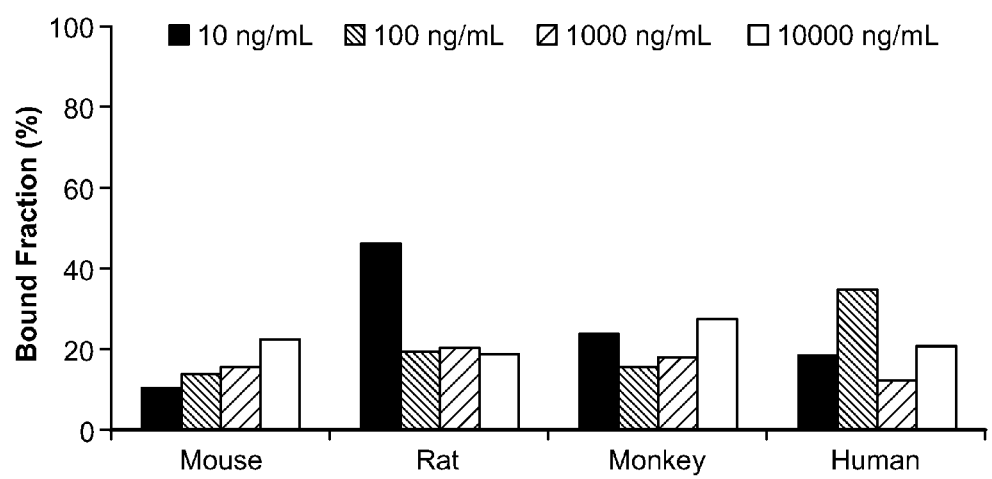
FIG. 1 shows plasma protein bound fraction for Compound 1 in mouse, rat, monkey, and human plasma by nominal concentration of plasma.

The invention pertains, at least in part, to the discovery that 9-[(2,2-dimethyl-propyl amino)-methyl]-minocycline (Compound 1) is effective to treat certain bacterial infections, such as Urinary tract infections (UTIs), including uncomplicated and complicated UTIs (cUTIs), based on a specific dosage and administration regimen.

Thus in one aspect, the invention provides a method of treating urinary tract infection (UTI) (e.g., uncomplicated UTI (uUTI) or complicated UTI (cUTI)) in a subject in need of treatment thereof. In a $1^{st}$ embodiment, the method comprises administering to the subject an oral dose of 300-600 mg of 9-[(2,2-dimethyl-propyl amino)-methyl]-minocycline or a salt thereof, such that said subject is treated.

In a $2^{nd}$ embodiment, the oral dose of the 1st embodiment is 300-450 mg of 9-[(2,2-dimethyl-propyl amino)-methyl]-minocycline or a salt thereof.

In a $3^{rd}$ embodiment, the method of the first embodiment comprises administering to the subject one oral dose of 300 mg of 9-[(2,2-dimethyl-propyl amino)-methyl]-minocycline or a salt thereof once every 24 hours, for a total of 4 or 5 days.

In a $4^{th}$ embodiment, the method comprises administering to said subject one oral dose of 300 mg of 9-[(2,2-dimethyl-propyl amino)-methyl]-minocycline or salt thereof once every 24 hours, for a total of 5-14 days.

In a $5^{th}$ embodiments, the method comprises administering to said subject one oral dose of 450 mg of 9-[(2,2-dimethyl-propyl amino)-methyl]-minocycline or salt thereof once every 24 hours, for a total of 5-14 days.

In a $6^{th}$ embodiment, the method of the $1^{st}$ embodiment comprises administering to the subject one oral dose of 300 mg of 9-[(2,2-dimethyl-propyl amino)-methyl]-minocycline or salt thereof once every 24 hours, for a total of 5 days, and further comprising administering to said subject an additional oral dose of 300 mg of 9-[(2,2-dimethyl-propyl amino)-methyl]-minocycline or salt thereof about 12 hours after the first oral dose.

In a $7^{th}$ embodiments, the method comprises administering to the subject one oral dose of 300 mg of 9-[(2,2-dimethyl-propyl amino)-methyl]-minocycline or salt thereof once every 24 hours, for a total of 5-14 days, and further comprising administering to the subject an additional oral dose of 300 mg of 9-[(2,2-dimethyl-propyl amino)-methyl]-minocycline or salt thereof about 12 hours after the first oral dose.

In an $8^{th}$ embodiment, the method of the $1^{st}$ embodiment comprises administering to the subject one oral dose of 450 mg of 9-[(2,2-dimethyl-propyl amino)-methyl]-minocycline or salt thereof once every 24 hours, for a total of 5 days, and further comprising administering to said subject an additional oral dose of 450 mg of 9-[(2,2-dimethyl-propyl amino)-methyl]-minocycline or salt thereof about 12 hours after the first oral dose.

In a $9^{th}$ embodiments, the method comprises administering to the subject one oral dose of 450 mg of 9-[(2,2-dimethyl-propyl amino)-methyl]-minocycline or salt thereof once every 24 hours, for a total of 5-14 days, and further comprising administering to the subject an additional oral dose of 450 mg of 9-[(2,2-dimethyl-propyl amino)-methyl]-minocycline or salt thereof about 12 hours after the first oral dose.

In a $10^{th}$ embodiment, the method of the $1^{st}$ embodiment comprises administering to the subject one oral dose of 600 mg of 9-[(2,2-dimethyl-propyl amino)-methyl]-minocycline or salt thereof once every 24 hours, for a total of 5 days, and further comprising administering to the subject an additional oral dose of 600 mg of 9-[(2,2-dimethyl-propyl amino)-methyl]-minocycline or salt thereof about 12 hours after the first oral dose.

In a $11^{th}$ embodiment, the method of the $1^{st}$ embodiment comprises administering to the subject: (1) one or more loading doses of 9-[(2,2-dimethyl-propyl amino)-methyl]-minocycline or salt thereof at the first day of treatment; followed by, (2) one or more maintenance doses of 9-[(2,2-dimethyl-propyl amino)-methyl]-minocycline or salt thereof, wherein the maintenance doses are administered about 24 hours apart.

In a $12^{th}$ embodiment, the one or more loading doses of the $11^{th}$ embodiment are two intravenous (IV) doses of about 100 mg of 9-[(2,2-dimethyl-propyl amino)-methyl]-minocycline or salt thereof, administered about 12 hours apart.

In a $13^{th}$ embodiment, the one or more loading doses of the $11^{th}$ embodiment is one intravenous (IV) dose of about 200 mg of 9-[(2,2-dimethyl-propyl amino)-methyl]-minocycline or salt thereof.

In a $14^{th}$ embodiment, the one or more loading doses of the $11^{th}$ embodiment are two intravenous (IV) doses of about 200 mg of 9-[(2,2-dimethyl-propyl amino)-methyl]-minocycline or salt thereof, administered about 12 hours apart.

In an $15^{th}$ embodiment, the one or more loading doses of the $11^{th}$ embodiment is one oral dose of about 300 mg of 9-[(2,2-dimethyl-propyl amino)-methyl]-minocycline or salt thereof.

In a $16^{th}$ embodiment, the one or more loading doses of the $11^{th}$ embodiment are two oral doses of about 300 mg of 9-[(2,2-dimethyl-propyl amino)-methyl]-minocycline or salt thereof, administered about 12 hours apart.

In a $17^{th}$ embodiment, the one or more loading doses of the $11^{th}$ embodiment are two oral doses of about 450 mg of 9-[(2,2-dimethyl-propyl amino)-methyl]-minocycline or salt thereof, administered about 12 hours apart.

In a $18^{th}$ embodiment, the one or more loading doses of the $11^{th}$ embodiment are two oral doses of about 600 mg of 9-[(2,2-dimethyl-propyl amino)-methyl]-minocycline or salt thereof, administered about 12 hours apart.

In a $19^{th}$ embodiment, the one or more loading doses of the $11^{th}$ embodiment are one intravenous (IV) dose of about 100 mg of 9-[(2,2-dimethyl-propyl amino)-methyl]-minocycline or salt thereof, and one oral dose of about 300 mg of 9-[(2,2-dimethyl-propyl amino)-methyl]-minocycline or salt thereof, administered about 12 hours apart.

In a $20^{th}$ embodiment, the one IV dose of the $19^{th}$ embodiment is administered before the one oral dose.

In a $21^{st}$ embodiment, each of the one or more maintenance doses of any one of the $11^{th}$-$20^{th}$ embodiments comprises about 300 mg of 9-[(2,2-dimethyl-propyl amino)-methyl]-minocycline or the salt thereof.

In a $22^{nd}$ embodiment, each of the one or more maintenance doses of any one of the $11^{th}$-$20^{th}$ embodiments comprises about 450 mg of 9-[(2,2-dimethyl-propyl amino)-methyl]-minocycline or salt thereof.

In a $23^{rd}$ embodiment, each of the one or more maintenance doses of any one of the $11^{th}$-$20^{th}$ embodiments comprises about 600 mg of 9-[(2,2-dimethyl-propyl amino)-methyl]-minocycline or salt thereof.

In a 24$^{th}$ embodiment, the one or more maintenance doses of any one of the 11$^{th}$-20$^{th}$ embodiments comprise one or more intravenous (IV) maintenance doses of about 100 mg of 9-[(2,2-dimethyl-propyl amino)-methyl]-minocycline or salt thereof, and one or more oral maintenance doses of about 300 mg or 450 mg of 9-[(2,2-dimethyl-propyl amino)-methyl]-minocycline or salt thereof.

In a 25$^{th}$ embodiment, the IV maintenance doses of the 24$^{th}$ embodiment are administered before the oral maintenance doses.

In a 26$^{th}$ embodiment, the one or more maintenance doses of any one of the 11$^{th}$-25$^{th}$ embodiments are administered on the 2$^{nd}$-5$^{th}$ day of treatment.

In a 27$^{th}$ embodiments, the one or more maintenance doses of any one of the 11$^{th}$-25$^{th}$ embodiments are administered on the 2$^{nd}$-14$^{th}$ day of treatment.

In a related aspect, the invention provides a method of treating urinary tract infection (UTI) in a subject in need of treatment thereof.

Specifically, in a 28$^{th}$ embodiment, the method comprises administering to the subject an intravenous (IV) dose of about 200 mg of 9-[(2,2-dimethyl-propyl amino)-methyl]-minocycline or a salt thereof, followed by four oral doses of 300 mg of 9-[(2,2-dimethyl-propyl amino)-methyl]-minocycline or salt thereof, such that the subject is treated, wherein the IV dose and the four oral doses are administered about 24 hrs apart from one another.

In a 29$^{th}$ embodiment, the method comprises administering to the subject an intravenous (IV) dose of about 200 mg of 9-[(2,2-dimethyl-propyl amino)-methyl]-minocycline or a salt thereof, followed by 4-13 oral doses of 300 mg of 9-[(2,2-dimethyl-propyl amino)-methyl]-minocycline or salt thereof, such that the subject is treated, wherein the IV dose and the 4-13 oral doses are administered about 24 hrs apart from one another.

In a 30$^{th}$ embodiment, the method comprises administering to the subject two intravenous (IV) doses administered 12 hours apart, each about 100 mg of 9-[(2,2-dimethyl-propyl amino)-methyl]-minocycline or a salt thereof, followed by 4-13 oral doses of 300 mg of 9-[(2,2-dimethyl-propyl amino)-methyl]-minocycline or salt thereof, such that the subject is treated, wherein the first of the two IV doses and the 4-13 oral doses are administered about 24 hrs apart from one another.

In a 31$^{st}$ embodiment, the method comprises administering to the subject an intravenous (IV) dose of about 100 mg of 9-[(2,2-dimethyl-propyl amino)-methyl]-minocycline or a salt thereof, followed by 4-13 oral doses of 300 mg of 9-[(2,2-dimethyl-propyl amino)-methyl]-minocycline or salt thereof, wherein the IV dose and the 4-13 oral doses are administered about 24 hrs apart from one another; further comprising administering to the subject an additional oral dose of 300 mg of 9-[(2,2-dimethyl-propyl amino)-methyl]-minocycline or salt thereof, administered about 12 hrs from the IV dose, such that the subject is treated.

In a 32$^{nd}$ embodiment, the method comprises administering to the subject an intravenous (IV) dose of about 200 mg of 9-[(2,2-dimethyl-propyl amino)-methyl]-minocycline or a salt thereof, followed by four oral doses of 450 mg of 9-[(2,2-dimethyl-propyl amino)-methyl]-minocycline or salt thereof, such that the subject is treated, wherein the IV dose and the four oral doses are administered about 24 hrs apart from one another.

In a 33$^{rd}$ embodiment, the method comprises administering to the subject an intravenous (IV) dose of about 200 mg of 9-[(2,2-dimethyl-propyl amino)-methyl]-minocycline or a salt thereof, followed by 4-13 oral doses of 450 mg of 9-[(2,2-dimethyl-propyl amino)-methyl]-minocycline or salt thereof, such that the subject is treated, wherein the IV dose and the 4-13 oral doses are administered about 24 hrs apart from one another.

In a 34$^{th}$ embodiment, the method comprises administering to the subject two intravenous (IV) doses administered 12 hours apart, each about 100 mg of 9-[(2,2-dimethyl-propyl amino)-methyl]-minocycline or a salt thereof, followed by 4-13 oral doses of 450 mg of 9-[(2,2-dimethyl-propyl amino)-methyl]-minocycline or salt thereof, such that the subject is treated, wherein the first of the two IV doses and the 4-13 oral doses are administered about 24 hrs apart from one another.

In a 35$^{th}$ embodiment, the method comprises administering to the subject an intravenous (IV) dose of about 100 mg of 9-[(2,2-dimethyl-propyl amino)-methyl]-minocycline or a salt thereof, followed by 4-13 oral doses of 450 mg of 9-[(2,2-dimethyl-propyl amino)-methyl]-minocycline or salt thereof, wherein the IV dose and the 4-13 oral doses are administered about 24 hrs apart from one another; further comprising administering to the subject an additional oral dose of 450 mg of 9-[(2,2-dimethyl-propyl amino)-methyl]-minocycline or salt thereof, administered about 12 hrs from the IV dose, such that the subject is treated.

In a 36$^{th}$ embodiment, the method comprises administering to said subject five oral doses of about 300 mg each of 9-[(2,2-dimethyl-propyl amino)-methyl]-minocycline or a salt thereof, administered about 24 hrs apart from one another; and further comprising administering to said subject an additional oral dose of 300 mg of 9-[(2,2-dimethyl-propyl amino)-methyl]-minocycline or salt thereof, administered about 12 hrs from the first of said five oral doses, such that said subject is treated.

In a 37$^{th}$ embodiment, the method comprises administering to the subject 5-14 oral doses of about 300 mg each of 9-[(2,2-dimethyl-propyl amino)-methyl]-minocycline or a salt thereof, administered about 24 hrs apart from one another; and further comprising administering to the subject an additional oral dose of 300 mg of 9-[(2,2-dimethyl-propyl amino)-methyl]-minocycline or salt thereof, administered about 12 hrs from the first of the 5-14 oral doses, such that the subject is treated.

In a 38$^{th}$ embodiment, the method comprises administering to said subject five oral doses of about 450 mg each of 9-[(2,2-dimethyl-propyl amino)-methyl]-minocycline or a salt thereof, administered about 24 hrs apart from one another; and further comprising administering to said subject an additional oral dose of 450 mg of 9-[(2,2-dimethyl-propyl amino)-methyl]-minocycline or salt thereof, administered about 12 hrs from the first of said five oral doses, such that said subject is treated.

In a 39$^{th}$ embodiment, the method comprises administering to the subject 5-14 oral doses of about 450 mg each of 9-[(2,2-dimethyl-propyl amino)-methyl]-minocycline or a salt thereof, administered about 24 hrs apart from one another; and further comprising administering to the subject an additional oral dose of 450 mg of 9-[(2,2-dimethyl-propyl amino)-methyl]-minocycline or salt thereof, administered about 12 hrs from the first of the 5-14 oral doses, such that the subject is treated.

In a 40$^{th}$ embodiment, the method comprises administering to said subject five oral doses of about 600 mg each of 9-[(2,2-dimethyl-propyl amino)-methyl]-minocycline or a salt thereof, administered about 24 hrs apart from one another; and further comprising administering to said subject an additional oral dose of 600 mg of 9-[(2,2-dimethyl-propyl amino)-methyl]-minocycline or salt thereof, administered about 12 hrs from the first of said five oral doses, such that said subject is treated.

In a 41$^{st}$ embodiment, the UTI of any one of the 1$^{st}$-40$^{th}$ embodiments is uncomplicated urinary tract infection (uUTI) or cystitis.

In a 42$^{nd}$ embodiment, the UTI of any one of the 1$^{st}$-40$^{th}$ embodiments is complicated urinary tract infection (cUTI) or pyelonephritis.

In a 43$^{rd}$ embodiment, the UTI of any one of the 1$^{st}$-42$^{nd}$ embodiments is community-acquired.

In a 44$^{th}$ embodiment, the UTI of any one of the 1$^{st}$-42$^{nd}$ embodiments is hospital-acquired or healthcare-associated (e.g., acquired during urinary catheterization).

In a 45$^{th}$ embodiment, the UTI of any one of the 1$^{st}$-44$^{th}$ embodiments is characterized by the presence of a pathogen selected from the group consisting of: *Escherichia coli* (ESBL$^+$, ESBL$^-$, FQS, FQR, Carbapenem-resistant, Carbapenem-susceptible), *Staphylococcus saprophyticus, Klebsiella pneumoniae* (ESBL$^+$, ESBL$^-$, FQS, FQR), and *Enterococcus* (*E. faecalis* VS, *E. faecalis* VNS, *E. faecalis* Vancomycin-Resistant (VRE), *E. faecium* VS, *E. faecium* VNS, *E. faecium* Vancomycin-Resistant (VRE)), MSSA, MRSA, MSCoNS, MRCoNS, *Streptococcus agalactiae* (group B streptococci), *K. oxytoca, E. cloacae* CeftazS, *E. cloacae* CeftazR, *Citrobacter* spp., *S. marcescens*, and *Acinetobacter*. Optionally, the MIC$_{90}$ (minimal 90% inhibition concentration) of 9-[(2,2-dimethyl-propyl amino)-methyl]-minocycline or a salt thereof against the pathogen is 16 µg/mL or less, 8 µg/mL or less, 4 µg/mL or less, or 2 µg/mL or less. For example, the pathogen may be a multidrug resistant (MDR) pathogen, including MRSA and *E. coli* (e.g., ESBL$^+$*E. coli*). As used herein, "multidrug-resistant (MDR)" includes resistance to two or more classes of antibiotics, such as those commonly used oral antibiotics, including FQ resistance, Sulfa drug resistance, trimethoprim resistance, tetracycline resistance, cephalosporin resistance, penicillin resistance, etc., or combination thereof. Resistance may be specific to a chemical class or to a specific member of the class; and/or may occur alone or in various combinations in a particular isolate.

In a 46$^{th}$ embodiment, the pathogen of the 45$^{th}$ embodiment comprises extended spectrum beta-lactamase (ESBL)-producing *E. coli* (e.g., those that are resistant to multiple antibiotics).

In a 47$^{th}$ embodiment, the pathogen of the 45$^{th}$ or 46$^{th}$ embodiment has a titer of ≥10$^5$ CFU/mL in a urine culture from said subject.

In a 48$^{th}$ embodiment, the subject of any one of the 1$^{st}$-47$^{th}$ embodiments has two or more of the clinical signs and symptoms of a UTI selected from: (1) chills or rigors or warmth associated with fever (e.g., oral temperature greater than 38° C.); (2) flank pain (pyelonephritis) or pelvic pain (cUTI); (3) nausea or vomiting; (4) dysuria, urinary frequency, or urinary urgency; (4) costo-vertebral angle tenderness on physical examination; (5) urine specimen with evidence of pyuria (e.g., dipstick analysis positive for leukocyte esterase, or at least 10 white blood cells per cubic millimeter); and (6) suprapubic pain.

In a 49$^{th}$ embodiment, the subject of any one of the 1$^{st}$-48$^{th}$ embodiments is treated as demonstrated by a post treatment reduction of at least 10-fold in pathogen titer of a urine culture from the subject.

In a 50$^{th}$ embodiment, the subject of any one of the 1$^{st}$-49$^{th}$ embodiments has a post treatment pathogen titer of less than 10$^4$ CFU/mL on the urine culture from the subject.

In a 51$^{st}$ embodiment, the subject of any one of the 1$^{st}$-50$^{th}$ embodiments is a female.

In a 52$^{nd}$ embodiment, the female of the 51$^{st}$ embodiment is diabetic, is pregnant, has multiple sclerosis, and/or has a condition that affects urine flow (such as kidney stones, stroke, and spinal cord injury).

In a 53$^{rd}$ embodiment, each of the oral dose of any one of the 1$^{st}$-52$^{nd}$ embodiments is administered independently as two or three 150-mg tablets.

In a 54$^{th}$ embodiment, each of the IV dose of any one of the 1$^{st}$-53$^{rd}$ embodiments is administered continuously over about 30 minutes (e.g., at least 30 minutes and not more than 45 minutes).

Another aspect of the invention provide a method of treating urinary tract infection (UTI) in a subject in need of treatment thereof, comprising administering to the subject an IV dose of 9-[(2,2-dimethyl-propyl amino)-methyl]-minocycline or a salt thereof, such that the subject is treated.

Specifically, in a 55$^{th}$ embodiment, the invention provides a method of treating urinary tract infection (UTI) in a subject in need of treatment thereof, comprising administering to the subject an IV dose of about 100-200 mg of 9-[(2,2-dimethyl-propyl amino)-methyl]-minocycline or a salt thereof, such that the subject is treated.

In a 56$^{th}$ embodiment, the subject of the 55$^{th}$ embodiment, is not administered oral dose of 9-[(2,2-dimethyl-propyl amino)-methyl]-minocycline or a salt thereof.

In a 57$^{th}$ embodiment, the IV dose of the 55$^{th}$ or 56$^{th}$ embodiment is about 100 mg or about 200 mg of 9-[(2,2-dimethyl-propyl amino)-methyl]-minocycline or a salt thereof.

In a 58$^{th}$ embodiment, the method according to any one of the 55$^{th}$-57$^{th}$ embodiments comprises administering to the subject one IV dose of about 100 mg of 9-[(2,2-dimethyl-propyl amino)-methyl]-minocycline or salt thereof, once every 24 hours, for a total of 3, 4, 5, 6, 7, 8, 9, 10, 11, 12, 13, or 14 days.

In a 59$^{th}$ embodiment, the method of any one of the 55$^{th}$-57$^{th}$ embodiments comprises administering to the subject one IV dose of about 100 mg of 9-[(2,2-dimethyl-propyl amino)-methyl]-minocycline or salt thereof, once every 24 hours, for a total of 5-14 days.

In a 60$^{th}$ embodiment, the method of the 58$^{th}$ or 59$^{th}$ embodiment further comprises administering to the subject an additional IV dose of about 100 mg of 9-[(2,2-dimethyl-propyl amino)-methyl]-minocycline or salt thereof, about 12 hours after the first IV dose.

In a 61$^{st}$ embodiment, in the method of any one of the 55$^{th}$-60$^{th}$ embodiments, the UTI is cUTI or pyelonephritis.

As used herein, the term "subject" may include animals (e.g., non-human mammal) capable of suffering from a bacterial infection. Examples of subjects include animals such as farm animals (e.g., cows, pigs, horses, goats, rabbits, sheep, etc.), lab animals (mice, rats, etc.), pets (e.g., dogs, cats, ferrets, etc.), and primates (e.g., humans and non-human primates such as monkeys, gorillas, chimpanzees, etc.).

In any of the above embodiments, the subject may be a human, a non-human primate, or a non-human mammal.

The term "treating" or "treatment" refers to the amelioration, eradication, or diminishment of one or more symptoms of the disorder, e.g., a bacterial infection, to be treated. In certain embodiments, the disorder term includes the eradication of bacteria associated with the infection to be treated.

The term "prophylaxis" means to prevent or reduce the risk of bacterial infection.

The term "resistance" or "resistant" refers to the antibiotic/organism standards as defined by the Clinical and Laboratories Standards Institute (CLSI) and/or the Food and Drug Administration (FDA).

In certain embodiments, the infection may be resistant to other antibiotics, such as penicillin or tetracycline.

The term "effective amount" includes the amount of the tetracycline compound needed to treat a bacterial infection (e.g., UTI). For example, an effective amount describes an efficacious level sufficient to achieve the desired therapeutic effect through the killing of bacteria and/or inhibition of bacterial growth. Preferably, the bacterial infection is treated when the pathogen (e.g., bacteria) is eradicated. The bacterial infection is also treated when at least one symptom of infection is reduced, alleviated, or eliminated.

The term "evaluable clinical success" refers to a clinical trial participant who: (1) did not meet any criteria for evaluable clinical failure; (2) did not receive potentially effective non-study antibiotics for any other reason; and (3) the blinded evaluator indicated at the test of cure evaluation that the infection had sufficiently resolved such that antibiotics were not needed.

The term "evaluable clinical failure" refers to a clinical trial participant who met any one of the following criteria: the blinded evaluator discontinued study drug and indicated that the infection had responded inadequately such that alternative antibiotic(s) were needed; the blinded evaluator discontinued study drug because of an adverse event that was assessed as probably or possibly drug-related; the primary site of infection was surgically removed; or the subject had no evaluation after the end of intravenous or oral treatment.

The term "clinical success rate" refers to the number of evaluable clinical successes divided by the total number of population in the trial.

The term "microbiologically evaluable clinical success rate" refers to those who met the definition of evaluable clinical success and had an infecting pathogen at baseline.

In one embodiment, the effective amount of the tetracycline compound, e.g. 9-[(2,2-dimethyl-propyl amino)-methyl]-minocycline, when administered orally is from about 150 to about 600 mg, about 150 to about 450 mg, from about 150 to about 300 mg, from about 300 to about 600 mg, from about 300 to about 450 mg, from about 450 to about 600 mg, about 150 mg, about 300 mg, about 450 mg, or about 600 mg.

In certain embodiments, the oral dose may be about 300-600 mg, about 300-450 mg, about 350-550 mg, about 400-500 mg, or about 450 mg.

In certain embodiments, each oral dose is administered as multiples of 150 mg doses (e.g., 150 mg, 2×150 mg, 3×150 mg, or 4×150 mg). For example, a 300 mg oral dose may consists of two 150 mg tablets/pills/capsules/gels, etc.

In another embodiment, the effective amount of the tetracycline compound, e.g., 9-[(2,2-dimethyl-propyl amino)-methyl]-minocycline, when administered intravenously (IV) is from about 50 to about 200 mg, from about 50 to about 150 mg, from about 50 to about 100 mg, from about 100 mg to about 200 mg, from about 100 mg to about 150 mg, from about 150 mg to about 200 mg, about 100 mg, or about 200 mg.

The compound, either in IV formulation or in oral formulation, may be administered as a salt (e.g., tosylate salt or hydrochloride salt) or as a free base.

It is to be understood that wherever values and ranges are provided herein, e.g., in ages of subject populations, dosages, and blood levels, all values and ranges encompassed by these values and ranges, including recited upper and/or lower limits of the ranges, are meant to be encompassed within the scope of the present invention. Moreover, all values in these values and ranges may also be the upper or lower limits of a range.

In another embodiment, the tetracycline compound (e.g., Compound 1) may be administered once or twice per day, either intravenously or orally. In certain embodiments, twice per day administration has two equal doses.

In certain embodiments, the 9-[(2,2-dimethyl-propyl amino)-methyl]-minocycline has a microbiologically evaluable clinical success rate of greater than about 60%. In certain embodiments, the compound of the invention has a clinical success rate of greater than about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 93.7%, 94%, 95%, 96%, 97%, 97.5%, 98%, 99% or more, either in the intent to treat (ITT) patient population or in the clinically evaluable (CE) patient population. In the 2015 FDA cUTI guidance, microbiological ITT is considered the primary analysis population for efficacy.

As used herein, an "Intent-to-Treat (or ITT)" population refers to all enrolled clinical trial subjects. In certain embodiments, the ITT population is further limited to all enrolled clinical trial subjects who have received at least one dose of the study drug (e.g., Compound 1). A "Clinically Evaluable (or CE)" population refers to all ITT subjects who had a qualifying infection as defined by the relevant clinical protocol, e.g., those with UTI. "Clinical success" refers to the continued improvement or complete resolution of baseline symptoms in the ITT or CE populations, assessed by the clinical investigator, at a set period (e.g., 10 to 17 days) after the last dose of the study drug.

In one example, a subject is treated intravenously followed by an oral step down. In certain embodiments, the subject is treated directly by oral dose without any preceding IV dose.

In certain embodiments, the present invention provides a method of treating a subject for an infection (e.g., UTI), comprising administering to the subject an effective amount of Compound 1 or a salt thereof wherein the subject is initially treated about 1 day intravenously, followed by about 2, 3, 4, 5, 6, 7, 8, 9, 10, 11, 12, or 13 days of oral treatment, such that the subject is treated. In certain embodiments, the first day of IV treatment consists of a higher loading dose (e.g., 2× dose, or 2×100 mg doses). In certain embodiments, the total treatment period is about 4, 5, 6, or 7 days. In certain embodiments, one (e.g., the $2^{nd}$ IV loading dose) or both of the IV loading doses is replaced by a 300 mg or 450 mg oral dose.

In another embodiment, the present invention provides a method of treating a subject for an infection (e.g., UTI), comprising administering to said subject an effective amount of Compound 1 or a salt thereof wherein the subject initially treated intravenously has elevated compound 1 blood levels followed by reduced compound 1 blood levels with oral treatment, such that the subject is treated. In certain embodiments, the initially elevated compound 1 blood level is achieved by a higher (e.g., 2×) loading dose(s).

Pharmaceutical Compositions of the Invention

The invention also pertains to pharmaceutical compositions comprising a therapeutically effective amount of a tetracycline compound (e.g., a 9-aminomethyl tetracycline compound, e.g., 9-[(2,2-dimethyl-propyl amino)-methyl]-minocycline) or a salt thereof and, optionally, a pharmaceutically acceptable carrier.

In a further embodiment, the invention pertains to a pharmaceutical composition comprising from about 100 to about 700 mg (e.g., about 300, 450, or 600 mg) of 9-[(2,2-dimethyl-propyl amino)-methyl]-minocycline or a salt thereof and a pharmaceutically acceptable carrier. In a further embodiment, the pharmaceutically acceptable carrier is acceptable for oral administration. In another further embodiment, the tetracycline compound is a free base or a tosylate salt.

In yet another further embodiment, the composition comprises from about 110 to about 490 mg, from about 120 to about 480 mg, from about 130 to about 470 mg, from about 140 to about 460 mg, from about 150 to about 450 mg, from about 160 to about 440 mg, from about 170 mg to about 430 mg, from about 180 mg to about 420 mg, from about 190 mg to about 410 mg, from about 200 mg to about 400 mg, from about 210 mg to about 390 mg, from about 220 mg to about 380 mg, from about 230 mg to about 370 mg, from about 240 mg to about 360 mg, from about 250 mg to about 350 mg, from about 260 mg to about 340 mg, from about 270 mg to about 330 mg, from about 280 mg to about 320 mg, from about 290 mg to about 310 mg, or about 300 mg of 9-[(2,2-dimethyl-propyl amino)-methyl]-minocycline. Optionally, the pharmaceutically acceptable carrier is suitable for oral administration.

In another embodiment, the invention also pertains to a pharmaceutical composition comprising from about 50 to about 250 mg of 9-[(2,2-dimethyl-propylamino)-methyl]-minocycline or a salt thereof (e.g., a hydrochloride salt) and a pharmaceutically acceptable carrier suitable for intravenous administration.

In yet another further embodiment, the composition comprises from about 100 to about 300 mg, from about 125 to about 275 mg, from about 150 mg to about 250 mg, from about 100 mg to about 200 mg, about 100 mg, or about 200 mg of 9-[(2,2-dimethyl-propyl amino)-methyl]-minocycline.

The language "pharmaceutically acceptable carrier" includes substances capable of being co-administered with the tetracycline compound of the invention, e.g., 9-[(2,2-dimethyl-propyl amino)-methyl]-minocycline, and which allow the tetracycline compound to perform its intended function, e.g., treat or prevent a bacterial infection. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention (e.g., Compound 1) that are basic in nature are capable of forming a wide variety of salts with various inorganic and organic acids. The acids that may be used to prepare pharmaceutically acceptable acid addition salts of the minocycline compounds of the invention that are basic in nature are those that form nontoxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a minocycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. Preferably, the tetracycline compound of the invention is administered as a tosylate (e.g., p-toluenesulfonate) salt or as a freebase orally or as a hydrochloride salt intravenously.

The tetracycline compounds of the invention (e.g., Compound 1) and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutic compositions known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective tetracycline compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic.

These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

Efficacy Against UTI Pathogens

Urinary tract infections (UTI) occurring in catheterized patients or in patients from the community with multi-resistant bacteria present a therapeutic challenge for physicians. While most common in the hospital setting these multi-resistant bacteria, particularly Enterobacteriaceae that produce ESBL and have other resistance mechanisms are becoming increasingly common in the community. In either setting, the choices of antibiotics to treat UTI for reliable first-line treatment are limited. In addition, gram-positive organisms with increasing resistance including MRSA and *Enterococcus* species are also of treatment concern. The most common urinary tract pathogen is *E. coli*. Resistance rates for ESBL-producing clinical isolates make the use of some common antibiotics less reliable and could lead to progression to very serious spread of the organism to the kidneys, bloodstream, and other organs. For example, resistance rates for important cephalosporins range from 50% for ceftazidime to 95% for ceftriaxone, 76.5% for levofloxacin and other quinolones, and 46% for doxycycline.

Data presented herein demonstrates that Compound 1 is an effective antibiotic agent that has broad spectrum activity against the most common UTI pathogens. For example, the $MIC_{90}$ for Compound 1 against ESBL-producing *E. coli* is <4 µg/mL, compared to >8 µg/mL for ceftriaxone and >4 µg/mL for levofloxacin. In one human Phase 1 study, a single oral dose of Compound 1 resulted in estimated concentrations in urine that averaged between 7.6 and 11.2 g/mL over 24 hours; and Compound 1 concentrations in tissues including the kidneys are approximately 4 times greater than that in plasma. Concentrations after intravenous (IV) dosing and at steady-state are expected to be even greater. Thus Compound 1 can achieve concentrations in the urine that will effectively treat ESBL-producing *E. coli* and other key pathogens, thus offering a reliable first-line treatment for UTI when the impact of resistance decreases the reliability of today's most currently available IV and oral antibiotics.

a) Rodent Pharmacokinetics

Both animal and human pharmacokinetic studies have indicated that Compound 1 distributes well to tissues. Studies in mice indicate that Compound 1 achieves tissue concentrations greater than in plasma as shown in Table 1. Similar concentrations were achieved in lung and thigh muscle.

TABLE 1

Pharmacokinetics of Compound 1 in Mouse Plasma versus Kidney

| Route of Administration | Dose (mg/kg) | Plasma AUC (0-∞) | Kidney AUC (0-∞) | AUC Ratio Kidney:Plasma |
| --- | --- | --- | --- | --- |
| Subcutaneous | 4.0 | 2.816 | 11.838 | 4.20 |

In rats, based on $^{14}$C-Compound 1 dosed intravenously, approximately 30% of the dose (5 mg/kg) was excreted in the urine, with 25% excreted in the first 24 hours. The remainder of the dose was excreted into the feces. After IV dosing, the concentration of radioactivity in the kidney (cortex: 12,700 ng/g; medulla: 11,500 ng/g; pelvis: 11,300 ng/g) exceeded the blood concentration (1,570 ng/ml) 5 minutes post dose and at 24 hrs post dose (blood: 57.6 ng/ml; kidney cortex 318 ng/g; kidney medulla: 167 ng/g; kidney pelvis: 161 ng/g). Further, after oral dosing the $C_{max}$ in kidneys (cortex: 721 ng/g; medulla: 722 ng/g; pelvis: 1580 ng/g) exceeded the $C_{max}$ of blood (125 ng/ml) as did the $AUC_{inf}$ (blood: 3030 ng*h/ml; kidney cortex: 11,000 ng*h/ml; kidney medulla: 10,900 ng*h/ml; kidney pelvis: 10,500 ng*h/ml). The ratio of kidney concentrations to blood are greater for IV Compound 1 compared to oral Compound 1, indicating that there is a relationship between plasma and kidney/urine concentrations, which attain much higher and more rapid $C_{max}$ following IV dosing compared to oral dosing.

b) Human Pharmacokinetics $^{14}$C-labeled Compound 1 was administered as a single oral 300 mg dose to healthy human subjects. The plasma $C_{max}$ (563 ng/ml) and $AUC_{inf}$ (9418 ng*hr/ml) was consistent with previous oral dosing studies. The concentrations of Compound 1 in urine are shown in Table 2 and indicate that urine concentrations exceed the plasma concentrations throughout the dosing interval. The $AUC_{0-24}$ in urine was 186.1 µg*hr/ml.

TABLE 2

Human urine concentrations (single 300 mg oral dose)

| Time post Dose (hr) | Calculated Concentration (µg/ml) | | | | | | |
|---|---|---|---|---|---|---|---|
| | Subj5101 | Subj5102 | Subj5103 | Subj5104 | Subj5105 | Subj5106 | Mean |
| 0-4 | 11.82 | 18.38 | 8.13 | 5.48 | 19.21 | 4.32 | 11.22 |
| 4-8 | 5.12 | 13.88 | 22.13 | 3.83 | 7.19 | 6.55 | 9.78 |
| 8-12 | 6.28 | 10.61 | 10.62 | 4.76 | 9.0 | 4.42 | 7.62 |
| 12-24 | 5.95 | 9.65 | 23.40 | 7.27 | 5.78 | 5.93 | 9.66 |

If the urine concentrations in humans reflect the $C_{max}$ and plasma concentrations as shown in rats, the IV dose ($C_{max}$ approximately 1800 ng/ml after a single IV dose) and current dose regimen (loading dose) for Compound 1 is expected to result in higher urine concentrations, especially in the first segments of the dosing interval. The steady state AUC (IV and oral) and $C_{max}$ (oral) of Compound 1 is approximately 1.5× that of the single IV or oral dose which is likely to be reflected in both urine and kidney concentrations during the course of therapy. It is believed that Time>MIC is the driver for efficacy in UTI—thus, over the entire dosing interval, with a single oral dose, the urinary concentrations of Compound 1 exceed 4 µg/mL by a factor of approximately 2×. Thus, following multiple doses at steady-state, urinary concentrations of Compound 1 will approach concentrations that will be 3-4 times greater than 4 µg/mL. In addition, there is evidence that Compound 1 can exert anti-virulence factor effects at sub-inhibitory concentrations and for prolonged periods as drug dissipates after maximum exposure. Therefore, Compound 1 can interfere with biofilm production and adherence, motility, and cytotoxin production based on the ability to inhibit synthesis of necessary factors.

c) Microbiology

The in vitro activity of Compound 1 is indicated in Table 3. Previous studies indicated that the in vitro activity of Compound 1 is somewhat decreased by pH 6.0 in media. However, recent studies confirmed that the activity of Compound 1 against the urinary pathogens E. coli and S. saprophyticus was stable in urine relative to standard media. The pharmacodynamic driver of efficacy of Compound 1 in urine in the bladder is presumed to be Time>MIC. The time factor is expected to be in the range of 50% of the dosing interval. Thus, it is presumed MICs≤4 µg/mL would represent susceptible isolates based on the human urine concentrations and that this could possibly be greater if at steady-state urinary concentrations are greater than indicated in the single dose ADME study.

Data from a 2010 surveillance study of 4171 E. coli isolates, including isolates with ESBL+ and quinolone resistance phenotypes, demonstrates that >97% of the isolates have an MIC value <4 µg/mL (Table 3 below). This level of activity is particularly important for the empiric treatment of UTI since E. coli is by far the most common pathogen in this indication and oral therapy is important to allow discharge of the patient from the emergency room or hospital for treatment at home, as quickly as possible.

TABLE 3

Cumulative Inhibition by Compound 1 (Bold: Organisms of interest)

| Orgaism* | N | Cumulative % Inhibition at MIC (µg/ml) | | | | | | |
|---|---|---|---|---|---|---|---|---|
| | | ≤0.5 | 1 | 2 | 4 | 8 | 16 | ≥32 |
| MSSA | 5713 | 99.7 | 99.9 | 100 | | | | |
| MRSA | 4192 | 95.4 | 98.4 | 99.8 | 100 | | | |
| MSCoNS | 461 | 92.4 | 99.8 | 100 | | | | |
| MRCoNS | 1349 | 85.9 | 99.1 | 100 | | | | |
| E. faecalis VS | 2036 | 99.3 | 99.9 | 100 | | | | |
| E. faecalis VNS | 54 | 98.1 | 100 | | | | | |
| E. faecium VS | 575 | 99.8 | 100 | | | | | |
| E. Faecium VNS | 614 | 98.4 | 100 | | | | | |
| E. coli ESBL- | 3376 | 54.2 | 84.2 | 95.9 | 99.3 | 99.9 | 100 | 100 |
| E. coli ESBL- | 795 | 30.4 | 63.0 | 87.5 | 97.7 | 99.5 | 99.9 | 100 |
| E. coli FQS | 2906 | 58.5 | 87.0 | 96.6 | 99.6 | 99.9 | 99.9 | 100 |
| E. coli FQR | 1264 | 29.6 | 64.4 | 89.2 | 97.7 | 99.6 | 99.9 | 100 |
| K. pneumoniae ESBL- | 1381 | 2.4 | 29.1 | 79.9 | 92.1 | 95.6 | 98.3 | 100 |
| K. pneumoniae ESBL+ | 592 | 1.7 | 19.3 | 56.8 | 79.6 | 90.2 | 94.8 | 100 |
| K. pneumoniae FQS | 1561 | 2.4 | 29.6 | 79.3 | 92.5 | 95.9 | 98.5 | 100 |
| K. pneumoniae FQR | 412 | 1.2 | 15.3 | 48.8 | 72.6 | 86.7 | 92.7 | 100 |
| E. oxytoca | 377 | 2.1 | 57.6 | 89.4 | 95.2 | 98.7 | 99.7 | 100 |
| E. colacae CeftazS | 550 | 0.5 | 15.3 | 70.5 | 93.3 | 95.6 | 97.8 | 100 |
| E. colacae CeftazR | 254 | 0.4 | 7.9 | 54.3 | 81.9 | 90.2 | 94.1 | 100 |
| Citrobacter spp | 253 | 14.6 | 44.7 | 79.1 | 93.3 | 97.6 | 100 | |
| P. mirabilis | 384 | 0 | 0.3 | 1.3 | 5.7 | 22.9 | 56.8 | 100 |
| Ind+ Proteus spp | 258 | 0 | 0.8 | 3.1 | 26.0 | 58.1 | 73.3 | 100 |
| S. marcescens | 424 | 0 | 0.7 | 20.3 | 76.2 | 91.0 | 93.6 | 100 |

TABLE 3-continued

Cumulative Inhibition by Compound 1 (Bold: Organisms of interest)

| Orgaism* | N | ≤0.5 | 1 | 2 | 4 | 8 | 16 | ≥32 |
|---|---|---|---|---|---|---|---|---|
| | | | | Cumulative % Inhibition at MIC (µg/ml) | | | | |
| *Acinetobacter* | 952 | 31.1 | 44.1 | 73.1 | 93.5 | 98.5 | 99.5 | 100 |
| *P. aeruginosa*** | 22 | 0 | 0 | 0 | 0 | 0 | 9.1 | 100 |

*MS = Methicillin Susceptible; MR = Methicillin Resistant; CoNS = Coagulase-Negative *Staphylococcus*; VS = Vancomycin Susceptible; VNS = Vancomycin Non-Susceptible (including Vancomycin Resistant or VRE); ESBL = Extended-Spectrum β-lactamase phenotype; FQS = Fluoroquinolone Susceptible; FQR = Fluoroquinolone Resistant; CeftazS = Ceftazidime Susceptible; CeftazR = Ceftazidime Resistant
**Data from CMI 07

The 2008 CDC NHSN study from 2006-2008 summarizes the primary pathogens associated with catheter-associated UTI in hospital ICUs. As expected, *E. coli* is the predominant pathogen and gram-positive organism comprise a significant proportion of infections. Resistance rates to several important benchmark antibiotics are significant across all key pathogens and the situation today is likely to be worse. Table 4 summarizes the reported findings.

TABLE 4

Bacterial Pathogens in Catheter-Associated UTI* (Bold: key pathogens)

| Organism | % of isolates | Rank** | Resistance rates |
|---|---|---|---|
| CoNS | 2.5 | 7 | |
| *S. aureus* | 2.2 | 8 | 65.2% MRSA |
| *E. faecalis* | 3.6 | (3) | 6.1% VanR, 3.1AmpR |
| *E. faecium* | 6.0 | (3) | 81.0% VanR, 89.9% Amp |
| *E. coli* | 21.4 | 1 | 5.5% cephR (ESBL), 4.0% carbapenemR, 24.8% FQR |
| *P. aeruginosa* | 10.0 | 4 | |
| *K. pneumoniae* | 7.7 | 5 | 21.2% cephR (ESBL), 10.1% carbapenemR |
| Enterobacter spp | 4.1 | 6 | |
| Acinetobacter spp | 1.2 | 9 | 25.6% carbapenemR |
| *K. oxytoca* | 0.9 | 10 | 17.6% cephR (ESBL), 2.6% carbapenemR |

*Hidron, A. et al. 2008. Antimicrobial-Resistant Pathogens Associated With Healthcare-Associated Infections: Annual Summary of Data Reported to the National Healthcare Safety Network at the Centers for Disease Control and Prevention, 2006-2007. Infection Control and Hospital Epidemiology. November 2008, vol. 29, no. 11
**According to incidence. *Candida* spp ranked #2

The comparative in vitro activity of Compound 1 is shown in Table 5 for key organisms in UTI from the Sentry 2010 surveillance study. Resistance rates are high for ESBL Enterobacteriaceae for many drugs, including the fluoroquinolones (levofloxacin), older tetracyclines (doxycycline), and aminoglycosides (gentamicin).

TABLE 5

Activity of Compound 1 (Omadacycline) and comparator agents against key UTI organisms

| Organism | Drug | MIC90$^a$ by Region (% R*) | | | |
|---|---|---|---|---|---|
| | | N America | Europe | Asia/Pac | L. Amer |
| *E. coli* ESBL− | N | 1172 | 1533 | 282 | 389 |
| | Omadacycline | 2 | 2 | 2 | 2 |
| | Tigecycline | 0.25 (0) | 0.25 (0) | 0.25 (0) | 0.25 (0) |
| | Doxycycline | >8 (16) | >8 | >8 | >8(31.4) |
| | Cefepime | ≤0.12 (0) | ≤0.12 (0.1) | 1 (0) | ≤0.12 (0) |
| | Ceftriaxone | 0.12 (0) | 0.12 (0) | 0.12 (0) | 0.12 (0) |
| | Amox/clav | >8 | >8 (17.7) | >8 (14.2) | >8 |
| | Pip/tazo | 4 (0.9) | 4 (5.3) | 4 (2.5) | 4 (1.5) |
| | Imipenem | ≤0.12 (0) | ≤0.12 (0) | ≤0.12 (0) | ≤0.12 (0) |
| | Levofloxacin | >4 (21.9) | >4 (19.3) | >4 (17) | >4 (22.9) |
| | Amikacin | 4 (0) | 4 (0.3) | 4 (0.4) | 4 (0) |
| | Gentamicin | 2 (7.7) | 2 (7.4) | >8 (16.3) | 2 (9) |
| *E. coli* ESBL+ | N** | 134 (10.3%) | 274 (15.2%) | 219 (43.7%) | 168 (30.2%) |
| | Omadacycline | 4 | 4 | 2 | 4 |
| | Tigecycline | 0.25 (0) | 0.5 (0) | 0.25 (0) | 0.25 (0) |
| | Doxycycline | >8 (42.5) | >8 | >8 | >8 (53) |
| | Cefepime | >16 (38.8) | >16 (69) | >16 (73.5) | >16 (47) |
| | Ceftriaxone | >8 (85.8) | >8 (94.2) | >8 (99.5) | >8 (97.6) |
| | Amox/clav | >8 | >8 (70.1) | >8 (39.3) | >8 |
| | Pip/tazo | 64 (6) | >64 (24.1) | 16 (7.3) | 64 (7.7) |
| | Imipenem | 0.25 (0) | 0.25 (0) | 0.25 (0.5) | 0.25 (0.6) |
| | Levofloxacin | >4 (74.6) | >4 (79.2) | >4 (78.1) | >4 (81) |
| | Amikacin | 8 (0.7) | 8 (2.2) | 8 (8.2) | 8 (1.2) |
| | Gentamicin | >8 (26.1) | >8 (40.5) | >8 (58.9) | >8 (39.3) |

TABLE 5-continued

Activity of Compound 1 (Omadacycline) and comparator agents against key UTI organisms

| Organism | Drug | MIC90$^a$ by Region (% R*) | | | |
|---|---|---|---|---|---|
| | | N America | Europe | Asia/Pac | L. Amer |
| *K. pneumoniae* ESBL− | N | 671 | 361 | 189 | 160 |
| | Omadacycline | 4 | 4 | 4 | 4 |
| | Tigecycline | 0.5 (0) | 0.5 (0.3) | 0.5 (1.1) | 0.5 (0) |
| | Doxycycline | >8 (13.7) | >8 | >8 | >8 (17.5) |
| | Cefepime | ≤0.12 (0) | ≤0.12 (0) | ≤0.12 (0) | ≤0.12 (0) |
| | Ceftriaxone | 0.12 (0) | 0.12 (0) | 0.12 (0) | 0.12 (0) |
| | Amox/clav | 4 (0) | 8 (7.2) | 8 (3.7) | 8 |
| | Pip/tazo | 8 (0.7) | 8 (0) | 8 (2.1) | 4 (1.9) |
| | Imipenem | 0.25 (0) | 0.25 (0) | 0.5 (0) | 0.25 (0) |
| | Levofloxacin | ≤0.5 (1.9) | ≤0.5 (4.2) | 1 (5.3) | 1 (7.5) |
| | Amikacin | 2 (0) | 2 (0.3) | 2 (0.5) | 2 (0) |
| | Gentamicin | ≤1 (1.2) | ≤1 (2.2) | ≤1 (3.7) | ≤1 (1.3) |
| *K. pneumoniae* ESBL+ | N** | 108 (13.9%) | 151 (29.5%) | 124 (39.6%) | 209 (56.6%) |
| | Omadacycline | 16 | 8 | 16 | 16 |
| | Tigecycline | 2 (0) | 1 (0.7) | 1 (3.2) | 2 (0) |
| | Doxycycline | >8 (43.5) | >8 | >8 | >8 (44) |
| | Cefepime | >16 (43.5) | >16 (76.8) | >16 (65.3) | >16 (69.4) |
| | Ceftriaxone | >8 (95.4) | >8 (94.7) | >8 (93.5) | >8 (99.5) |
| | Amox/clav | >8 | >8 (84.1) | >8 (72.6) | >8 |
| | Pip/tazo | >64 (51.9) | >64 (57) | >64 (47.6) | >64 (51.7) |
| | Imipenem | >8 (26.9) | 2 (7.9) | >8 (10.5) | >8 (18.7) |
| | Levofloxacin | >4 (75) | >4 (66.9) | >4 (61.3) | >4 (67.9) |
| | Amikacin | 32 (2.8) | 32 (15.9) | >32 (23.4) | >32 (14.8) |
| | Gentamicin | >8 (46.3) | >8 (58.3) | >8 (58.1) | >8 (56.9) |
| *K. oxytoca* | N | 177 | 158 | 17 | 25 |
| | Omadacycline | 4 | 2 | 2 | 4 |
| | Tigecycline | 0.5 (0) | 0.5 (0) | 0.5 (5.9) | 1 (0) |
| | Doxycycline | 4 (2.3) | 2 | 2 | >8 (12) |
| | Cefepime | 0.25 (0) | 1 (4.4) | >16 (23.5) | >16 (16) |
| | Ceftriaxone | 4 (10.2) | >8 (17.7) | >8 (29.4) | >8 (40) |
| | Amox/clav | >8 | >8 (14.6) | >8 (23.5) | >8 |
| | Pip/tazo | 16 (7.9) | >64 (13.3) | 64 (17.6) | >64 (16) |
| | Imipenem | 0.25 (0.6) | 0.25 (0) | 0.5 (0) | 0.25 (4) |
| | Levofloxacin | ≤0.5 (1.7) | ≤0.5 (3.2) | ≤0.5 (0) | >4 (16) |
| | Amikacin | 2 (0) | 2 (0) | 2 (0) | 32 (8) |
| | Gentamicin | ≤1 (2.3) | ≤1 (8.2) | >8 (17.6) | >8 (12) |
| *E. cloacae* CeftazS | N | 210 | 183 | 100 | 57 |
| | Omadacycline | 4 | 4 | 4 | 8 |
| | Tigecycline | 0.5 (0) | 0.5 (0) | 0.5 (2) | 1 (0) |
| | Doxycycline | 4 (6.2) | 4 | >8 | >8 (12.3) |
| | Cefepime | ≤0.12 (0) | 0.25 (1.1) | ≤0.12 (2) | >16 (10.5) |
| | Ceftriaxone | 1 (3.3) | 2 (7.7) | 2 (5) | >8 (24.6) |
| | Amox/clav | >8 | >8 (92.3) | >8 (94) | >8 |
| | Pip/tazo | 4 (0.5) | 4 (1.1) | 4 (1) | 16 (3.5) |
| | Imipenem | 0.5 (0) | 0.5 (0) | 1 (1) | 0.5 (0) |
| | Levofloxacin | ≤0.5 (2.9) | ≤0.5 (2.2) | ≤0.5 (4) | >4 (12.3) |
| | Amikacin | 2 (0) | 2 (1.1) | 2 (1) | 16 (0) |
| | Gentamicin | ≤1 (0) | ≤1 (1.1) | ≤1 (6) | >8 (12.3) |
| *E. cloacae* CeftazR | N** | 77 (26.8%) | 72 (28.2%) | 63 (38.7%) | 42 (42.4%) |
| | Omadacycline | 16 | 8 | 8 | 4 |
| | Tigecycline | 2 (0) | 0.5 (0) | 0.5 (1.6) | 1 (0) |
| | Doxycycline | >8 (28.6) | >8 | 8 | >8 (14.3) |
| | Cefepime | 16 (6.5) | >16 (25) | >16 (38.1) | >16 (26.2) |
| | Ceftriaxone | >8 (100) | >8 (100) | >8 (100) | >8 (100) |
| | Amox/clav | >8 | >8 (100) | >8 (100) | >8 |
| | Pip/tazo | >64 (48.1) | >64 (62.5) | >64 (55.6) | >64 (23.8) |
| | Imipenem | 8 (11.7) | 1 (1.4) | 1 (0) | 0.5 (0) |
| | Levofloxacin | >4 (19.5) | >4 (22.2) | >4 (20.6) | >4 (31) |
| | Amikacin | 4 (0) | 8 (1.4) | 16 (9.5) | 16 (7.1) |
| | Gentamicin | >8 (20.8) | >8 (43.1) | >8 (39.7) | >8 (38.1) |
| *Enterobacter* spp | N | 101 | 82 | 52 | 42 |
| | Omadacycline | 4 | 4 | 16 | 4 |
| | Tigecycline | 0.5 (0) | 1 (1.2) | 1 (3.8) | 0.5 (0) |
| | Doxycycline | 4 (7.9) | 8 | >8 | 4 (0) |
| | Cefepime | 0.5 (1) | 1 (2.4) | 1 (5.8) | >16 (14.3) |
| | Ceftriaxone | >8 (24.8) | >8 (39) | >8 (30.8) | >8 (31) |
| | Amox/clav | >8 | >8 (91.5) | >8 (96.2) | >8 |
| | Pip/tazo | 64 (4) | 64 (32.9) | 32 (19.2) | 64 (7.1) |
| | Imipenem | 1 (1) | 1 (0) | 1 (0) | 1 (0) |
| | Levofloxacin | ≤0.5 (1) | 1 (73) | ≤0.5 (1.9) | 4 (9.5) |
| | Amikacin | 2 (1) | 4 (0) | 2 (3.8) | 4 (0) |
| | Gentamicin | ≤1 (1) | ≤1 (4.9) | ≤1 (7.7) | 2 (9.5) |

TABLE 5-continued

Activity of Compound 1 (Omadacycline) and comparator agents against key UTI organisms

| Organism | Drug | MIC90$^a$ by Region (% R*) | | | |
|---|---|---|---|---|---|
| | | N America | Europe | Asia/Pac | L. Amer |
| *A. baumanii* | N | 154 | 145 | 275 | 275 |
| | Omadacycline | 8 | 4 | 4 | 4 |
| | Tigecycline | 2 | 2 | 1 | 2 |
| | Doxycycline | >8 | >8 | >8 | >8 (15.3) |
| | Cefepime | >16 (61.7) | >16 | >16 | >16 (78.9) |
| | Ceftriaxone | >8 | >8 | >8 | >8 |
| | Amox/clav | >8 | >8 | >8 | >8 |
| | Pip/tazo | >64 (70.1) | >64 | >64 | >64 (88.7) |
| | Imipenem | >8 (53.2) | >8 (66.2) | >8 (72.4) | >8 (75.6) |
| | Levofloxacin | >4 (68.8) | >4 (74.5) | >4 (79.3) | >4 (86.9) |
| | Amikacin | >32 (42.9) | >32 (58.6) | >32 (74.9) | >32 (57.5) |
| | Gentamicin | >8 (57.8) | >8 (61.4) | >8 (80) | >8 (52.4) |
| *Acinetobacter* spp | N | 42 | 43 | 9 | 9 |
| | Omadacycline | 2 | 4 | 0.06-2 | 0.03-4 |
| | Tigecycline | 0.5 | 2 | ≤0.03-1 | ≤0.03-2 |
| | Doxycycline | >8 (11.9) | >8 | ≤0.06-2 | ≤0.06-2 (0) |
| | Cefepime | >16 (16.7) | >16 | 1->16 | 0.5->16 (55.6) |
| | Ceftriaxone | >8 (0) | >8 | 2->8 | 1->8 (0) |
| | Amox/clav | >8 | >8 | ≤1->8 | 2->8 |
| | Pip/tazo | >64 (19) | >64 | ≤0.5->64 | ≤0.5->64 (55.6) |
| | Imipenem | 8 (4.8) | >8 (30.2) | ≤0.12->8 (11.1) | ≤0.12->8 (44.4) |
| | Levofloxacin | >4 (14.3) | >4 (41.9) | ≤0.5->4 (11.1) | ≤0.5->4 (33.3) |
| | Amikacin | 8 (9.5) | >32 (39.5) | 0.5->32 (22.2) | 0.5->32 (22.2) |
| | Gentamicin | >8 (14.3) | >8 (32.6) | ≤1->8 (33.3) | ≤0.1->8 (22.2) |
| MSSA | N | 2373 | 2109 | 641 | 590 |
| | Omadacycline | 0.25 | 0.25 | 0.5 | 0.25 |
| | Tigecycline | 0.25 (0) | 0.25 (0) | 0.25 (0) | 0.25 (0) |
| | Doxycycline | 0.12 (≤0.1) | 0.12 (1.4) | 1 (1.7) | 0.5 (0) |
| | Ceftriaxone | 4 (0.1) | 4 (0) | 4 (0) | 4 (0) |
| | Amox/clav | ≤1 (0.1) | ≤1 (0) | ≤1 (0) | ≤(0) |
| | Pip/tazo | 2 (0.1) | 2 (0) | 2 (0) | 2 (0.2) |
| | Levofloxacin | 4 (10.8) | ≤0.5 (5.5) | ≤0.5 (5.9) | ≤0.5 (2.2) |
| | Gentamicin | ≤1 (0.7) | ≤1 (2.7) | ≤1 (8.4) | ≤1 (1.9) |
| | Vancomycin | 1 (0) | 1 (0) | 1 (0) | 1 (0) |
| MRSA | N** | 2508 (51.4%) | 750 (26.2%) | 428 (40.0%) | 506 (46.2%) |
| | Omadacycline | 0.5 | 0.25 | 1 | 0.25 |
| | Tigecycline | 0.25 (0) | 0.25 (0) | 0.25 (0) | 0.25 (0) |
| | Doxycycline | 0.5 (0.1) | 4 (10.8) | 8 (48.6) | 0.25 (0) |
| | Ceftriaxone | >8 (100) | >8 (100) | >8 (100) | >8 (100) |
| | Amox/clav | >8 (100) | >8 (100) | >8 (100) | >8 (100) |
| | Pip/tazo | 64 (100) | >64 (100) | >64 (100) | >64 (100) |
| | Levofloxacin | >4 (67.3) | >4 (86.4) | >4 (70.6) | >4 (84) |
| | Gentamicin | ≤1 (3.7) | >8 (23.1) | >8 (58.6) | >8 (35.4) |
| | Vancomycin | 1 (0) | 1 (0) | 1 (0) | 1 (0) |
| MS CoNS | N | 191 | 185 | 18 | 67 |
| | Omadacycline | 0.5 | 1 | 0.25 | 0.5 |
| | Tigecycline | 0.25 | 0.25 (0) | 0.25 (0) | 0.25 |
| | Doxycycline | 1 (0.5) | 1 (3.2) | 2 (5.6) | 2 (0) |
| | Ceftriaxone | 4 (0) | 4 (0) | 8 (0) | 4 (0) |
| | Amox/clav | ≤1 (0) | ≤1 (0) | ≤1 (0) | ≤1 (0) |
| | Pip/tazo | ≤0.5 (0) | ≤0.5 (0) | 1 (0) | 1 (0) |
| | Levofloxacin | >4 (23.6) | 2 (9.7) | >4 (16.7) | ≤0.5 (6) |
| | Gentamicin | ≤1 (2.1) | ≤1 (9.7) | 4 (33.3) | 8 (7.5) |
| | Vancomycin | 2 (0) | 2 (1.1) | 2 (0) | 2 (0) |
| MR CoNS | N** | 461 (70.7%) | 510 (73.4%) | 77 (81.1%) | 301 (81.8%) |
| | Omadacycline | 1 | 1 | 1 | 1 |
| | Tigecycline | 0.25 | 0.25 (0) | 0.25 (0) | 0.25 |
| | Doxycycline | 2 (1.3) | 2 (8.8) | 8 (20.8) | 1 (0.3) |
| | Ceftriaxone | >8 (100) | >8 (100) | >8 (100) | >8 (100) |
| | Amox/clav | 8 (100) | >8 (100) | >8 (100) | >8 (100) |
| | Pip/tazo | 16 (100) | >64 (100) | >64 (100) | >64 (100) |
| | Levofloxacin | >4 (64.9) | >4 (64.9) | >4 (55.8) | >4 (57.8) |
| | Gentamicin | >8 (22.6) | >8 (56.2) | >8 (72.7) | >8 (33.2) |
| | Vancomycin | 2 (0) | 2 (0.4) | 2 (1.3) | 2 (0) |
| *E. faecalis* VS | N | 863 | 669 | 214 | 290 |
| | Omadacycline | 0.5 | 0.25 | 0.5 | 0.25 |
| | Tigecycline | 0.25 (0) | 0.25 (0) | 0.25 (0) | 0.25 (0) |
| | Doxycycline | 8 (7.1) | >8 | >8 | 8 (7.6) |
| | Ceftriaxone | >8 | >8 | >8 | >8 |
| | Amox/clav | ≤1 (0) | ≤1 (0) | ≤1 (0) | ≤1 (0) |
| | Pip/tazo | 8 (0) | 8 (0) | 8 (0) | 8 (0) |
| | Levofloxacin | >4 (29.3) | >4 | >4 | >4 (30) |
| | Vancomycin | 2 (0) | 2 (0) | 2 (0) | 2 (0) |

TABLE 5-continued

Activity of Compound 1 (Omadacycline) and comparator agents against key UTI organisms

| Organism | Drug | MIC90ᵃ by Region (% R*) | | | |
|---|---|---|---|---|---|
| | | N America | Europe | Asia/Pac | L. Amer |
| *E. faecalis* VNS | N** | 38 (4.2%) | 8 (1.2%) | 1 (0.5%) | 7 (2.4%) |
| | Omadacycline | 0.25 | 0.06-0.5 | 0.5 | ≤0.015-0.06 |
| | Tigecycline | 0.25 (0) | ≤0.03-0.25 (0) | 0.25 | ≤0.03-0.06 (0) |
| | Doxycycline | 8 (5.3) | 0.5-8 | 8 | ≤0.06-4 (0) |
| | Ceftriaxone | >8 | >8 | >8 | >8 |
| | Amox/clav | ≤1 (0) | ≤1-2 (0) | ≤1 | ≤1-2 (0) |
| | Pip/tazo | 8 (0) | 4-16 (0) | 8 | 4-8 (0) |
| | Levofloxacin | >4 (97.4) | 1->4 | >4 | >4 (100) |
| | Vancomycin | >16 (92.1) | >16 (100) | >16 | >16 (100) |
| *E. faecium* VS | N | 115 | 303 | 106 | 51 |
| | Omadacycline | 0.25 | 0.12 | 0.25 | 0.12 |
| | Tigecycline | 0.25 (0) | 0.12 (0) | 0.12 (0) | 0.12 (0) |
| | Doxycycline | >8 (31.3) | >8 | >8 | >8 (21.6) |
| | Ceftriaxone | >8 | >8 | >8 | >8 |
| | Amox/clav | >8 | >8 (93.4) | >8 (91.5) | >8 |
| | Pip/tazo | >64 | >64 | >64 | >64 |
| | Levofloxacine | >4 (68.7) | >4 | >4 | >4 (78.4) |
| | Vancomycin | 1 (0) | 1 (0) | 1 (0) | 1 (0) |
| *E. faecium* VNS | N** | 478 (80.6%) | 71 (19.0%) | 24 (18.5%) | 41 (44.6%) |
| | Omadacycline | 0.25 | 0.25 | 0.25 | 0.12 |
| | Tigecycline | 0.25 (0) | 0.25 (0) | 0.25 (0) | 0.12 (0) |
| | Doxycycline | >8 (33.1) | 8 | >8 | 8 (7.3) |
| | Ceftriaxone | >8 | >8 | >8 | >8 |
| | Amox/clav | >8 | >8 (100) | >8 (100) | >8 |
| | Pip/tazo | >64 | >64 | >64 | >64 |
| | Levofloxacin | >4 (99.6) | >4 | >4 | >4 (100) |
| | Vancomycin | >16 (99.4) | >16 (100) | >16 (100) | >16 (100) |

ᵃwhen N <10, ranges of MICs are shown
*% Resistance based on CLSI breakpoints (N. America and Latin America) or Eucast breakpoints (Europe and Asia/Pacific)
**N ( ) = % of species with Resistant Phenotype.

The above data indicates that the in vitro activity of Compound 1 is sufficient for coverage of key UTI pathogens, especially factoring in the robust urinary and kidney concentrations achieved in humans (based on preliminary, single dose oral human studies). The rodent pharmacokinetic data provides more support and details on the urinary excretion and kidney concentrations expected in humans.

There are additional factors that may favorably impact the efficacy of Compound 1 in UTI treatment. Because Compound 1 inhibits protein synthesis, the ability of organisms to produce virulence factors may be compromised, including the ability to produce biofilm, adhere to biofilm, and ascend the urinary tract. Compound 1 has been shown to inhibit cytotoxin production even at sub-growth-inhibitory concentrations, indicating the Compound 1 has the ability to cause and sustain inhibition of protein synthesis beyond its impact on bacterial multiplication. The high tissue concentrations achieved in kidney tissue is expected to contribute to the treatment or prevention of ascending tissue infection including bacteremia.

Thus, the in vitro activity of Compound 1 and its pharmacokinetics in the urinary tract provide strong evidence that Compound 1 is effective to treat UTI as a first-line IV-to-oral or completely oral empiric monotherapy treatment option.

EXEMPLIFICATION OF THE INVENTION

Example 1 A Phase 1b Study to Evaluate the Safety and Pharmacokinetics (PK) of 9-[(2,2-dimethyl-propyl amino)-methyl-minocycline (Compound 1) in Female Adults with Cystitis Compound 1 is the first member of the aminomethylcycline class of antibiotics, which are semi-synthetic derivatives of the tetracycline class. Compound 1 has in vitro activity against the most common bacterial pathogens associated with cystitis, and has been shown to have a significant fraction of the administered dose excreted by the kidneys.

Compound 1 has in vitro activity against key urinary tract infection (UTI) pathogens, including extended spectrum beta-lactamase (ESBL)-producing *E. coli* that are resistant to multiple antibiotics. Preliminary single oral dose studies showed that robust urinary and kidney Compound 1 concentrations can be achieved in humans. The current study is designed to demonstrate the safety, pharmacokinetics, and efficacy of four multiple dose regimens of Compound 1 in the treatment of subjects with uncomplicated urinary tract infection (cystitis).

Thus, the primary objective of the study is to evaluate the urine and plasma concentrations of Compound 1 in female adult subjects with cystitis. The secondary objective of the study is to evaluate the safety of Compound 1 in the treatment of female adult subjects with cystitis. Additional secondary objectives may include: (1) evaluating the Microbiological Response and Clinical Response according to treatment group, or according to the dosing regimen; and, (2) evaluating the pharmacokinetic (PK) and pharmacodynamic (PD) relationship of Compound 1 in adult subjects with cystitis.

In addition, an exploratory objective of the study is to explore the potential clinical efficacy of Compound 1 in female adult subjects with cystitis.

According to the study design, a randomized (1:1:1), open-label, parallel designed Phase 1b study comparing 3 dosing regimens of Compound 1 (9-[(2,2-dimethyl-propyl amino)-methyl-minocycline) in the treatment of female adults with cystitis was conducted. About 31 female patients with uncomplicated urinary tract infection (cystitis) who met inclusion and exclusion criteria were enrolled at 2-4 U.S. treatment centers. All enrolled subjects participated in the study for approximately 5-6 weeks. Following Screening of up to 48 hrs, eligible subjects were randomly assigned to receive one of 3 dosing regimens of Compound 1 treatment as shown below. Subjects in all treatment groups were domiciled for a 5-day treatment period. Details of the study are further described below.

Rationale for Dose Regimen Selection:

This study was designed in accordance with the FDA Guidance for Industry: Uncomplicated Urinary Tract Infections—Developing Antimicrobial Drugs for Treatment (FDA, 1998).

In the Phase 1 studies, 536 subjects were exposed to Compound 1 IV or oral formulations. Single IV doses up to 600 mg and single oral doses up to 600 mg have been investigated. Multiple IV doses of 100 mg once daily and 200 mg once daily for up to 14 and 7 consecutive days, respectively, have been investigated. Multiple p.o. doses of 200 mg once daily and 300 mg once daily for up to 10 consecutive days have also been investigated without any serious adverse events. In all the Phase 1 studies, there were no discontinuations due to drug-related adverse events (AEs) in any subject who received multiple doses of Compound 1.

The half-life of Compound 1 is approximately 18 hours. This study included using a loading dose to achieve rapid steady-state conditions.

Uncomplicated UTIs are most commonly caused by $E.$ $coli$ and $Staphylococcus\ saprophyticus$ in 80% and 5-15% of cases, respectively (American Urological Association, www.auanet.org). The minimum inhibitory concentrations for at least 90% of the isolates ($MIC_{90}$) tested for Compound 1 against these common pathogens are 1 µg/mL for $S.$ $saprophyticus$, 2 µg/mL for ESBL-negative $E.\ coli$, and 4 µg/mL for ESBL-producing $E.\ coli$.

While the driver of efficacy for Compound 1 in UTI is not completely known, and while not wishing to be bound by any particular theory, Applicant believes that maximizing time of urine concentration above pathogen MIC (ideally, throughout the dosing interval) is desirable. This belief is partly based on a clinical study that evaluated the disposition of a single 300 mg oral dose of $^{14}$C-Compound 1. In this study, plasma concentrations were consistent with previous oral dosing studies (area under the concentration-time curve from 0 to infinity [$AUC_{0-inf}$] 9.4 µg·h/mL), and it was determined that approximately 40% of the absorbed dose was eliminated in the urine. Urine concentrations of Compound 1 were not measured directly but estimated concentrations (based on portion of excreted radioactivity) exceeded plasma concentrations and averaged between 7.6 and 11.2 µg/mL over the 24 hours following dosing. These urine concentrations would exceed the $MIC_{90}$ for ESBL-producing $E.\ coli$ (4 µg/mL) by approximately 2-fold. It is also known from Applicant's clinical studies that exposure to Compound 1 based on plasma concentrations is approximately 50% higher at steady-state than after a single dose. Therefore, Applicant expects that multiple doses of Compound 1 at 300 mg per oral dose will result in urine concentrations that are at least 3-fold greater than the $MIC_{90}$ for the common uncomplicated UTI pathogens.

Based on these predictions, and allowing for inter-subject variability, these data suggest that 300 mg is the lowest daily oral dose of Compound 1 that would maintain favorable urine concentrations to treat these pathogens. Thus 300 mg daily oral dose in two different regimens, both of which incorporate a "loading-dose" strategy on Day 1, should reach steady-state more rapidly.

Thus in some embodiments, one regimen provided an initial 200 mg IV dose of Compound 1 on Day 1, followed by once daily doses of 300 mg orally. It is known that a 300 mg dose of Compound 1 tablet is bioequivalent to a 100 mg IV dose; hence 200 mg IV is expected to be comparable to 600 mg orally. While increased incidence of GI AEs may be associated with oral doses of 400 mg or greater, it is expected that the 200 mg IV dose may be a better tolerated means of providing a rapid loading dose.

In related embodiments, another regimen provided two doses of 300 mg orally (separated by 12 hours) on Day 1, followed by once daily doses of 300 mg orally.

In contrast to uncomplicated UTI, complicated UTI (cUTI) can be caused by a wider variety of pathogens than uncomplicated UTI. While $E.\ coli$ remains the predominant pathogen, complicated UTI also can be associated with other aerobic Gram-negative bacteria (e.g., $Klebsiella$ or $Proteus$ spp.) or Gram-positive bacteria (e.g., $Enterococcus$ spp.). For some of these organisms, the $MIC_{90}$ for Compound 1 may be greater than 4 µg/mL. Therefore in some embodiments, a third dosing regimen provided a higher dose of Compound 1, with the goal of achieving greater urinary tract exposure. In this regimen, two oral doses of 450 mg (separated by 12 hours) were administered on Day 1, followed by once daily doses of 450 mg orally.

In addition, yet another regimen provides IV doses of about 100-200 mg of Compound 1. Each of the IV doses, administered about 24 hrs apart, may maintain the desired urine concentrations of Compound 1 above the $MIC_{90}$ for the UTI pathogens, particularly for cUTI. The first IV dose may be supplemented with a second IV dose (e.g., 100 mg) administered 12 hours after to provide a rapid rise of Compound 1 concentration in the first day of treatment.

Patient Inclusion/Exclusion Criteria

Enrolled patients were females of 18 years of age or older. Patients had onset of two or more of the following clinical signs and symptoms of a UTI within ≤72 hours prior to randomization: Dysuria, Frequency, Urgency, and Suprapubic pain. Patients were able to supply a mid-stream, clean catch urine sample for microbiological analysis. Patients had positive urine dipstick test for leukocyte esterase. In addition, all subjects had a negative pregnancy test at Screening, and agreed to comply with using a highly effective form of birth control (e.g., abstinence, p.o. contraceptive, intrauterine device [IUD], barrier contraception [condom], tubal ligation, hysterectomy, bilateral oophorectomy, or vasectomized partner) from Screening through post therapy evaluation (PTE).

Patients with any of the following conditions were not allowed in the trial: being male or pregnant or nursing (breastfeeding) woman; having received 1 or more doses of a systemic antibacterial treatment within the 48 hour period prior to randomization; having evidence of factors predisposing to the development of urinary tract infections, including renal calculi, stricture, primary renal disease (e.g., polycystic renal disease), neurogenic bladder, or other anatomic or functional abnormalities predisposing to urinary tract infection; having a temperature, flank pain, chills, or any other manifestations suggestive of upper urinary tract infection; having or is clinically suspected to have 1 or more of the following prior to randomization: alanine aminotransferase (ALT) or aspartate aminotransferase (AST) ≥3× Upper Limit of Normal (ULN), total bilirubin >1.5×ULN, or evidence of end-stage liver disease (e.g., ascites, hepatic encephalopathy); having a known history of having experienced unstable cardiac disease (e.g., unstable angina, myocardial infarction, congestive heart failure, cardiac arrhythmia, etc.) within the 3 months prior to Screening; requiring any form of dialysis (e.g., hemodialysis, peritoneal dialysis); having a history or evidence of severe renal disease or is known to have a calculated creatinine clearance (CrCl) of <30 mL/minute, using the Cockcroft-Gault equation; having evidence of significant immunological disease determined by any of the following: Current or anticipated neutropenia defined as <500 neutrophils/mm$^3$, Infection with Human Immunodeficiency Virus (HIV) and a cluster of differentiation 4 (CD4) count <200 cells/mm$^3$, or another Acquired Immune Deficiency Syndrome (AIDS)-defining illness, the receipt of cancer chemotherapy, radiotherapy, or potent, non-corticosteroid immunosuppressant drugs (e.g., cyclosporine, azathioprine, tacrolimus, immune-modulating monoclonal antibody therapy, etc.) within the past 3 months, or the receipt of corticosteroids equivalent to or greater than 40 mg of prednisone per day or for more than 14 days in the prior 30 days; having a history of hypersensitivity or allergic reaction (e.g., anaphylaxis, urticaria, other significant reaction) to any tetracycline (e.g., minocycline, doxycycline or tigecycline); having a history of pseudotumor cerebri, or prior (within 2 weeks prior to Screening) or planned concomitant use of isotretinoin; having a history of systemic lupus erythematosus or lupus-like syndrome; having current evidence of pancreatitis; using other investigational drugs within 5 half-lives or 30 days prior to Screening, whichever is longer; having previously been treated with Compound 1 or previously enrolled in this study; having any planned medical intervention that might interfere with the ability to comply with the study requirements or impact the interpretation of the data; and having any concomitant condition that, in the opinion of the investigator, is likely to interfere with evaluation of the response of the infection under study, determination of adverse events (AEs), or completion of the expected course of treatment.

Cockcroft-Gault equation to calculate creatinine clearance (CrCl) (relevant to Exclusion criterion above) is:

$$\frac{(140 - age[yrs]) * weight[kg] * (Z)}{Cr[mg/dL] * 72}$$

$Z = 1.0$, if Male $Z = 0.85$, if Female

Corticosteroid conversions (relevant to Exclusion criterion above) were done according to the following table:

| The following have equivalent glucocorticoid activity | |
| --- | --- |
| Hydrocortisone | 160 mg |
| Prednisone | 40 mg |
| Prednisolone | 40 mg |
| Methylprednisolone | 32 mg |
| Triamcinolone | 32 mg |
| Dexamethasone | 6 mg |

Dosing Regimens

Subjects were randomized (1:1:1) to one of the following treatment arms:
1. Group 1: IV load, p.o. daily (200 mg Compound 1 IV every 24 hours (q24h) for 1 dose, followed by 300 mg p.o. q24h for a total of 5 days);
2. Group 2: p.o. load, p.o. daily (300 mg Compound 1 p.o. every 12 hours (q12h) for 2 doses, followed by 300 mg p.o. q24h for a total of 5 days);
3. Group 3: high p.o. load, high p.o. daily (450 mg Compound 1 p.o. q12h for 2 doses, followed by 450 mg p.o. q24h for a total of 5 days).

Representative dosing schedules are provided in the table below:

| Dose time | Study Day | Group 1$^{a,b}$ OMC iv load, po daily | Group 2$^b$ OMC po load, po daily | Group 3$^c$ OMC High po load, High po daily |
| --- | --- | --- | --- | --- |
| t = 0 h | 1 | 200 mg iv | 300 mg po | 450 mg po |
| t = 12 h | 1 | — | 300 mg po | 450 mg po |
| t = 24 h | 2 | 300 mg po | 300 mg po | 450 mg po |
| t = 48 h | 3 | 300 mg po | 300 mg po | 450 mg po |
| t = 72 h | 4 | 300 mg po | 300 mg po | 450 mg po |
| t = 96 h | 5 | 300 mg po | 300 mg po | 450 mg po | h = hours;

iv = intravenous;

OMC = Compound 1;

po = oral;

t = time;

— = no dose is given at the specified time.

$^a$The 200 mg iv dose of Compound 1 was administered as a 110 mL continuous infusion over 30 minutes (at least 30 minutes and not more than 45 minutes).

$^b$300 mg p.o. doses of Compound 1 were administered as 2 × 150 mg tablets with water in a fasted state (no food or drink except water for at least 6 hours prior to dosing).

$^c$450 mg p.o. doses of Compound 1 were administered as 3 × 150 mg tablets with water in a fasted state (no food or drink except water for at least 6 hours prior to dosing).

During the treatment period, serial blood and urine samples were collected for safety analysis, microbiological analysis and for pharmacokinetic (PK) analysis of Compound 1. Safety assessments included monitoring of adverse events (AEs), clinical laboratory test results, vital sign measurements, 12-lead electrocardiogram (ECG) results, pregnancy testing and physical examination findings.

Subjects were confined to the clinical site from the day treatment begins (Day 1) until the PK and safety assessments at the End of Treatment (EOT) evaluation are completed (Day 6). Subjects returned to the clinical site for a Post Therapy Evaluation (PTE) within 5 to 9 days after the last dose of test article. A Final Follow-up visit (Final Follow-up) was conducted within 30 to 37 days following the first dose of test article.

Patient demographics based on treatment groups is presented below.

| | 200 mg IV, 300 mg po (n = 11) | 300 mg po (n = 10) | 450 mg po (n = 10) | All Subjects (n = 31) |
| --- | --- | --- | --- | --- |
| Subjects, n Female | 11 | 10 | 10 | 31 |
| Age, years Median (range) | 51 (20-60) | 31 (25-54) | 41 (19-75) | 38 (19-75) |
| Weight, kg Median (range) | 72 (47-95) | 75 (54-121) | 69 (51-111) | 72 (47-121) |
| BMI, kg/m$^2$ Median (range) | 27 (20-39) | 28 (20-43) | 27 (21-41) | 27 (20-43) |

Patient disposition data for the first 31 patients enrolled in the study is presented below.

| uUTI Patient Disposition | | | | |
|---|---|---|---|---|
| | IV_PO300 n (%) | PO300 n (%) | PO450 n (%) | Total n (%) |
| Patients screened | | | | 72 |
| Patients Randomized | 11 | 10 | 10 | 31 |
| Study Populations | | | | |
| Safety, N [1] | 11 | 10 | 10 | 31 |
| PK | 11 (100.0) | 10 (100.0) | 10 (100.0) | 31 (100.0) |
| Study Treatment Completion Status | | | | |
| Completed Study Treatment | 10 (90.9) | 10 (100.0) | 10 (100.0) | 30 (96.8) |
| Prematurely Discontinued Study Treatment | 1 (9.1) | 0 (0.0) | 0 (0.0) | 1 (3.2) |
| Reason for Premature Discontinuation of Study Drug | | | | |
| Subject withdrew consent | 1 (9.1) | 0 (0.0) | 0 (0.0) | 1 (3.2) |
| Number of Subjects Completing the Study through the PTE Visit | 10 (90.9) | 7 (70.0) | 10 (100.0) | 27 (87.1) |
| Number of Subjects Not Completing the Study through the PTE Visit | 1 (9.1) | 3 (30.0) | 0 (0.0) | 4 (12.9) |
| Reason for Premature Discontinuation from Study | | | | |
| Lost to follow-up | 0 (0.0) | 3 (30.0) | 0 (0.0) | 3 (9.7) |
| Other: Subject no longer wanted to participate in PKs and study confinement. | 1 (9.1) | 0 (0.0) | 0 (0.0) | 1 (3.2) |

N = number of subjects in the Safety Population.
n = number of subjects in the specific category.
Percentages are calculated as 100 × (n/N).
[1] Safety population is presented by treatment actually received.

Drug Administration

Compound 1 was administered intravenously (IV) or orally. The total duration of treatment (IV and/or oral) was 5 days.

Compound 1 for infusion was formulated with tosylate acid counter ion, sucrose, hydrochloric acid, and sodium hydroxide to adjust the pH. Compound 1 oral tablet was formulated with lactose monohydrate, microcrystalline cellulose, sodium stearyl fumarate, crospovidone, colloidal silicone dioxide, sodium bisulfite, polyvinyl alcohol, titanium dioxide, talc, glycerol monocaprylocaprate, sodium lauryl sulfate, and iron oxide yellow.

For IV administration, sterile, lyophilized Compound 1 powder for reconstitution was packaged in a clear, glass vial with a rubber stopper and aluminum overseal. The labeled content of the vial was 100 mg of Compound 1 base. There was a 4% overfill to allow for the extraction of a 100 mg dose. Each vial was reconstituted into a clear solution by adding 5 mL Sterile Water for Injection. The vial was swirled gently to ensure complete dissolution prior to use, as excessive shaking would lead to foaming in the vial. Reconstituted vials were used immediately to prepare the infusion solution. The 200 mg infusion solution was prepared by withdrawing 5 mL of reconstituted solution from each of two 100 mg vials and slowly injecting into a 100 mL Normal Saline (NS) for injection (0.9% sodium chloride) infusion bag. The prepared infusion solution was used within 8 hours or stored at up to 24 hours at 2 to 8° C. (35.6 to 46.4° F.). The 110 mL infusion solution was administered at room temperature continuously over 30 minutes (at least 30 minutes and not more than 45 minutes).

For oral administration, Compound 1 150 mg tablets were taken fasting as 2 (300 mg oral dose) or 3 (450 mg oral dose) tablets with water q12h (first day only) or q24 h (subsequent days). The tablets were taken with water in a fasting state (no food, antacids or multivitamins containing multivalent cations [e.g., aluminum, magnesium, calcium, bismuth, iron, or zinc], or drink except water for at least 6 hours). After dosing, no food was consumed for 2 hours; no dairy products, antacids or multivitamins containing multivalent cations (e.g., aluminum, magnesium, calcium, bismuth, iron, or zinc) for 4 hours.

Pharmacokinetic Variables:

Blood Collection: (Plasma)

Blood samples were collected and analyzed for Compound 1 concentration at the following times. Pre-dose blood PK evaluations were based on blood samples collected within 10 min of each start (e.g., t=0 h dose for Day 1, t=24 h dose for Day 2, etc.).

Day 1: Pre-dose, and 0.75, 1, 2, 3, 4, 6, 8 and 12 hours after the t=0 h dose (12 h sample before the t=12 h dose for Groups 2 and 3);

Day 2: prior to the t=24 h dose;

Day 3: prior to the t=48 h dose;

Day 4: prior to the t=72 h dose;

Day 5: Pre-dose, and 0.5, 1, 2, 3, 4, 6, 8 and 12 hours after the t=96 h dose

Day 6: at t=120 h (24 hours after the t=96 h dose on Day 5)

Figure 8A:
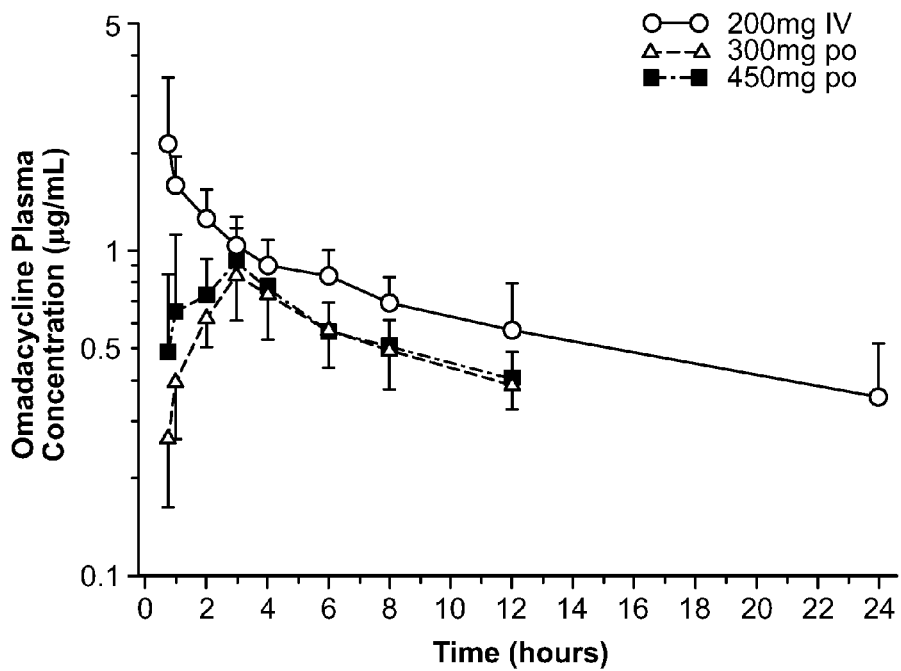
FIGS. 8A (Day 1) and 8B (Day 5) show the mean concentration-time profiles of three dose levels of Compound 1 (Omadacycline) in plasma for the first batch of 31 enrolled uUTI patients.
Figure 8B:
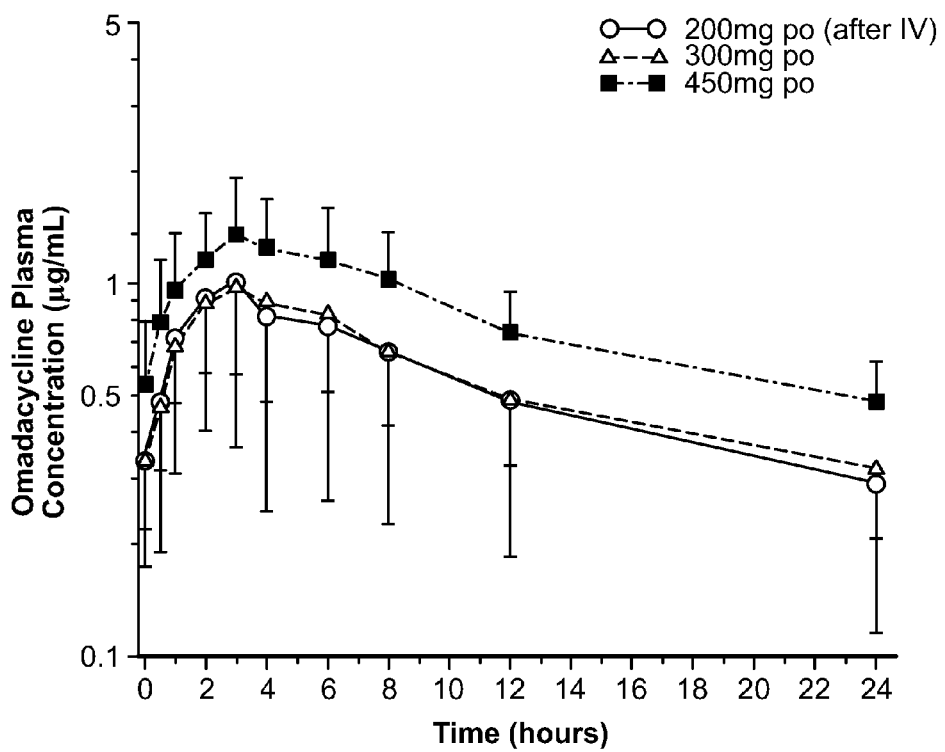

FIGS. 8A and 8B show the Compound 1 plasma concentration-time profile at Day 1 and Day 5, respectively, for the first 31 enrolled uUTI patients at three dose levels.

Compound 1 plasma concentration-time data following the initial dose on Day 1 was used to determine maximum plasma concentration ($C_{max}$), time to reach $C_{max}$ ($T_{max}$), area under the concentration-time curve (AUC), area under the plasma (or serum or blood) concentration-time curve from time 0 to time 't' where t is a defined time point after administration ($AUC_{0-t}$), area under the concentration time curve from 0 to 24 hours ($AUC_{0-24}$) (Group 1) and area under the concentration-time curve from 0 to 12 hours ($AUC_{0-12}$) (Groups 2 and 3). In addition, the area under the concentration-time curve from 0 to infinity ($AUC_{0-inf}$), terminal elimination half-life ($T_{1/2}$), elimination rate constant ($\lambda_z$), systemic clearance (CL) and apparent volume of dis tribution (Vd) of Compound 1 were estimated for Group 1, only, following the intravenous dose on Day 1. Following the final oral doses on Day 5 the Compound 1 plasma concentration-time data for Groups 1, 2 and 3 were used to determine $C_{max}$, $T_{max}$, $AUC_{24h}$, $AUC_t$. Trough plasma concentrations ($C_{trough}$) following each dose (Days 2 to 6) were also determined.

The above measured descriptive statistics for blood plasma pharmacokinetic (PK) parameters from the PK population are summarized in the tables below.

| Descriptive Statistics for Blood Plasma Pharmacokinetic Parameters PK Population | | | | | |
|---|---|---|---|---|---|
| Parameter (unit) | Visit | | IV_PO300 (N = 11) | PO300 (N = 10) | PO450 (N = 10) |
| AUC(0-inf) (h * ng/mL) | Day 1 | n | 10 | NA | NA |
| | | Mean | 19888.14 | NA | NA |
| | | Geo. Mean | 19684.30 | NA | NA |
| | | SD | 3003.124 | NA | NA |
| | | Median | 19291.16 | NA | NA |
| | | Min, Max | 15613.4, 24419.0 | NA, NA | NA, NA |
| AUC(0-12 hrs) (h * ng/mL) | Day 1 | n | NA | 10 | 10 |
| | | Mean | NA | 6261.25 | 6846.67 |
| | | Geo. Mean | NA | 6151.68 | 6685.93 |
| | | SD | NA | 1181.407 | 1591.226 |
| | | Median | NA | 6518.09 | 6650.70 |
| | | Min, Max | NA, NA | 4047.1, 8216.4 | 4373.9, 10217.7 |
| AUC(0-24 hrs) (h * ng/mL) | Day 1 | n | 11 | NA | NA |
| | | Mean | 16021.10 | NA | NA |
| | | Geo. Mean | 15557.41 | NA | NA |
| | | SD | 4592.780 | NA | NA |
| | | Median | 14817.92 | NA | NA |
| | | Min, Max | 11331.5, 28673.3 | NA, NA | NA, NA |
| | Day 5 | n | 10 | 10 | 10 |
| | | Mean | 13156.42 | 13500.56 | 19829.34 |
| | | Geo. Mean | 9554.75 | 12374.85 | 18692.72 |
| | | SD | 7855.695 | 4548.367 | 6114.900 |
| | | Median | 15803.09 | 13440.50 | 21649.63 |
| | | Min, Max | 1716.2, 23612.9 | 3119.5, 19331.1 | 7143.8, 28198.2 |
| Clearance (mL/h) | Day 1 | n | 10 | NA | NA |
| | | Mean | 10.27 | NA | NA |
| | | Geo. Mean | 10.16 | NA | NA |
| | | SD | 1.553 | NA | NA |
| | | Median | 10.37 | NA | NA |
| | | Min, Max | 8.2, 12.8 | NA, NA | NA, NA |
| Cmax (ng/mL) | Day 1 | n | 11 | 10 | 10 |
| | | Mean | 2158.18 | 876.90 | 987.40 |
| | | Geo. Mean | 1957.91 | 848.85 | 947.77 |
| | | SD | 1273.765 | 224.891 | 302.241 |
| | | Median | 1850.00 | 916.50 | 947.00 |
| | | Min, Max | 1300.0, 5840.0 | 495.0, 1230.0 | 484.0, 1710.0 |
| | Day 5 | n | 10 | 10 | 10 |
| | | Mean | 1117.20 | 1116.00 | 1487.10 |
| | | Geo. Mean | 808.50 | 998.90 | 1359.36 |
| | | SD | 657.403 | 415.315 | 537.974 |
| | | Median | 1300.00 | 1070.00 | 1645.00 |
| | | Min, Max | 121.0, 1830.0 | 207.0, 1690.0 | 378.0, 2380.0 |
| Ctrough (ng/mL) | Day 5 | n | 10 | 10 | 10 |
| | | Mean | 292.05 | 319.16 | 483.60 |
| | | Geo. Mean | 213.71 | 292.97 | 462.41 |
| | | SD | 176.433 | 112.857 | 133.656 |
| | | Median | 378.00 | 315.00 | 503.00 |
| | | Min, Max | 34.6, 467.0 | 81.6, 476.0 | 211.0, 655.0 |
| Lambda Z (1/h) | Day 1 | n | 10 | NA | NA |
| | | Mean | 0.0620 | NA | NA |
| | | Geo. Mean | 0.0614 | NA | NA |
| | | SD | 0.00910 | NA | NA |
| | | Median | 0.0605 | NA | NA |
| | | Min, Max | 0.049, 0.082 | NA, NA | NA, NA |
| | Day 5 | n | 7 | NA | NA |
| | | Mean | 0.0545 | NA | NA |
| | | Geo. Mean | 0.0526 | NA | NA |
| | | SD | 0.01460 | NA | NA |
| | | Median | 0.0574 | NA | NA |
| | | Min, Max | 0.029, 0.077 | NA, NA | NA, NA |
| T½ (h) | Day 1 | n | 10 | NA | NA |
| | | Mean | 11.38 | NA | NA |
| | | Geo. Mean | 11.29 | NA | NA |
| | | SD | 1.543 | NA | NA |
| | | Median | 11.46 | NA | NA |
| | | Min, Max | 8.5, 14.2 | NA, NA | NA, NA |

Descriptive Statistics for Blood Plasma Pharmacokinetic Parameters PK Population

| Parameter (unit) | Visit | | IV_PO300 (N = 11) | PO300 (N = 10) | PO450 (N = 10) |
|---|---|---|---|---|---|
| | Day 5 | n | 7 | NA | NA |
| | | Mean | 13.75 | NA | NA |
| | | Geo. Mean | 13.18 | NA | NA |
| | | SD | 4.733 | NA | NA |
| | | Median | 12.08 | NA | NA |
| | | Min, Max | 9.0, 23.6 | NA, NA | NA, NA |
| $T_{max}$ (h) | Day 1 | n | 11 | 10 | 10 |
| | | Mean | 0.897 | 2.992 | 2.492 |
| | | Geo. Mean | 0.869 | 2.957 | 2.207 |
| | | SD | 0.2667 | 0.4721 | 1.0862 |
| | | Median | 0.750 | 3.000 | 3.000 |
| | | Min, Max | 0.72, 1.60 | 2.00, 4.00 | 0.97, 4.00 |
| | Day 5 | n | 10 | 10 | 10 |
| | | Mean | 2.600 | 3.900 | 3.363 |
| | | Geo. Mean | 2.829 | 3.607 | 2.638 |
| | | SD | 1.0785 | 1.7920 | 2.2337 |
| | | Median | 3.000 | 3.000 | 3.017 |
| | | Min, Max | 0.00, 4.00 | 2.00, 8.00 | 0.50, 8.00 |
| Volume Distribution (mL) | Day 1 | n | 10 | NA | NA |
| | | Mean | 167.57 | NA | NA |
| | | Geo. Mean | 165.43 | NA | NA |
| | | SD | 29.438 | NA | NA |
| | | Median | 158.86 | NA | NA |
| | | Min, Max | 140.5, 231.4 | NA, NA | NA, NA |

NA: Not Applicable; N=Number of subjects in the PK Population. n=Number of subjects in the specific category. Parameter day and group measurements: Lambda, half life: d1, d5 for IV_PO300; $AUC_{0-inf}$, Clearance, Volume Distribution: d1 for IV_PO300; $AUC_{0-12}$: d1 for PO300, PO450; $AUC_{0-24}$, $AUC_{0-\tau}$: d1, d5 for IV_PO300 and d5 for PO300 and PO450; $C_{max}$, $T_{max}$: d1, d5 for all 3 groups.

Representative Compound 1 plasma PK parameters are summarized below.

| Parameter (unit) | 200 mg IV, 300 mg po (n = 11) | 300 mg po (n = 10) | 450 mg po (n = 10) |
|---|---|---|---|
| Day 1 | | | |
| $C_{max}$ (μg/mL) | 2.16 | 0.88 | 0.99 |
| | (59.0) | (25.6) | (30.6) |
| $t_{max}$ (h)[a] | 0.75 | 3.0 | 3.0 |
| | (0.72, 1.60) | (2.0, 4.0) | (0.97, 4.0) |
| $AUC_{0-24}$ | 16.02 | ND | ND |
| (μg · h/mL) | (28.7) | | |
| $AUC_{0-12}$ | ND | 6.26 | 6.85 |
| (μg · h/mL) | | (18.9) | (23.2) |
| Day 5 | | | |
| $C_{max}$ (μg/mL) | 1.12 | 1.12 | 1.49 |
| | (58.8) | (37.2) | (36.2) |
| $t_{max}$ (h)[a] | 3.0 | 3.0 | 3.0 |
| | (0.0, 4.0) | (2.0, 8.0) | (0.50, 4.0) |
| $AUC_{0-24}$ | 13.16 | 13.50 | 19.83 |
| (μg · h/mL) | (59.7) | (33.7) | (30.8) |
| $C_{min}$ (μg/mL) | 0.29 | 0.32 | 0.48 |
| | (60.4) | (35.4) | (27.6) |

Mean (% CV);

[a]median (maximum, minimum);

ND, not determined.

Urine Collection

Figure 9:
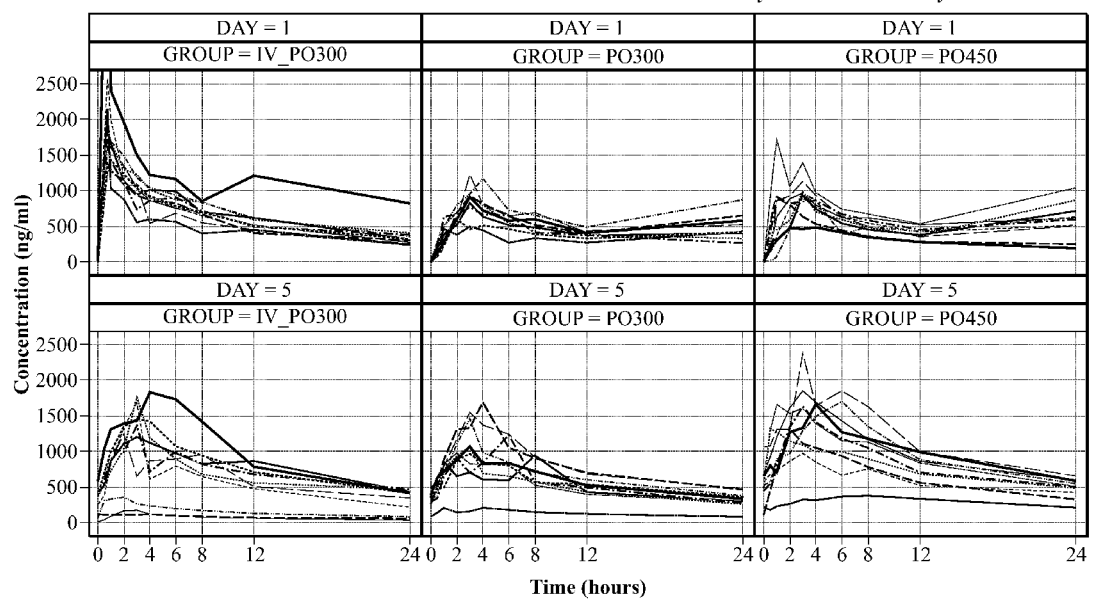
FIG. 9 shows overlaid individual urine concentration-time profiles by treatment and day.

Urine was collected, the volume recorded, and analyzed for Compound 1 concentration at the following times:

Day 1 to 2: pooled total urine 0 to 4, 4 to 8, 8 to 12, and 12-24 hours after the t=0 h dose; Collection of the 12 to 24 h sample should be completed prior to the t=24 h dose on Day 2;

Day 5 to 6: pooled total urine 0 to 4, 4 to 8, 8 to 12, and 12-24 hours after the t=96 h dose;

Urine was pooled during the intervals above. At the end of each interval, the time and total volume were recorded. FIG. 9 shows overlaid individual urine concentration-time profiles by treatment and day.

The urine concentration data is summarized in the table below.

Descriptive statistics for urine pharmacokinetic parameters in the PK population is also shown below.

Compound 1 urine concentration data was used to determine the amount excreted in a dosing interval, the urinary excretion rate, and, in conjunction with the plasma concentration data, to estimate the renal clearance (CLr) of Compound 1.

| Summary of PK Urine Concentration and Volume Data in the PK Population | | | | | | | |
|---|---|---|---|---|---|---|---|
| | | IV_PO300 (N = 11) | | PO300 (N = 10) | | PO450 (N = 10) | |
| Visit/Time Point | | Concentration (ng/mL) | Volume (mL) | Concentration (ng/mL) | Volume (mL) | Concentration (ng/mL) | Volume (mL) |
| Day 1, 0-4 hour Post t = 0 | n | 9 | 11 | 10 | 10 | 10 | 10 |
| | Mean | 65360.0 | 347.9 | 14003.0 | 718.5 | 23008.0 | 423.1 |
| | SD | 53017.50 | 544.10 | 9694.07 | 617.73 | 29939.60 | 256.07 |
| | Median | 55000.0 | 143.8 | 14020.0 | 605.1 | 10500.0 | 317.5 |
| | Min, Max | 9840, 160000 | 0, 1900 | 2740, 27300 | 225, 2350 | 1030, 96500 | 39, 800 |
| Day 1, 4-8 hour Post t = 0 | n | 11 | 11 | 9 | 10 | 9 | 10 |
| | Mean | 43548.2 | 355.5 | 19088.9 | 423.9 | 20537.8 | 454.8 |
| | SD | 31524.32 | 382.49 | 9470.01 | 359.36 | 19190.66 | 369.56 |
| | Median | 40900.0 | 194.5 | 16800.0 | 294.0 | 15500.0 | 300.0 |
| | Min, Max | 7530, 99200 | 49, 1375 | 6030, 33200 | 0, 1250 | 3750, 64900 | 0, 1250 |
| Day 1, 8-12 hour Post t = 0 | n | 11 | 11 | 10 | 10 | 10 | 10 |
| | Mean | 32407.3 | 320.4 | 19981.0 | 631.6 | 11699.0 | 586.2 |
| | SD | 20320.69 | 310.68 | 19234.25 | 468.16 | 6815.15 | 334.55 |
| | Median | 33700.0 | 225.4 | 13650.0 | 444.5 | 8995.0 | 597.5 |
| | Min, Max | 7480, 72100 | 31, 1037 | 4880, 67900 | 152, 1575 | 2710, 25300 | 100, 1050 |
| Day 1-2, 12-24 hour Post t = 0 | n | 11 | 11 | 10 | 10 | 10 | 10 |
| | Mean | 22410.0 | 745.1 | 20772.0 | 918.2 | 25713.0 | 802.6 |
| | SD | 17751.79 | 297.49 | 11921.70 | 313.30 | 16235.73 | 530.35 |
| | Median | 19300.0 | 734.4 | 21300.0 | 900.0 | 19550.0 | 614.0 |
| | Min, Max | 7770, 71800 | 375, 1155 | 3320, 39600 | 306, 1350 | 6430, 50100 | 400, 2100 |
| Day 5, 0-4 hour Post t = 96 | n | 10 | 10 | 10 | 10 | 9 | 10 |
| | Mean | 42710.0 | 240.7 | 30900.0 | 332.2 | 35988.9 | 371.7 |
| | SD | 43368.24 | 191.82 | 18898.27 | 186.28 | 24124.23 | 314.80 |
| | Median | 26250.0 | 190.1 | 26850.0 | 362.5 | 25700.0 | 302.3 |
| | Min, Max | 4260, 138000 | 17, 620 | 11100, 76100 | 66, 600 | 10300, 76900 | 0, 931 |
| Day 5, 4-8 hour Post t = 96 | n | 9 | 10 | 9 | 10 | 10 | 10 |
| | Mean | 26090.0 | 265.7 | 29111.1 | 378.6 | 48117.0 | 466.4 |
| | SD | 18061.07 | 185.79 | 21373.37 | 197.67 | 46012.99 | 384.25 |
| | Median | 28500.0 | 226.0 | 18200.0 | 396.2 | 33700.0 | 350.0 |
| | Min, Max | 6760, 59000 | 0, 629 | 10800, 67000 | 0, 675 | 9470, 149000 | 68, 1329 |
| Day 5, 8-12 hour Post t = 96 | n | 10 | 10 | 10 | 10 | 10 | 10 |
| | Mean | 33237.0 | 305.0 | 25350.0 | 287.6 | 30466.0 | 360.9 |
| | SD | 34554.98 | 295.36 | 16990.93 | 183.29 | 25839.81 | 278.45 |
| | Median | 14850.0 | 172.7 | 19600.0 | 253.6 | 20600.0 | 225.0 |
| | Min, Max | 5120, 90100 | 60, 900 | 12300, 68600 | 70, 575 | 9000, 83500 | 100, 850 |
| Day 5-6, 12-24 hour Post t = 96 | n | 10 | 10 | 10 | 10 | 9 | 9 |
| | Mean | 21480.0 | 648.5 | 17940.0 | 777.2 | 30280.0 | 845.7 |
| | SD | 21969.65 | 308.69 | 11998.73 | 358.17 | 23567.00 | 455.89 |
| | Median | 12590.0 | 581.0 | 16000.0 | 650.0 | 23400.0 | 916.9 |
| | Min, Max | 2390, 70400 | 250, 1187 | 5040, 46900 | 375, 1400 | 4200, 61200 | 300, 1500 |

| Descriptive statistics for urine pharmacokinetic parameters in the PK population | | | | | |
|---|---|---|---|---|---|
| Parameter (unit) | | Visit | IV_PO300 (N = 11) | PO300 (N = 10) | PO450 (N = 10) |
| Ae 0-24 hrs (mg) | Day 1 | n | 11 | 10 | 10 |
| | | Mean | 40.70 | 39.24 | 35.95 |
| | | Geo. Mean | 36.98 | 36.94 | 34.07 |
| | | SD | 17.768 | 13.349 | 11.704 |
| | | Median | 41.40 | 39.07 | 37.30 |
| | | Min, Max | 18.6, 64.2 | 18.6, 56.8 | 18.5, 51.5 |
| | Day 5 | n | 10 | 10 | 10 |
| | | Mean | 32.27 | 38.21 | 54.87 |
| | | Geo. Mean | 21.72 | 31.46 | 43.60 |
| | | SD | 25.395 | 19.838 | 36.567 |
| | | Median | 31.29 | 34.96 | 50.26 |
| | | Min, Max | 5.1, 84.0 | 5.3, 66.1 | 7.6, 140.2 |
| Ae 0-4 hrs (mg) | Day 1 | n | 9 | 10 | 10 |
| | | Mean | 13.80 | 6.41 | 7.27 |
| | | Geo. Mean | 11.59 | 5.90 | 3.96 |
| | | SD | 8.171 | 2.654 | 7.391 |
| | | Median | 9.74 | 6.58 | 5.05 |
| | | Min, Max | 4.0, 27.0 | 2.9, 11.3 | 0.3, 24.1 |

-continued

| Descriptive statistics for urine pharmacokinetic parameters in the PK population ||||||
|---|---|---|---|---|---|
| Parameter (unit) | | Visit | IV_PO300 (N = 11) | PO300 (N = 10) | PO450 (N = 10) |
| | Day 5 | n | 10 | 10 | 9 |
| | | Mean | 7.74 | 10.02 | 12.07 |
| | | Geo. Mean | 3.89 | 7.20 | 9.50 |
| | | SD | 10.077 | 6.728 | 6.185 |
| | | Median | 4.99 | 9.35 | 11.76 |
| | | Min, Max | 0.4, 34.5 | 1.1, 24.1 | 1.0, 20.0 |
| Ae 4-8 hrs (mg) | Day 1 | n | 11 | 9 | 9 |
| | | Mean | 8.61 | 7.60 | 7.11 |
| | | Geo. Mean | 7.28 | 6.42 | 6.00 |
| | | SD | 4.900 | 5.223 | 4.520 |
| | | Median | 7.96 | 6.28 | 6.16 |
| | | Min, Max | 1.3, 20.9 | 2.8, 19.9 | 2.4, 16.2 |
| | Day 5 | n | 9 | 9 | 10 |
| | | Mean | 8.38 | 10.54 | 19.74 |
| | | Geo. Mean | 5.22 | 9.17 | 11.02 |
| | | SD | 7.077 | 6.356 | 25.898 |
| | | Median | 7.13 | 8.05 | 10.30 |
| | | Min, Max | 1.2, 18.8 | 4.8, 22.4 | 2.7, 88.3 |
| Ae 8-12 hrs (mg) | Day 1 | n | 11 | 10 | 10 |
| | | Mean | 6.80 | 9.17 | 5.36 |
| | | Geo. Mean | 5.53 | 7.22 | 4.75 |
| | | SD | 4.134 | 6.697 | 2.887 |
| | | Median | 6.17 | 6.86 | 5.27 |
| | | Min, Max | 1.6, 13.3 | 2.0, 22.1 | 2.5, 11.8 |
| | Day 5 | n | 10 | 10 | 10 |
| | | Mean | 6.28 | 6.74 | 7.54 |
| | | Geo. Mean | 3.94 | 5.02 | 6.01 |
| | | SD | 4.315 | 4.440 | 4.892 |
| | | Median | 6.47 | 7.29 | 5.62 |
| | | Min, Max | 0.3, 12.2 | 1.1, 13.7 | 1.4, 16.7 |
| Ae 12-24 hrs (mg) | Day 1 | n | 11 | 10 | 10 |
| | | Mean | 14.00 | 16.82 | 16.92 |
| | | Geo. Mean | 12.70 | 14.19 | 14.57 |
| | | SD | 6.556 | 8.968 | 9.029 |
| | | Median | 12.32 | 16.30 | 15.98 |
| | | Min, Max | 6.4, 26.9 | 4.0, 28.4 | 4.4, 32.9 |
| | Day 5 | n | 10 | 10 | 9 |
| | | Mean | 10.71 | 11.95 | 18.59 |
| | | Geo. Mean | 7.31 | 10.71 | 15.26 |
| | | SD | 7.743 | 5.361 | 8.775 |
| | | Median | 11.25 | 11.38 | 20.23 |
| | | Min, Max | 1.1, 22.2 | 3.1, 23.5 | 2.6, 29.1 |
| Fe 0-24 hrs (%) | Day 1 | n | 11 | 10 | 10 |
| | | Mean | 20.35 | 6.54 | 3.99 |
| | | Geo. Mean | 18.49 | 6.16 | 3.79 |
| | | SD | 8.884 | 2.225 | 1.300 |
| | | Median | 20.70 | 6.51 | 4.14 |
| | | Min, Max | 9.3, 32.1 | 3.1, 9.5 | 2.1, 5.7 |
| | Day 5 | n | 10 | 10 | 10 |
| | | Mean | 10.76 | 12.74 | 12.19 |
| | | Geo. Mean | 7.24 | 10.49 | 9.69 |
| | | SD | 8.465 | 6.613 | 8.126 |
| | | Median | 10.43 | 11.65 | 11.17 |
| | | Min, Max | 1.7, 28.0 | 1.8, 22.0 | 1.7, 31.1 |
| Renal CL (L/h) | Day 1 | n | 11 | NA | NA |
| | | Mean | 2.296 | NA | NA |
| | | Geo. Mean | 1.982 | NA | NA |
| | | SD | 1.3455 | NA | NA |
| | | Median | 1.629 | NA | NA |
| | | Min, Max | 0.82, 5.08 | NA, NA | NA, NA |
| | Day 5 | n | 10 | 10 | 10 |
| | | Mean | 5.674 | 4.693 | 1.743 |
| | | Geo. Mean | 3.778 | 3.442 | 1.291 |
| | | SD | 6.1520 | 4.7999 | 1.1979 |
| | | Median | 2.642 | 3.513 | 1.665 |
| | | Min, Max | 1.50, 19.87 | 1.18, 17.73 | 0.19, 3.57 |

N = Number of subjects in the PK Population.
n = Number of subjects in the specific category.

Representative Compound 1 urine PK parameters are summarized below.

| Parameter (unit) | 200 mg IV, 300 mg po (n = 11) | 300 mg po (n = 10) | 450 mg po (n = 10) |
|---|---|---|---|
| Day 1 | | | |
| $Ae_{0-24}$ (mg) | 40.70 (44) | 39.24 (34) | 35.95 (33) |
| Total dose within 24 hrs, (mg) | 200 IV | 600 po | 900 po |
| $fe_{0-24}$ (%) [dose administered] | 20.4 | 6.5 | 4.0 |
| $fe_{0-24}$ (%) [dose absorbed] | 20.4 | 18.7 | 11.4 |
| Day 5 | | | |
| $Ae_{0-24}$ (mg) | 32.27 (79) | 38.21 (52) | 54.87 (67) |
| Total dose within 24 hrs, (mg) | 300 po | 300 po | 450 po |
| $fe_{0-24}$ (%) [dose administered] | 10.8 | 12.7 | 12.2 |
| $fe_{0-24}$ (%) [dose absorbed] | 30.7 | 36.4 | 34.8 |

Ae, amount excreted in urine;
fe, fraction of dose excreted in urine;
Mean, (% CV).

The data provides important information on the magnitude of plasma and urine concentrations of Compound 1 following administration of 3 dosage regimens to female adult subjects with cystitis. The mean fraction of dose excreted in urine, based on the dose absorbed ranged between 11.4% and 20.4% on Day 1, and between 30.7% and 36.4% on Day 5 of therapy with the 3 dosage regimens. The in vitro activity against common urinary pathogens and the sustained urine concentrations for 24 hours suggest that Compound 1 can be a useful antibacterial agent for the treatment of lower urinary tract bacterial infections caused by susceptible pathogens.

Safety Evaluation

Safety evaluations of the enrolled subjects included physical exams, vital signs (blood pressure, pulse rate, body temperature), AEs and SAEs, laboratory assessments (hematology, serum chemistry, urinalysis), 12-lead electrocardiogram (ECG) evaluations, concomitant medications, and pregnancy assessments.

All screening evaluations were completed within the 48 hours prior to randomization. The subject demographic and baseline characteristic data were collected at screening. These include: Demography, physical examination, vital signs, 12-lead ECG, hematology, serum chemistry and serum pregnancy test (all subjects). Relevant medical history and current medical conditions including data until signing of the ICF were recorded. The subject's assessment of UTI signs and symptoms severity on a 4 point scale (absent, mild, moderate, severe) were recorded. A clean-catch, midstream urine sample was collected and immediately sent to the local microbiology laboratory for urine dipstick leukocyte esterase test and microscopic examination and culture.

At screening, physical examination included the examination of general appearance, skin, neck (including thyroid), eyes, ears, nose, throat, lungs, heart, abdomen, back, lymph nodes, extremities, and vascular and neurological systems. If indicated based on medical history and/or symptoms, rectal, external genitalia, breast, and/or pelvic exams were performed.

Information for all physical examinations was included in the source documentation at the study site. Significant findings that were present prior to the start of test article were included in the subject's eCRF. Relevant findings that were present prior to the start of test article were included in the relevant medical history/current medical conditions screen on the subject's eCRF. Significant findings made after the start of test article which meet the definition of an AE were recorded on the Adverse Event screen of the subject's eCRF.

Vital signs including blood pressure (BP), pulse rate, and body temperature were collected at the following time points: Screening, Day 1, Day 3, End of Treatment (EOT), Post Therapy Evaluation (PTE). BP and pulse rate were measured within 30 min prior to and approximately (±15 minutes) 1 hour and 3 hours after the completion of each dose on Day 1 and Day 3 (t=0 h dose, t=12 h dose if applicable, and t=48 h dose).

Single 12-lead ECGs were obtained after the subject had been in the supine position for at least 5 minutes at the following time points: Screening and EOT, and as otherwise clinically indicated. Measurements of the following parameters were reported: heart rate, RR interval, PR interval, QRS duration, QT interval, QTc, and QTcF. In addition, the investigator determined whether the ECG was normal, abnormal not clinically significant, or abnormal clinically significant. For any abnormal ECG a description of the abnormalities was recorded. The investigator consulted with a cardiologist on a case-by-case basis, if needed, to discuss abnormal results.

Blood was collected from all subjects for a serum β-hCG pregnancy test at the Central Laboratory at the Screening, EOT and PTE visits. A subject's AEs and SAEs were recorded and reported from signing of the ICF to the Final Follow-Up assessment. If Screening blood cultures were positive for a potential pathogen, blood cultures were repeated as necessary until negative cultures were obtained. A clean-catch, mid-stream urine specimen was collected at screening, daily while on treatment, and at EOT and PTE visits, and immediately sent to the local microbiology laboratory for microscopic examination and culture. Quantitative urine culture by appropriate methods was performed using a calibrated loop that would identify bacteria at a lower limit of $10^3$ CFU/mL. WBC counts in the urine were determined by microscopy from spun or unspun urine or dipstick analysis for leukocyte esterase.

Efficacy Evaluation

Efficacy evaluation includes microbiological assessment of the infection; subject assessment of UTI signs and symptoms severity on a 4 point scale (absent, mild, moderate, severe, based on Clayson et al., *BJU International* 96:350-359, 2005); and investigator's assessment of clinical response defined as resolution of signs and symptoms of the infection to the extent that further antibacterial therapy is not necessary.

a) Microbiological Assessments

Blood Culture

Two sets of blood cultures (first set=1 aerobic bottle+1 anaerobic bottle, second set=2 aerobic bottles) were collected at Screening. Each set of blood cultures was collected by direct venipuncture from independent body sites 15-30 minutes apart. If bacteria were isolated from baseline blood cultures, repeat blood cultures were collected on the day that the positive blood culture was detected. If subsequent blood cultures were also positive, the blood cultures were repeated as necessary until negative blood cultures were obtained. Blood culture isolates were sent to the Central Laboratory.

Urine Culture

At screening and at all study visits (i.e., screening, daily while on treatment, and at EOT and PTE visits) a microbiologic evaluation of the infection under study was performed.

A clean-catch midstream urine sample was collected and immediately sent to the local microbiology laboratory for microscopic examination and culture.

A clean-catch midstream urine sample was collected at the following times to avoid disruption of the collection of total urine for PK.

All bacterial isolates identified by the local laboratory from urine or blood culture, were submitted to the Central Laboratory for verification of genus and species and for standardized minimum inhibitory concentration (MIC) testing performed for Compound 1 and a panel of currently approved antibiotics.

The investigator used the culture and susceptibility results from the local microbiology laboratory to help guide therapy.

Results from the baseline microbiological assessment and pathogens from baseline culture in the safety population are listed below.

| Baseline Microbiological Assessment and Pathogens from Baseline Culture in Safety Population | | | | | |
|---|---|---|---|---|---|
| | | IV_PO300 (N = 11) | PO300 (N = 10) | PO450 (N = 10) | Total (N = 31) |
| Subjects with Organism Growth at Baseline | n (%) | 8 (72.7) | 9 (90.0) | 10 (100.0) | 27 (87.1) |
| Subjects with No Organism Growth at Baseline | n (%) | 3 (27.3) | 1 (10.0) | 0 (0.0) | 4 (12.9) |
| Number of unique ORGANISMS Grown Among Growth Subjects | Mean | 1.1 | 2.0 | 1.4 | 1.5 |
| | SD | 0.35 | 1.41 | 0.52 | 0.94 |
| | Median | 1.0 | 1.0 | 1.0 | 1.0 |
| | Min, Max | 1, 2 | 1, 5 | 1, 2 | 1, 5 |
| Subjects with Pathogen Growth at Baseline, N1 | n (%) | 6 (54.5) | 5 (50.0) | 7 (70.0) | 18 (58.1) |
| Subjects with No Pathogen Growth at Baseline | n (%) | 5 (45.5) | 5 (50.0) | 3 (30.0) | 13 (41.9) |
| Number of unique PATHOGENS Grown Among Growth Subjects | Mean | 1.2 | 1.2 | 1.1 | 1.2 |
| | SD | 0.41 | 0.45 | 0.38 | 0.38 |
| | Median | 1.0 | 1.0 | 1.0 | 1.0 |
| | Min, Max | 1, 2 | 1, 2 | 1, 2 | 1, 2 |
| Subjects with Gram Negative PATHOGENS [1] | n (%) | 6 (100.0) | 4 (80.0) | 6 (85.7) | 16 (88.9) |
| Escherichia coli | n (%) | 3 (50.0) | 3 (60.0) | 4 (57.1) | 10 (55.6) |
| Klebsiella pneumoniae | n (%) | 0 (0.0) | 1 (20.0) | 2 (28.6) | 3 (16.7) |
| Proteus mirabilis | n (%) | 3 (50.0) | 1 (20.0) | 0 (0.0) | 4 (22.2) |
| Subjects with Gram Positive PATHOGENS [1] | n (%) | 1 (16.7) | 1 (20.0) | 2 (28.6) | 4 (22.2) |
| Aerococcus urinae | n (%) | 0 (0.0) | 0 (0.0) | 1 (14.3) | 1 (5.6) |
| Enterococcus faecalis | n (%) | 1 (16.7) | 0 (0.0) | 0 (0.0) | 1 (5.6) |
| Staphylococcus saprophyticus | n (%) | 0 (0.0) | 0 (0.0) | 1 (14.3) | 1 (5.6) |
| Streptococcus agalactiae - (Group B) | n (%) | 0 (0.0) | 1 (20.0) | 0 (0.0) | 1 (5.6) |

Min = Minimum;
Max = Maximum;
SD = Standard Deviation.
N = Number of subjects in the Safety Population.
n = Number of subjects in the specific category. Subjects with the same organism/pathogen from more than one specimen are counted only once for that pathogen. Baseline organisms/pathogens are growth cultures that occurred prior to first dose of study drug.
[1] = Percentages are calculated as 100 × (n/N1).

Day 1—prior to the first test article dose (t=0 h)
Day 2—after the 12 to 24 hour total urine collection post t=0 h dose has concluded
Day 3—any time
Day 4—any time
Day 5—prior to the test article dose (t=96 h)
Day 6—after the 12 to 24 hour total urine collection post t=96 h dose has concluded Urine samples were analyzed for pyuria microscopically (white blood cell [WBC] count >10/μL in unspun urine or ≥10 per high power field in spun urine) or by urine dipstick test for leukocyte esterase. At screening a urine dipstick test for leukocyte esterase was done per Inclusion Criterion.

Quantitative urine culture by appropriate methods was performed using a calibrated loop that would identify bacteria at a lower limit of $1 \times 10^3$ CFU/mL. In general, bacteria identified at $1 \times 10^5$ colony forming units (CFU)/mL or greater were considered a bacterial pathogen (probability of true pathogen was greater than probability of contamination). In addition, if the same bacteria was isolated in the blood and in the urine at any CFU count it was considered a pathogen. Culture results were to include identification of all pathogens to the level of genus and species. In vitro antimicrobial susceptibility testing of the isolates to antimicrobial drugs that may be used to treat UTIs was performed locally using a standard method chosen by the laboratory.

b) Investigator's Assessment of Clinical Response
Investigator's Assessment of Clinical Response at EOT The EOT visit was conducted on Day 6. This evaluation was also conducted for any prematurely withdrawn subject. The following assessments were performed at the EOT visit: subject assessment of UTI signs and symptoms severity, urine culture and leukocyte esterase dipstick test or microscopic examination, physical examination, vital signs, 12-lead ECG, hematology and serum chemistry, serum pregnancy test (all subjects) and investigator's assessment of clinical response. Subjects, who discontinued study treatment before completing the study, and those who prematurely withdrew from the study for any reason, were scheduled for a visit as soon as possible, at which time all of the assessments listed for the EOT visit were performed.

It was determined whether the subject met the criteria of 1 of the following clinical outcomes:
Clinical Success: Resolution of signs and symptoms at the EOT visit and no use of additional antimicrobial therapy.
Clinical Failure: No apparent response to therapy, persistence of signs and symptoms of infection at the EOT visit, or use of additional antimicrobial therapy for the current infection.
Indeterminate: EOT visit not completed.

Investigator's Assessment of Clinical Response at PTE

The PTE visit was conducted 5 to 9 days after the subject's last day of therapy. This evaluation was also conducted for any prematurely withdrawn subject. The following assessments were performed at the PTE visit: urine culture and leukocyte esterase dipstick test or microscopic examination, physical examination, vital signs, hematology, serum chemistry, serum pregnancy test (all subjects), and investigator's assessment of clinical response.

It was determined whether the subject met the criteria of 1 of the following clinical outcomes:

Clinical Success: Resolution of signs and symptoms at the PTE visit and no use of additional antimicrobial therapy.

Clinical Failure: No apparent response to therapy, persistence of signs and symptoms of infection, or reappearance of signs and symptoms at or before the PTE visit, or use of additional antimicrobial therapy for the current infection.

Indeterminate: PTE visit not completed.

A Final Follow-up visit was conducted 30 to 37 days after the subject's first dose of test article. This evaluation was also conducted for any prematurely withdrawn subject. The Final Follow-up assessment were conducted via telephone contact or by another interactive technology for subjects who were considered to be Clinical Successes and had no AEs or clinically significant laboratory or ECG abnormalities noted at or after the PTE visit. Otherwise, the visit must be conducted in person.

The results of clinical success rate in the different groups are summarized below.

The table below summarizes results for per-pathogen microbiological response at the PTE (post-therapy evaluation) visit in safety population with a baseline pathogen.

| Per-Pathogen Microbiological Response at the PTE Visit in Safety Population with a Baseline Pathogen | | | |
|---|---|---|---|
| | IV_PO300 (N = 6) n (%) | PO300 (N = 5) n (%) | PO450 (N = 7) n (%) |
| Overall Gram Negative Pathogens, N1 | 6 | 4 | 6 |
| Eradication | 6 (100.0) | 4 (100.0) | 3 (50.0) |
| Indeterminate | 0 (0.0) | 0 (0.0) | 0 (0.0) |
| Persistence | 0 (0.0) | 1 (25.0) | 3 (50.0) |
| Gram Negative Pathogens | | | |
| *Escherichia coli*, N1 | 3 | 3 | 4 |
| Eradication | 3 (100.0) | 2 (66.7) | 2 (50.0) |
| Indeterminate | 0 (0.0) | 0 (0.0) | 0 (0.0) |
| Persistence | 0 (0.0) | 1 (33.3) | 2 (50.0) |
| *Klebsiella pneumoniae*, N1 | 0 | 1 | 2 |
| Eradication | NA (NA) | 1 (100.0) | 1 (50.0) |
| Indeterminate | NA (NA) | 0 (0.0) | 0 (0.0) |
| Persistence | NA (NA) | 0 (0.0) | 1 (50.0) |
| *Proteus mirabilis*, N1 | 3 | 1 | 0 |
| Eradication | 3 (100.0) | 1 (100.0) | NA (NA) |
| Indeterminate | 0 (0.0) | 0 (0.0) | NA (NA) |
| Persistence | 0 (0.0) | 0 (0.0) | NA (NA) |
| Overall Gram Positive Pathogens, N1 | 1 | 1 | 2 |
| Eradication | 1 (100.0) | 1 (100.0) | 2 (100.0) |
| Indeterminate | 0 (0.0) | 0 (0.0) | 0 (0.0) |
| Persistence | 0 (0.0) | 0 (0.0) | 0 (0.0) |
| Gram Positive Pathogens | | | |
| *Aerococcus urinae*, N1 | 0 | 0 | 1 |
| Eradication | NA (NA) | NA (NA) | 1 (100.0) |
| Indeterminate | NA (NA) | NA (NA) | 0 (0.0) |
| Persistence | NA (NA) | NA (NA) | 0 (0.0) |
| *Enterococcus faecalis*, N1 | 1 | 0 | 0 |

| Investigator Assessment of Clinical Response in Safety Population | | | | |
|---|---|---|---|---|
| Visit | Investigator Assessment/Reasons for Failure | IV_PO300 (N = 11) n (%) | PO300 (N = 10) n (%) | PO450 (N = 10) n (%) |
| EOT | All Subjects [1] | 11 (100.0) | 10 (100.0) | 10 (100.0) |
| | Clinical Success | 10 (90.9) | 10 (100.0) | 9 (90.0) |
| | Clinical Failure, N1 | 0 (0.0) | 0 (0.0) | 1 (10.0) |
| | Indeterminate | 1 (9.1) | 0 (0.0) | 0 (0.0) |
| | Reasons for Clinical Failure [2] | 0 (0.0) | 0 (0.0) | 1 (100.0) |
| | Persistence of signs and symptoms of infection at or before current visit | 0 (0.0) | 0 (0.0) | 1 (100.0) |
| PTE | All Subjects [1] | 11 (100.0) | 9 (90.0) | 10 (100.0) |
| | Clinical Success | 11 (100.0) | 7 (70.0) | 8 (80.0) |
| | Clinical Failure, N2 | 0 (0.0) | 2 (20.0) | 2 (20.0) |
| | Indeterminate | 0 (0.0) | 0 (0.0) | 0 (0.0) |
| | Reasons for Clinical Failure [3] | 0 (0.0) | 2 (100.0) | 2 (100.0) |
| | Persistence of signs and symptoms of infection at or before current visit | 0 (0.0) | 2 (100.0) | 1 (50.0) |
| | Use of additional systemic antimicrobial therapy for the current infection | 0 (0.0) | 0 (0.0) | 1 (50.0) |

N = number of subjects in the safety population.
n = number of subjects in the specific category.
N1 = number of subjects in indicated categories.

-continued

Per-Pathogen Microbiological Response at the PTE Visit in
Safety Population with a Baseline Pathogen

| | IV_PO300 (N = 6) n (%) | PO300 (N = 5) n (%) | PO450 (N = 7) n (%) |
|---|---|---|---|
| Eradication | 1 (100.0) | NA (NA) | NA (NA) |
| Indeterminate | 0 (0.0) | NA (NA) | NA (NA) |
| Persistence | 0 (0.0) | NA (NA) | NA (NA) |
| *Staphylococcus saprophyticus*, N1 | 0 | 0 | 1 |
| Eradication | NA (NA) | NA (NA) | 1 (100.0) |
| Indeterminate | NA (NA) | NA (NA) | 0 (0.0) |
| Persistence | NA (NA) | NA (NA) | 0 (0.0) |
| *Streptococcus agalactiae* - (Group B), N1 | 0 | 1 | 0 |
| Eradication | NA (NA) | 1 (100.0) | NA (NA) |
| Indeterminate | NA (NA) | 0 (0.0) | NA (NA) |
| Persistence | NA (NA) | 0 (0.0) | NA (NA) |

PTE = post-therapy evaluation.
N = Number of subjects in the Safety Population with a baseline pathogen.
n = Number of subjects in the specific category. Percentages are calculated as 100 × (n/N1).
N1 = Number of subjects in category.

c) Pharmacokinetic Assessments

The permitted windows for PK sample collection are as follows:

| | Window |
|---|---|
| PK blood collection-scheduled time relative to test article dose | |
| Day 1 - Predose (t = 0 h) | Within 10 minutes prior to dose |
| Day 1 - 0.75 to 1 hour | ±2 minutes |
| Day 1 - 1.5 hours to 8 hours | ±5 minutes |
| Day 1 - 12 hours | ±15 minutes (for Groups 2 and 3 collect prior to the t = 12 h dose) |
| Day 2 - Predose (t = 24 h) | Within 10 minutes prior to dose |
| Day 3 - Predose (t = 48 h) | Within 10 minutes prior to dose |
| Day 4 - Predose (t = 72 h) | Within 10 minutes prior to dose |
| Day 5 - Predose (t = 96 h) | Within 10 minutes prior to dose |
| Day 5 - 0.5 to 1 hour (after the t = 96 h dose) | ±2 minutes |
| Day 5 - 1.5 hours to 8 hours (after the t = 96 h dose) | ±5 minutes |
| Day 5 - 12 hours (after the t = 96 h dose) | ±15 minutes |
| Day 6 - 24 hours (after the t = 96 h dose) | ±15 minutes |
| Urine | |
| Scheduled time period | Total post dose urine collected at the specified time windows with the exact times recorded |

PK = pharmacokinetics.

PK Blood Collection and Processing

Blood samples for PK are collected at the time points specified below.

Day 1: Predose, and 0.75, 1, 2, 3, 4, 6, 8 and 12 hours after the t=0 h dose (12 h sample before the t=12 h dose for Groups 2 and 3);
Day 2: prior to the t=24 h dose;
Day 3: prior to the t=48 h dose;
Day 4: prior to the t=72 h dose;
Day 5: Predose, and 0.5, 1, 2, 3, 4, 6, 8 and 12 hours after the t=96 h dose
Day 6: at t=120 h (24 hours after the t=96 h dose on Day 5)

Blood was collected either by fresh venipuncture or via a cannula used solely for that purpose. The dates and times for all doses of test article and PK sample collections were recorded. For intravenously administered doses of test article, the start and stop times for each infusion were recorded. Immediately after the sample was collected, the tube was gently inverted 5 to 8 times to thoroughly mix the anticoagulant and then placed upright in a cryoblock or test tube rack surrounded by ice until centrifugation. Samples were centrifuged at 1500×g for 10 minutes at approximately 4° C. within 30 minutes of collection. The resultant plasma was divided into 2 equal aliquots, placed in individual cryovials, and immediately frozen at −20° C. or colder within 1 hour of collection. The samples were kept frozen at −20° C. or colder pending shipment to the bioanalytical laboratory.

PK Urine Collection and Processing

Urine was collected and the volume recorded at the following times:

Day 1 to 2: pooled total urine 0 to 4, 4 to 8, 8 to 12, and 12-24 hours after the t=0 h dose;
Day 5 to 6: pooled total urine 0 to 4, 4 to 8, 8 to 12, and 12-24 hours after the t=96 h dose;

At the end of each collection time period the pooled urine was frozen at −20° C. or colder and the total volume of urine collected for the time period was recorded. The samples were kept frozen at −20° C. or colder pending shipment to the bioanalytical laboratory.

d) Adverse Events Assessments

An AE is any untoward, undesired, or unplanned event in the form of signs, symptoms, disease, or laboratory or physiologic observations occurring in a person given a test article in a clinical study. The event does not need to be causally related to the test article or clinical study. An AE includes, but is not limited to, the following:

Any clinically significant worsening of a preexisting condition;
An AE occurring from overdose of a test article, whether accidental or intentional. Overdose is a dose greater than that specified in the protocol;
An AE occurring from abuse (e.g., use for nonclinical reasons) of a test article;
An AE that has been associated with the discontinuation of the use of a test article.

An SAE is an AE that:
Results in death;
Is life threatening (see below);
Requires hospitalization or prolongation of an existing hospitalization (see below);
Results in a persistent or significant disability or incapacity (see below);
Results in cancer;
Results in a congenital anomaly or birth defect;
Additionally, important medical events that may not result in death, be life threatening, or require hospitalization may be considered SAEs when, based on appropriate medical judgment, they may jeopardize the subject and may require medical or surgical intervention to prevent 1 of the outcomes listed in this definition. Examples of such events include allergic bronchospasm requiring intensive treatment in an emergency room or at home, blood dyscrasias or convulsions that do not result in hospitalization, or development of drug dependency or drug abuse.

Life threatening refers to immediate risk of death as the event occurred per the reporter. A life-threatening experience does not include an experience that had it occurred in a more severe form might have caused death, but as it actually occurred did not create an immediate risk of death. For example, hepatitis that resolved without evidence of hepatic failure would not be considered life threatening, even though hepatitis of a more severe nature can be fatal. Similarly, an allergic reaction resulting in angioedema of the face would not be life threatening, even though angioedema of the larynx, allergic bronchospasm, or anaphylaxis can be fatal.

Hospitalization is official admission to a hospital. Hospitalization or prolongation of a hospitalization constitutes criteria for an AE to be serious; however, it is not in itself considered an SAE. In absence of an AE, a hospitalization or prolongation of a hospitalization should not be reported as an SAE by the participating investigator. This is the case in the following situations:

The hospitalization or prolongation of hospitalization is needed for a procedure required by the protocol;

The hospitalization or prolongation of hospitalization is part of a routine procedure followed by the center (e.g., stent removal after surgery). This should be recorded in the study file.

In addition, a hospitalization for a pre-existing condition that has not worsened does not constitute an SAE.

Disability is defined as a substantial disruption in a person's ability to conduct normal life functions.

If there is any doubt about whether the information constitutes an SAE, the information is treated as an SAE.

A protocol-related AE is an AE occurring during a clinical study that is not related to the test article, but is considered by the investigator or the medical monitor (or designee) to be related to the research conditions, i.e., related to the fact that a subject is participating in the study. For example, a protocol-related AE may be an untoward event related to a medical procedure required by the protocol.

Other reportable information: Certain information, although not considered an SAE, must be recorded, reported, and followed up as indicated for an SAE. This includes:

Pregnancy exposure to a test article: If a pregnancy is confirmed, use of the test article must be discontinued immediately. Information about pregnancy exposure includes the entire course of pregnancy and delivery, and perinatal and neonatal outcomes, even if there are no abnormal findings. Both maternal and paternal exposures are considered other reportable information. For exposure involving the female partner of a male subject, the necessary information must be collected from the subject, while respecting the confidentiality of the partner.

Lactation exposure to a test article with or without an AE;

Overdose of a test article as specified in this protocol with or without an AE; Inadvertent or accidental exposure to a test article with or without an AE.

Statistical Analysis

Enrollment of a total of 24 subjects (8 subjects per treatment group) was planned to achieve at least 18 evaluable subjects. The sample size selected was based on the number of subjects needed to provide estimates of the PK parameters. A total of 31 subjects (10-11 per treatment group) were enrolled.

The following subject analysis populations had been defined: the Intent-to-treat (ITT) population was all randomized subjects; the Safety population was all randomized subjects who receive any amount of test article; and the PK population was all subjects who receive test article and have evaluable PK parameter data.

Descriptive statistics were presented for the plasma PK parameter estimates for AUC, $C_{max}$, and $T_{max}$, by treatment groups following the initial (Day 1) and final (Day 5) dose. In addition, descriptive statistics were presented for the PK parameter estimates for $T_{1/2}$, $\lambda_z$, $C_L$ and $V_d$ for the intravenous dose on Day 1 for Group 1.

Descriptive statistics were summarized by treatment group for the urine sample volume, Compound 1 concentration, and the amount excreted within a dosing interval, urinary excretion rates and CLr (following the initial and final dose).

All safety data was summarized by treatment groups and the incidence of AEs was presented by system organ class and preferred term according to the Medical Dictionary of Regulatory Affairs (MedDRA®), relationship to the test article, and severity. Descriptive statistics of clinical laboratory, vital signs and 12-lead ECG results and the change from baseline were presented as will a summary of clinically notable values.

a) Analysis Populations

The number and percentage of subjects with a subject report of clinical response, investigator assessment of clinical response and a microbiological response were presented at each time point measured by treatment group.

A number of subject populations had been defined for the various analyses of efficacy and safety, as follows:

The Intent-to-Treat (ITT) population consist of all randomized subjects, i.e., all enrolled subjects who have received at least one dose of study medication.

The Safety population consists of all randomized subjects who received at least 1 dose of test article. Safety will be assessed through the use of summary statistics and clinical review of reported AEs, changes in vital signs, ECGs, and laboratory results obtained from blood samples taken during the study.

The PK population consist of all subjects who receive test article and have evaluable PK parameter data.

In addition, the patients in the study were monitored for adverse events (AE). An adverse event is any untoward medical occurrence temporally associated with the use of a medical product in a subject, whether or not the event is considered causally related to the medical product. An AE can be a new occurrence or an existing process that increases significantly in intensity or frequency.

b) Demographics and Baseline Characteristics

Demographics (including age, ethnicity and race) and baseline characteristics were summarized in the ITT population by treatment group. Demographic, relevant medical history, current medical conditions, results of laboratory screens, drug tests and any other relevant information were listed by treatment group and subject. Descriptive statistics of the duration of test article treatment were provided by treatment group. The number and percentage of subjects who prematurely discontinued test article and the reason for discontinuation and the number and percentage of subjects prematurely discontinuing the study and the primary reason for discontinuation were presented by treatment group.

c) Statistical Analysis of Pharmacokinetic Variables

The Compound 1 plasma concentration data was listed and summarized by time point and treatment group. The following PK parameters were estimated from the Compound 1 plasma concentration-time data:

| Parameter | Description |
| --- | --- |
| $AUC_{0-12}$ | Area under the plasma concentration-time curve from time 0 to 12 hours after the initial (Day 1) dose for Groups 2 and 3, calculated by the linear trapezoidal rule. |
| $AUC_{0-24}$ | Area under the plasma concentration-time curve from time 0 to 24 hours after the initial dose (Day 1) for Group 1 and for final dose on Day 5 for Groups 1, 2 and 3, calculated by the linear trapezoidal rule. |
| $AUC_{inf}$ | Area under the plasma concentration-time curve from time 0 to infinity after the initial dose (Day 1) for Group 1, only, calculated by the linear trapezoidal rule. |
| $AUC_{0-t}$ | Area under the plasma concentration-time curve from time 0 to the last quantifiable concentration within a dosing interval, calculated by the linear trapezoidal rule. |
| $C_{max}$ | Maximum (peak) observed plasma concentration. |
| $T_{max}$ | Time to reach maximum observed plasma concentration. |
| $T_{1/2}$ | Terminal elimination half-life, calculated as $T_{1/2} = \ln(2)/\lambda_z$ (Group 1, Day 1, only) |
| $\lambda_z$ | Terminal phase rate constant, calculated using linear regression on the terminal portion of the ln-concentration versus time curve (Group 1, Day 1, only) |

Descriptive statistics were presented for the PK parameter estimates for area under the curve (AUC), maximum plasma concentration ($C_{max}$), and time to reach $C_{max}$ ($T_{max}$), by treatment groups following the initial (Day 1) and final (Day 5) dose. Descriptive statistics will also be presented for the PK parameter estimates for $T_{1/2}$, $\lambda_z$, systemic clearance (CL) and apparent volume of distribution (Vd) for Group 1 on Day 1 following the intravenous dose.

The urine sample volume, its Compound 1 concentration, the amount of Compound 1 excreted in the urine (product of volume and concentration) over a dosing interval, the urinary excretion rates and renal clearance (CLr) of Compound 1 following the initial Day 1 and final Day 5 doses were summarized by the treatment groups.

d) Safety Analysis

All subjects in the Safety population were included in the safety analyses. Prior and concomitant medications entered into the database were coded using the World Health Organization (WHO) Drug Reference List, which employs the Anatomic Therapeutic Chemical (ATC) classification system. Adverse events were coded using the Medical Dictionary for Regulatory Activities (MedDRA) terminology.

All vital signs data was listed by treatment group, subject, and visit/time, and if ranges were available, abnormalities (and relevant orthostatic changes) were flagged. Descriptive statistics of vital signs by visit/time and for the change from baseline, were provided by treatment group. A summary of any post-baseline clinically notable values were presented by treatment group.

All 12-lead ECG data was listed by treatment group, subject and visit/time, and abnormalities were flagged. Descriptive statistics of ECG parameters by visit/time and for the change from baseline were provided by treatment group. A summary of any post-baseline clinically notable values was presented by treatment group.

All clinical laboratory data was listed by treatment group, subject, and visit/time and abnormalities were flagged. Summary statistics were provided by treatment and visit/time. Descriptive statistics of clinical laboratory parameters by visit/time and for the change from baseline will be provided by treatment group. A summary of any post-baseline clinically notable values was presented by treatment group.

All information obtained on AEs was displayed by and subject and treatment. The incidence of treatment-emergent AEs (TEAEs) was presented by system organ class and preferred term according to MedDRA, by relationship to the test article administration and by severity. A listing presented TEAEs leading to premature discontinuation of study drug and for serious AEs. A TEAE was defined as an AE that occurs during or after the first dose of test article. A subject with the same AE occurring more than once was only counted once for the preferred term and a subject with multiple AEs within a body system was only counted once towards the total of this body system.

All concomitant therapies were listed by subject.

e) Efficacy Analyses

The subject reported clinical response at the EOT visit was determined programmatically based on the subject assessment of UTI symptom severity. The Subject Reported Clinical Response can be Clinical Success, Clinical Failure and Indeterminate (defined below).

Clinical Success: The clinical outcome was considered a success if there was improvement compared to the assessment at screening by at least 1 number score, as reported by the subject, in at least two of the symptoms (dysuria, frequency, urgency, suprapubic pain) reported at screening (with no worsening in any of the other symptoms).

Clinical Failure: Persistence or worsening of UTI symptoms or the subject required alternative antibiotic(s) for treatment for their UTI during the course of the study.

Indeterminate: The visit was not completed.

Subjects who were a clinical failure at an earlier time point were considered a clinical failure at subsequent time points. The number and percentage of subjects with a clinical response of success, failure and indeterminate was presented for EOT and PTE visits by treatment group.

The microbiological outcome was determined programmatically based on the local and Central Laboratory microbiological analyses. For an isolate to be considered a pathogen at screening, it must presented in the urine sample at $\geq 10^5$ CFU/mL or the pathogen should be isolated from both the blood and urine at any CFU count. Microbiological outcome was defined as:

Eradication: A urine culture, taken at the PTE visit shows that all pathogens found at screening at $>10^5$ CFU/mL were reduced to $<10^4$ CFU/mL.

Persistence: A urine culture, taken any time after the completion of therapy, grows $>10^4$ CFU/mL of the original pathogen.

Indeterminate: no follow-up urine culture was obtained.

The pathogens isolated at baseline were presented by genus and species by treatment group. The number and percentage of subjects with a by-subject and by-pathogen eradication, persistence and indeterminate microbiologic response were presented. A listing of all baseline and post-baseline isolates was provided.

Investigator's assessment of clinical response at the EOT and PTE visits with outcomes of Clinical Success, Clinical Failure or Indeterminate as defined above. Subjects who were a clinical failure at an earlier time point were considered a clinical failure at subsequent time points. The number and percentage of subjects with an Investigator's assessment of success, failure and indeterminate were presented for EOT and PTE visits by treatment group.

Those skilled in the art recognizes, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference.

Example 2 In Vitro Protein Binding with Compound 1

Compound 1 is a first-in-class aminomethylcycline antibiotic that is undergoing clinical development as once daily oral or intravenous monotherapy for acute bacterial skin and skin structure infections and community-acquired bacterial pneumonia. In vitro, Compound 1 demonstrates activity against Gram-positive and Gram-negative aerobes including multi-drug resistant strains of *Staphylococcus* spp. and *Streptococcus* spp., as well as anaerobes and atypical bacteria including *Legionella* spp., *Mycoplasma* spp., and *Clostridium difficile* (Macone et al., *Antimicrob. Agents Chemother.*, 58:1127-1135, 2014). In phase 1 studies, Compound 1 demonstrated a linear dose-plasma concentration profile, an elimination half-life of approximately 17 hours, and peak plasma concentrations of 0.6 and 1.8 mg/L after 300 mg oral and 100 mg IV doses, respectively (Sun et al., Poster presented at 21st European Congress on Clinical Microbiology and Infectious Diseases, May 7-11, 2011, Milan, Italy; Ting et al., Abstract K-124, presented at the 50th ICAAC, Sep. 12-15, 2010, Washington, D.C.). No dosage adjustment is necessary for hepatic impairment, and Compound 1 has a low potential for drug-drug interactions based on studies of human transporter mechanisms and cytochrome P-450-mediated metabolism (Hanna et al., *Br J Pharmacol.* 2016a; Hanna et al., *Drug Metab Disp.* 2016b).

In patients with complicated skin and skin structure infection, Compound 1 demonstrated clinical efficacy and tolerability that was comparable to linezolid (Noel et al., *Antimicrob. Agents Chemother.*, 56:5650-5654, 2012; Noel et al., Poster presented at 22nd European Congress on Clinical Microbiology and Infectious Diseases, Mar. 31-Apr. 3, 2012a, London, UK). Compound 1 is undergoing clinical development in phase 3 studies as oral and intravenous (IV) monotherapy for the treatment of acute bacterial skin and skin structure infections (ABSSSI) and community-acquired bacterial pneumonia (CABP).

In this example, Compound 1 protein binding was investigated during in vitro studies in mouse (CD-1), rat (Han-Wistar), monkey (Cynomolgus), and human plasma (defrosted plasma pools). Binding was determined at nominal Compound 1 concentrations of 10, 100, 1,000, and 10,000 ng/mL. For human binding studies, plasma was obtained from the blood of three healthy male volunteers. Plasma was defrosted from storage at −20° C. before use, and pools of human plasma were used for all studies. Plasma from mouse, rat, and monkey was supplied by Harlan Laboratories Ltd. (Netherlands), Milan Analytica AG (Rheinfelden, Switzerland) and Centre de Primatologie ULP (France), respectively.

Protein binding was measured using an ultrafiltration method. To asses the suitability of ultrafiltration, the recovery and free permeation of [$^{14}$C]-labelled Compound 1 in PBS buffer were investigated. Two aliquots of PBS (4 mL) were spiked with stock solutions B and C (1:200, v:v) to give final nominal concentrations of 1,000 and 100 ng/mL [$^{14}$C]-Compound 1, respectively. Three 1 mL aliquots per concentration were introduced into CENTRIFREE® devices and spun for 1 min at 2000 g (filtrate ≤500 μL). Samples of the spiked solutions, the filtrate and retentate were quantified by LSC; volumes were determined by weighing.

The free permeation of the test compound in PBS was evaluated as follows:

$$\text{Ratio}=[C_{uf}/C_r]$$

with $C_{uf}$ being the concentration in the ultrafiltrate (ng/mL) and $C_r$ the concentration in the retentate (ng/mL). A ratio of >0.70 indicates that the compound passes relatively freely through the ultrafiltration membrane of the CENTRIFREE® device.

The non-specific adsorption of the test compound in PBS and plasma was evaluated from the recovery as follows:

$$\text{recovery (\%)}=(\text{amount recovered after centrifugation}\times 100)/(\text{amount introduced})$$

A recovery >0.8 indicates that the loss of compound due to non-specific adsorption onto the device are acceptable. In case the recovery is smaller than 80% in PBS but higher in plasma and the compound permeates freely, the method could still be employed.

The buffer controls for the standard ultrafiltration method indicated that the losses of compound due to a non-specific adsorption onto the device are acceptable. The recovery was ≥90% and the free permeation ratio was ≥0.99.

Plasma bound and unbound concentrations of Compound 1 were determined by a LC-MS/MS method with a lower limit of quantification=5.0 ng/mL. Specifically, concentrations of Compound 1 was determined by an UPLC-MS/MS method. Blank human plasma/human plasma ultrafiltrate (50:50), and study samples were thawed, and a 0.1 mL aliquot of each thawed sample was transferred to an appropriate well in a 96-well polypropylene block, 2 mL capacity. Standards and quality control samples were prepared on the day of analysis by adding a 20 μL aliquot of an appropriate standard or QC spiking solution in methanol. A 25 μL aliquot of the internal standard (at 200 ng/mL in methanol) was added to each well except blanks. All ultrafiltrate samples were mixed 1:1 with human plasma. All Plasma samples were mix 1:1 with ultrafiltrate. The 10,000 ng/mL ultrafiltrate and 10,000 ng/mL plasma samples were diluted 1:9 and processed.

Samples were processed using protein precipitation. A 0.5 mL aliquot of an acetonitrile/ethanol/acetic acid mixture (90:10:0.1, v:v:v) was added to each sample; samples were mixed using a vortex mixer for 10 minutes, and centrifuged 3800 rpm (approximately 2500×g) for 10 min at 10° C. A 500 μL aliquot of the supernatant transferred to a clean 96 well plate, 2 ml. An aliquot 500 μL of 80:20 (water:acetonitrile) was added to all the samples. Samples were mixed by vortexing for 0.5 min. A 6 μL sample volume was injected into the UPLC/MS/MS system for analysis.

Samples were then assayed on an UPLC-MS/MS system, consisting of an Acquity UPLC with a quaternary pump, a ample manager, and sample organizer, coupled to a Sciex API4000 mass spectrometer running Analyst software version 1.4.2 (Foster City, Calif., USA). The mass spectrometer was operated in the positive ion mode, using electro spray ionization, with a source temperature of 500° C. Chromatographic separation was carried out on an Acquity BEH C18, 50×2.1, 1.7 particle (Waters, Mass.) at a flow rate of 1.0 mL/min. The column temperature was maintained at 65° C. Compound 1 and the internal standard were eluted using a gradient method with a mobile phase consisting of A: 10 mM ammonium formate plus 0.2% formic acid; and B: acetonitrile plus 0.2% formic acid. The gradient was 2% B for 0.25 min., increasing to 95% B at 0.60 minutes followed by a 0.40 minute hold at 95% B. The retention time for Compound 1 was 0.56 minutes. The ions monitored for Compound 1 was the parent $[M+H]^+$ ion at m/z 557.3.0; the product ions at m/z 453.4.

Data processing: Calibration curves ($y=x^2+xb+c$ or $y=ax+b$), represented by the plots of the respective peak area ratios (y) of the analyte or the internal standard versus the concentrations (x) of the calibration samples, were generated using weighted ($1/x^2$ or $1/x$) quadratic least-squares regression as the mathematical model. The quantification was performed using Analyst software and Watson LIMS version 7.2.0.01. Concentrations in QC and study samples were calculated from the resulting peak area ratios and interpolation from the regression equations of the respective calibration curves. The lower limit of quantitation was 5.0 ng/mL for Compound 1.

The results are shown in the table below.

| Analytical Performance of Compound 1 Quality Control Samples | | | | | | |
|---|---|---|---|---|---|---|
| | Compound 1 Concentration (ng/mL) | | | | | |
| | 5 | 10 | 50 | 100 | 500 | 1,000 |
| Calibration Standard | | | | | | |
| Mean (SD) | 5.2 (0.31) | 9.2 (0.35) | 41.5 (5.07) | 105 (17.7) | 589 (31.6) | 1050 (175) |
| % CV | 5.9 | 3.8 | 12.2 | 16.9 | 5.4 | 16.7 |
| % Bias | 4 | −8.3 | −17 | 5 | 17.8 | 5 |
| N | 4 | 3 | 4 | 3 | 4 | 4 |
| QC Samples | | | | | | |
| Mean (SD) | 5.0 (0.24) | 8.2 (0.57) | 43.7 (5.93) | 101 | 581 | 1030 (116) |
| % CV | 4.7 | 7 | 13.6 | — | — | 11.3 |
| % Bias | 0.8 | −18.2 | −12.6 | 1 | 16.2 | 3 |
| N | 4 | 4 | 4 | 2 | 2 | 6 |

The results showed that Compound 1 was weakly bound to plasma proteins in human plasma as well as in monkey, mouse, and rat plasma (see data below).

Mean (SD) Plasma Protein Binding Parameters for Compound 1 in Mouse, Rat, Monkey, and Human Plasma (Values Calculated Over a Nominal Concentration Range of 10-10,000 ng/mL)

| Species | Mean (SD) Bound Fraction (%) |
|---|---|
| Mouse | 15.3 (5.31) |
| Rat | 26.1 (12.3) |
| Money | 21.2 (7.26) |
| Human | 21.3 (9.72) |

Thus, over the concentration range of 10-10,000 ng/mL, no apparent concentration dependent effect of Compound 1 on plasma protein binding was observed. The mean±SD unbound protein fraction in human plasma was 78.7±9.7%. In animals, the mean unbound plasma protein fractions were rat (73.9±12.1%), monkey (78.8±7.3%), and mouse (84.7±5.3%). Also see FIG. 1.

The free, unbound fraction of antimicrobials is correlated with antimicrobial activity (Schmidt et al., *Antimicrob. Agents Chemother.*, 52(11):3994-4000, 2008; Gonzalez et al., *Clin Microbiol Rev.* 26:274-288, 2013). These results show that Compound 1 was 21% bound to human plasma protein, and binding was not concentration dependent. Meanwhile, Compound 1 was weakly bound (15% to 26%) to plasma proteins in animal species. The low human plasma protein binding of Compound 1 contrasts markedly with other tetracyclines, which exhibit high, often concentration-dependent protein binding near 80% (see table below).

| Analytical Performance of Compound 1 Quality Control Samples | | | | | |
|---|---|---|---|---|---|
| | Compound 1 Concentration (ng/mL) | | | | |
| | Mean | 100 | 1,000 | 10,000 | 100,000 |
| Compound 1 | 21.3% | 34.4% | 12.2% | 20.2% | — |
| Eravacycline | 79-97% | 79.3% | 87.0% | 89.3% | 97.0% |
| Tigecycline | 71-87% | — | — | — | — |
| Ultrafiltration | — | 71% | 87% | — | — |
| Ultracentrifugation | — | 73% | 79% | — | — |
| Minocycline | 76% | — | — | — | — |
| Doxycycline | 82-93% | — | — | — | — |

(Agwuh and MacGowan, *J Antimicrob Chemother.* 58(2): 256-265, 2006; Muralidharan et al., 2005; Singh et al., Abstract A-015 presented at the 53rd ICAAC Meeting, Sep. 10-13, 2013, Denver, CO)

The low human plasma protein binding of Compound 1 (21%) contrasts markedly with other tetracyclines, which exhibit high concentration dependent protein binding (approximately 80%). Specifically, eravacycline and tigecycline demonstrate atypical, non-linear protein binding—atypical in that plasma protein binding increases with increasing drug concentrations (Muralidharan et al., *Antimicrob. Agents Chemother.*, 49(1):220-229, 2005; Singh et al., *Abstract A-015 presented at the 53rd ICAAC Meeting, Sep. 10-13*, 2013, Denver, Colo.). Daptomycin, delafloxacin, oritavancin, telavancin, solithromycin and tedizolid are >75% protein bound in human plasma (Lawrence et al., Abstract A-1956 presented at the 52nd ICAAC Annual Meeting, Sep. 9-12, 2012; Arhin et al., *Antimicrob. Agents Chemother.*, 54(8):3481-3483, 2010; Rodvold et al., *Antimicrob. Agents Chemother.*, 56(10):5076-5081, 2012; McCullough et al., Abstract A-1878 presented at the IDSA Annual Meeting, Oct. 27, 2008; Housman et al., *Antimicrob. Agents Chemother.*, 56(5):2627-2634, 2012). Linezolid is 31% protein bound (see package insert).

Thus, in contrast to other tetracycline-derived antibiotics, Compound 1 has markedly low human plasma protein binding (21%), with no concentration-dependent binding. These data may be relevant to the clinical effectiveness of Compound 1 since the free, unbound fraction of the drug typically is most closely correlated with antimicrobial activity.

References cited in the Example are listed below, and are all incorporated by reference:

Agwuh K N, MacGowan A. "Pharmacokinetics and pharmacodynamics of the tetracyclines including glycylcyclines." *J Antimicrob Chemother.* 2006; 58(2):256-65.

Arhin F F, Belley A, McKay G, Beaulieu S, Sarmiento I, Parr T R Jr, Moeck G. "Assessment of oritavancin serum protein binding across species." *Antimicrob. Agents Chemother.*, 2010 August; 54(8):3481-3.

Gonzalez D, Schmidt S, Derendorf H. "Importance of relating efficacy measures to unbound drug concentrations for anti-infective agents." *Clin Microbiol Rev.* 2013; 26:274-88.

Hanna I, Sun H, Alexander N, Natrillo A, Pelis R M, Wang L, Tanaka S K. "Lack of drug interaction potential with omadacycline, an aminomethylcycline, with human drug transporters. *Br J Pharmacol.* 2016a.

Hanna I, Sun H, Zhu B, Gu H, Wang L, Pelis R M, Einoff H J, Chun D Y, Tanaka S K. "Omadacycline is not metabolized and does not induce or inhibit cytochrome P450 enzymes in vitro." *Drug Metab Disp.* 2016b.

Honeyman L, Ismail M, Nelson M, Bhatia B, Bowser T E, Chen J, Mechiche R, Ohemeng K, Verma A K, Cannon E P, Macone A, Tanaka S K, Levy S. "Structure-activity relationship of the aminomethylcyclines and the discovery of omadacycline." *Antimicrob. Agents Chemother.*, 2015; 59:7044-7053.

Housman S T, Pope J S, Russomanno J, Salerno E, Shore E, Kuti J L, Nicolau D P. "Pulmonary disposition of tedizolid following administration of once-daily oral 200-milligram tedizolid phosphate in healthy adult volunteers." *Antimicrob. Agents Chemother.*, 2012 May; 56(5):2627-34.

Lawrence L, Longcor J, Li D, Reeve M, Hoover R, McEwen A B, Ford G, Wood S G. "Metabolism and mass balance of [14C]-Delafloxacin in healthy human volunteers following intravenous administration." Abstract A-1956 presented at the 52nd ICAAC Annual Meeting, Sep. 9-12, 2012.

Macone A B, Caruso B K, Leahy R G, Donatelli J, Weir S, Draper M P, Tanaka S K, Levy S B. "In vitro and in vivo antibacterial activities of omadacycline, a novel aminomethylcycline." *Antimicrob. Agents Chemother.*, 2014; 58:1127-35.

McCullough J, Shaw J-P, Tsai S J, Shaw J P. "Protein binding of [$^{14}$C]telavancin I plasma and human skin blister fluid." Abstract A-1878 presented at the IDSA Annual Meeting, Oct. 27, 2008.

Muralidharan G, Micalizzi M, Speth J, Raible D, Troy S. "Pharmacokinetics of tigecycline after single and multiple doses in healthy subjects." *Antimicrob. Agents Chemother.*, 2005; 49(1):220-229.

Noel G J, Draper M P, Hait H, et al. "A randomized, evaluator-blind, phase 2 study comparing the safety and efficacy of omadacycline to those of linezolid for treatment of complicated skin and skin structure infections." *Antimicrob. Agents Chemother.*, 2012; 56:5650-5654.

Noel G J, Draper M P, Hait H, Tanaka S K. "Safety and efficacy of PTK 0796 (Omadacycline) as treatment of complicated skin and soft tissue infection (cSSTI)." Poster presented at 22nd European Congress on Clinical Microbiology and Infectious Diseases, Mar. 31-Apr. 3, 2012a, London, U K.

Rodvold K A, Gotfried M H, Still J G, Clark K, Fernandes P. "Comparison of plasma, epithelial lining fluid, and alveolar macrophage concentrations of solithromycin (CEM-101) in healthy adult subjects." *Antimicrob. Agents Chemother.*, 2012; 56(10):5076-81.

Schmidt S, Röck K, Sahre M, Burkhardt O, Brunner M, Lobmeyer M T, Derendorf H. "Effect of protein binding on the pharmacological activity of highly bound antibiotics." *Antimicrob. Agents Chemother.*, 2008; 52(11): 3994-4000.

Singh R S P, Falcao N M S, Sutcliffe J, Derendorf H. "Plasma protein binding of eravacycline in mouse, rate, rabbit, Cynomologus monkey, African green monkey and human using microdialysis." Abstract A-015 presented at the 53rd ICAAC Meeting, Sep. 10-13, 2013, Denver, Colo.

Sun H, Maietta R, Machineni S, et al. "A single-dose study to evaluate the pharmacokinetics, safety, and tolerability of multiple formulations of PTK 0796 in healthy subjects." Poster presented at 21st European Congress on Clinical Microbiology and Infectious Diseases, May 7-11, 2011, Milan, Italy.

Ting L, Sun H, Kovacs S J, et al. "Pharmacokinetics of intravenous and oral PTK796, a new aminomethylcycline antibiotic." Abstract K-124, presented at the 50th ICAAC, Sep. 12-15, 2010, Washington, D.C.

Example 3 In Vitro Activity of Compound 1 Against *E. coli* Biofilms

Microbial biofilms are defined by a dense extracellular polymeric substance that can act as a physical barrier to the external environment, and results in a subpopulation of metabolically quiescent microbes, which can lead to a remarkable tolerance to antibiotics that normally kill planktonic bacteria.

Sub-MIC doses of many different classes of antibiotics have been found to stimulate the biofilm growth mode of exposed bacteria. For example, treatment of *E. coli* with sub-MIC doses of five different classes of translational inhibitors, including tetracycline (chemical analogue of Compound 1), has been demonstrated to result in increased biofilm growth (Boehm et al., *Molecular Microbiology* 72(6): 1500-1516, 2009; Hoffman et al., *Nature* 436(7054): 1171-1175, 2005; Kaplan, *International Journal of Artificial Organs* 34(9): 737-751, 2011). This finding is of particular relevance considering clinical implications of microbial biofilms and the fact that patients' sera routinely contain sub-inhibitory doses of antibiotics at the beginning and end of treatment, as well as in between doses.

Data presented herein confirmed that Compound 1 exhibits potent bacteriostatic activity against both Gram-negative and Gram-positive bacteria, including *E. coli*, the major pathogen in most UTI patients. The data also demonstrates that Compound 1 has anti-biofilm activity against *E. coli* biofilm In vitro.

Specifically, by focusing on *Escherichia coli* (ATCC 25922), which is a common cause of community-acquired infections, doses of Compound 1 above and below the minimum inhibitory concentration (MIC) for planktonic cells were assessed for biofilm prevention and/or induction, and against established biofilms using the MBEC™ 96 well plate high throughput screening device.

The MBEC™ assay (formerly the Calgary biofilm device; Innovotech Inc., Canada) is a well-established high throughput assay for assessment of anti-biofilm activity of test agents in a 96-well format. Within this assay, the biofilm is formed on the plastic pegs of the plate lid. After inoculated media is introduced to the wells of the 96-well plate, the plate is placed in a shaking incubator to generate the necessary shear force for biofilm growth on the pegs. Following a suitable incubation time, the individual biofilms can be treated with varying concentrations of test agents (challenge plate). After the desired treatment time, the remaining biofilm-associated bacteria are retrieved from the pegs through sonication (recovery plate). Serial dilution and/or plating of the recovered bacterial suspension allow for the quantification of test agents' efficacy against pre-formed biofilms. Additionally, readout of the challenge plate from the biofilm treatment can be used to determine MIC values of test agents. The absence of growth in the recovery plate indicates complete biofilm eradication and the lowest concentration of a test agent that achieves this is designated as the minimum biofilm eradication concentration (MBEC). The MBEC™ assay is also amenable to assess potential synergistic effects of combination treatments, as well as efficacy of test agents in inhibiting or inducing biofilm formation.

Antimicrobial Activity of Compound 1 Against E. coli

Figure 2:
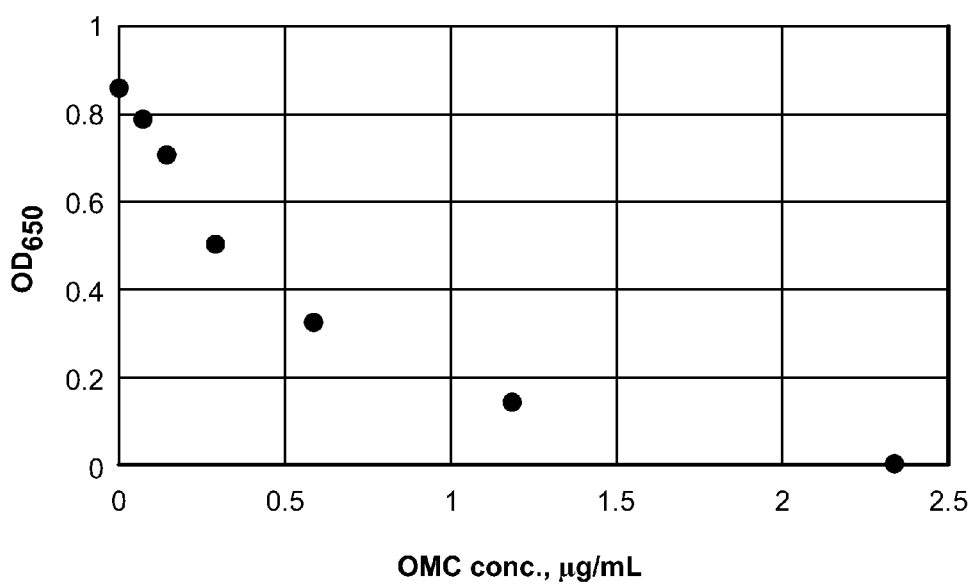
FIG. 2 shows OD$_{650}$ of planktonic *E. coli* (ATCC 25922) after 24 hours treatment with varying concentrations of Compound 1.

Antimicrobial activity of Compound 1 against E. coli (ATCC 25922) was determined using a standard broth microdilution method (CLSI in Methods for Dilution Antimicrobial Susceptibility Tests for Bacteria That Grow Aerobically, Approved Standard M7-A8, Clinical and Laboratory Standards Institute, Wayne, Pa. (USA), 2011, incorporated herein by reference) with slight modifications. The results are shown in FIG. 2.

Extrapolating from the plot (FIG. 2), the minimum inhibitory concentration (MIC) of Compound 1 was estimated to be 1.13 µg/mL. This is consistent with reported MIC against E. coli being 0.5-2 µg/mL (Macone, Antimicrobial agents and Chemotherapy 58 (2): 1127-1135, 2014).

Anti-Biofilm Activity of Compound 1

The MBEC™ plates were inoculated with $10^7$ CFU/mL of stationary phase E. coli (ATCC 25922) and incubated for 24 hours to allow formation of a robust biofilm. The individual biofilms formed on the pegs were challenged with varying concentrations of antibiotics for 24 hours, followed by recovery of the surviving bacteria.

Bacterial enumeration was performed using a Most Probable Number (MPN) assay (Sutton, Journal of Validation Technology 16 (3): 35-38, 2010, incorporated herein by reference) in a 96-well format. As a comparison to Compound 1 efficacy, another small molecule antibiotic, ciprofloxacin, was used.

Figure 3:
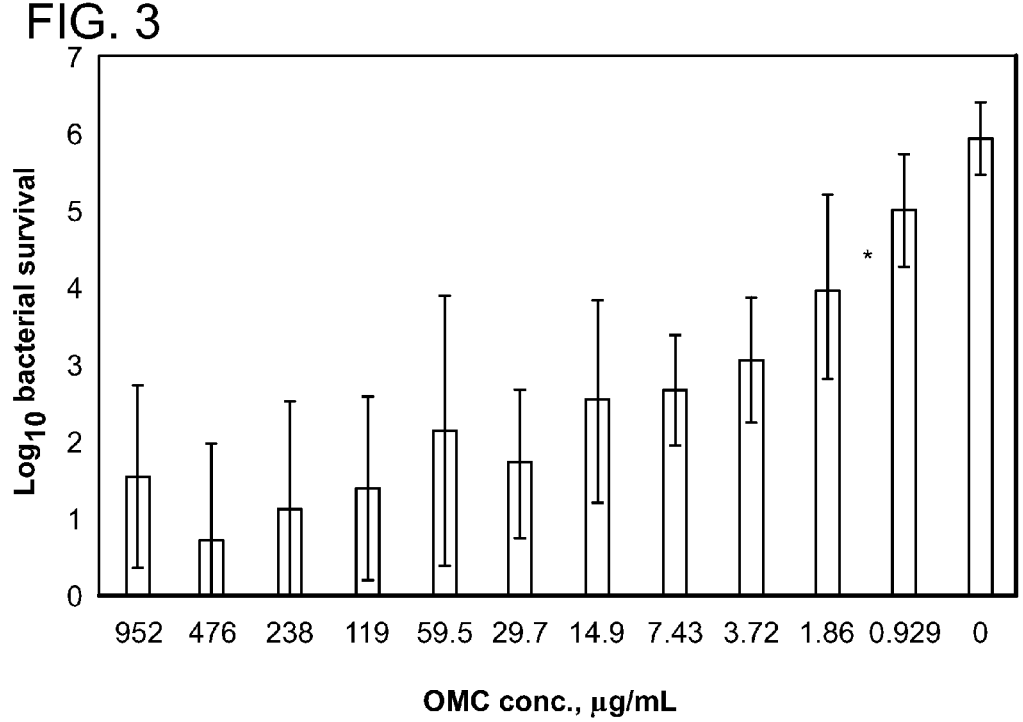
FIG. 3 shows activity of Compound 1 against 24 hour *E. coli* biofilm. * denotes approx. MIC value.
Figure 4:
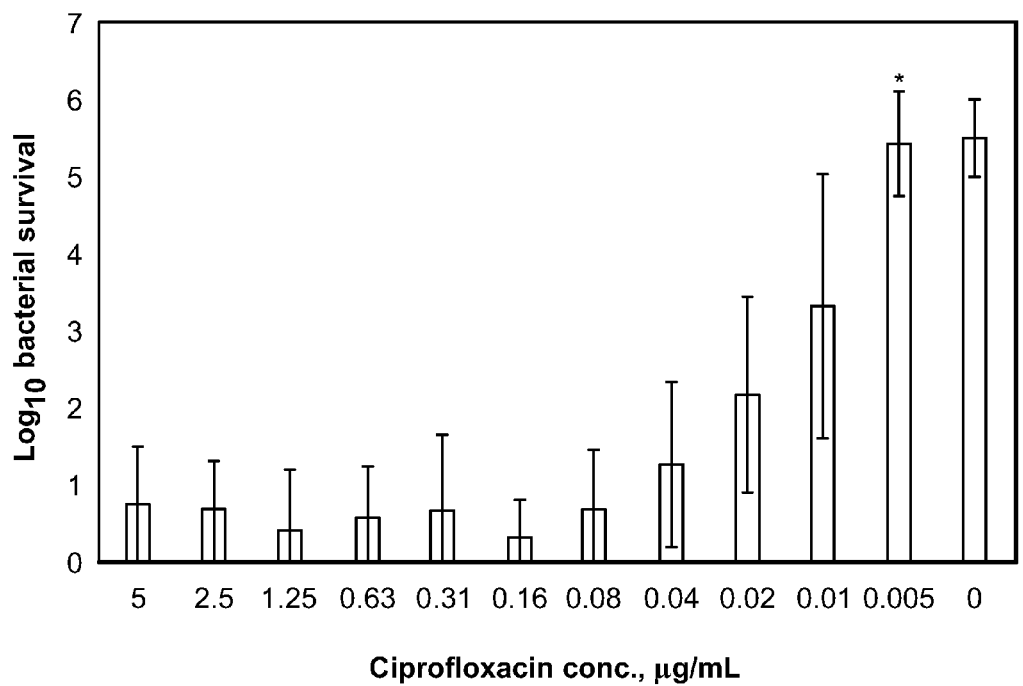
FIG. 4 shows activity of ciprofloxacin against 24 hour *E. coli* biofilm. * denotes approx. MIC value.

Around MIC values (1.13 µg/mL) Compound 1 reduced the total biofilm-associated bacteria by 1-2 log units (FIG. 3). At higher concentrations, the effect is more pronounced with up to 4-5 log units reduction in bioburden. In contrast, at MIC values (5.6 ng/mL) ciprofloxacin did not show activity (FIG. 4), although at higher concentrations, it was also able to elicite significant bioburden reduction (up to 5 log units).

The above results also showed that, while both antibiotics showed significant reduction in the total number of surviving bacteria, none of the treatments resulted in complete biofilm eradication.

Sub-MIC Compound 1 does not Promote Planktonic Adhesion

Figure 5:
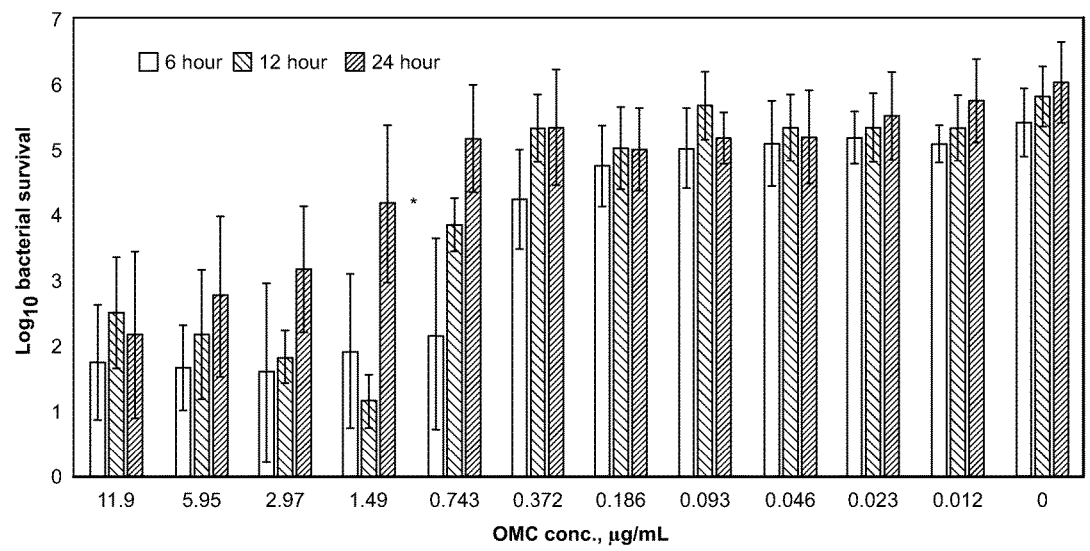
FIG. 5 shows effect of Compound 1 against biofilms established for 6, 12 and 24 hours with addition of planktonic bacteria. * denotes approx. MIC value.

The MBEC™ plates were inoculated with $10^7$ CFU/mL of stationary phase E. coli (ATCC 25922) and incubated for 6, 12 or 24 hours. The biofilms on the pegs were then simultaneously challenged with varying concentrations of Compound 1 and additional $10^6$ CFU/mL planktonic E. coli. Following 24 hour incubation, the biofilm-associated bacteria were recovered and enumerated (as above) to determine if exposure to sub-MIC doses of Compound 1 results in additional adhesion of planktonic bacteria to the biofilms (FIG. 5).

For all biofilm ages tested (6, 12, 24 hours), mean bioburden when treated with sub-MIC concentrations of Compound 1 was lower than that of untreated control biofilms. On average, 24 hour biofilms treated with doses as low as 4% of the MIC (0.046 µg/mL) were reduced by about a log in total biofilm-associated bacteria relative to controls, even in the presence of planktonic bacteria. The results show that sub-MIC concentrations of Compound 1 do not promote additional adhesion of planktonic bacteria.

Inhibition of Biofilm Formation

Figure 6:
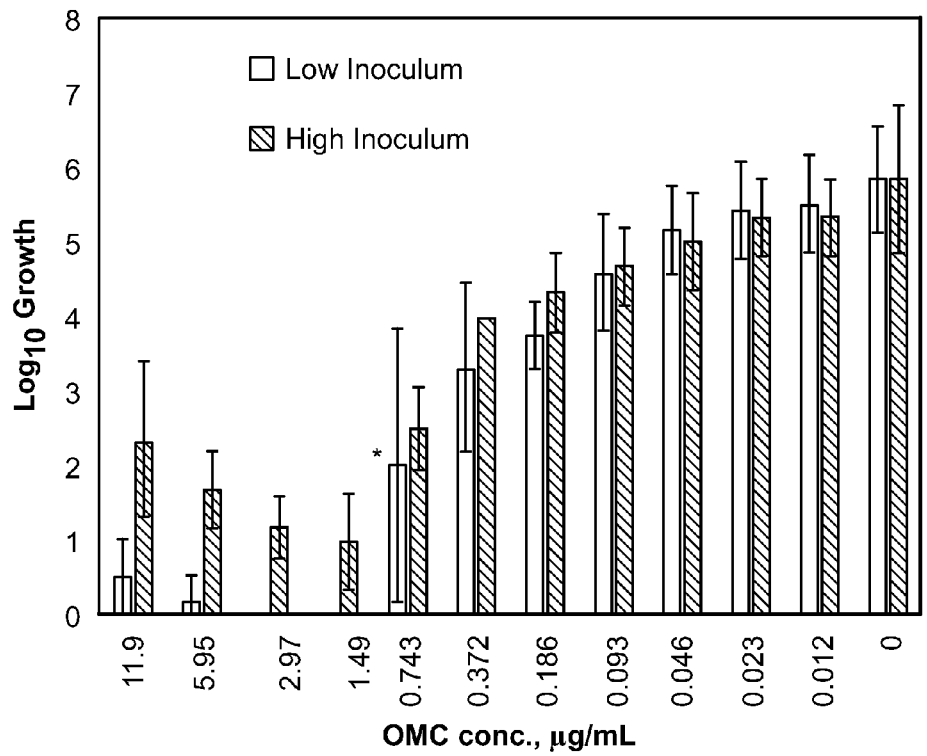
FIG. 6 shows biofilm growth in the presence of Compound 1. * denotes approx. MIC value.
Figure 7:
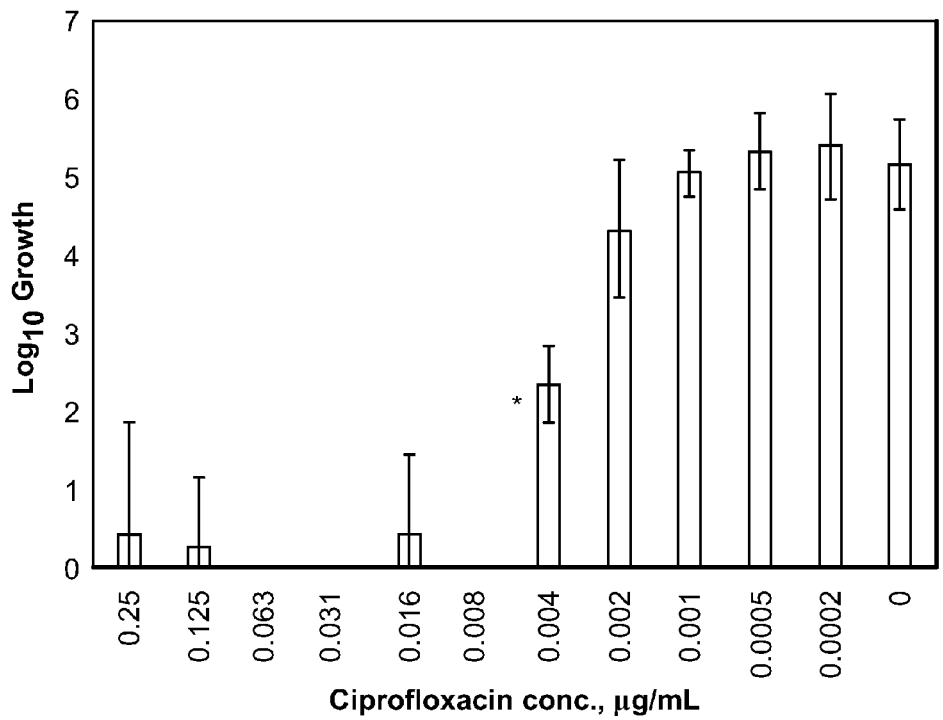
FIG. 7 shows biofilm growth in the presence of ciprofloxacin. * denotes approx. MIC value.

The MBEC™ plates were inoculated with either $10^5$ CFU/mL (low inoculum) or $10^7$ CFU/mL (high inoculum) of stationary phase E. coli (ATCC 25922) with simultaneous addition of antibiotics to evaluate the progression of biofilm formation under antibiotic challenge. After 24 hour incubation, the bacteria were recovered and enumerated (as above). FIG. 6. Effects of ciprofloxacin were evaluated under low inoculum conditions only. FIG. 7.

Sub-MIC concentrations of Compound 1 lead to a decreased number of total biofilm-associated bacteria compared to controls with mean biomass increasing in a step-wise fashion with decreasing dose. For example, 0.743 µg/mL of Compound 1 results in biofilm with approx. 3-4 log units lower total bioburden. Unlike other translation inhibitors shown to induce biofilm formation at sub-MIC doses (Boehm et al., Molecular Microbiology 72(6): 1500-1516, 2009; Hoffman et al., Nature 436(7054): 1171-1175, 2005; Kaplan, International Journal of Artificial Organs 34(9): 737-751, 2011), these data indicate that sub-MIC doses of Compounds 1 not only fail to induce biofilm formation but also actually prevent biofilm formation.

Ciprofloxacin (fluoroquinolone antibiotic) also did not induce biofilm formation at sub-MIC levels. However, the effects of Compound 1 in biofilm prevention were more pronounced. At approx. 15% of the respective MIC values, Compound 1 (0.183 µg/mL) leads to biofilm with approx. 2 log units less of a bioburden compared to control, while ciprofloxacin (1 ng/mL) shows no reduction in the total bioburden.

In conclusion, the above data shows that Compound 1 shows good in vitro activity against E. coli biofilms and is capable of significantly reducing the total bioburden even at concentrations close to MIC. Indeed, biofilm prevention/induction assays indicate that Compound 1 strongly inhibits biofilm formation at all doses above the MIC.

Perhaps more importantly, sub-MIC concentrations of Compound 1 (e.g., 0.74 p g/mL) do not induce E. coli biofilm formation, but rather seem to have a preventative effect, in that mean biofilm formation is reduced by approximately 3 to 4 log units compared to controls, in high and low inoculum conditions, respectively. In contrast to other translation inhibitors, sub-MIC doses of Compound 1 not only failed to induce biofilm formation above the level of controls, several doses below the MIC appear to have an inhibitory effect on biofilm formation.

Example 4 In Vitro Activity of Compound 1 Against Various UTI Pathogens

Antimicrobial activities of Compound 1 against a variety of common pathogens found in UTI were determined using a standard broth microdilution method (CLSI in Methods for Dilution Antimicrobial Susceptibility Tests for Bacteria That Grow Aerobically, Approved Standard M7-A8, Clinical and Laboratory Standards Institute, Wayne, Pa. (USA), 2011, incorporated herein by reference) with slight modifications. The results are shown in Table below.

| Pathogen | No. of Isolates | MIC$_{50}$ (µg/mL) | MIC$_{90}$ (µg/mL) |
|---|---|---|---|
| E. coli (Carbapenem Resistant) | 25 | 1 | 4 |
| E. coli (non-ESBL phenotype) | 10,696 | 0.5 | 2 |
| E. coli (ESBL phenotype) | 2,743 | 1 | 4 |

We claim:

1. A method of treating urinary tract infection (UTI) in a subject in need of treatment thereof, comprising administering to said subject: one intravenous (IV) loading dose, at the first day of treatment, of about 200 mg of 9-[(2,2-dimethyl-propyl amino)-methyl]-minocycline or salt thereof, and one or more oral maintenance doses of 9-[(2, 2-dimethyl-propyl amino)-methyl]-minocycline or salt thereof administered about 24 hours apart, wherein each of said one or more oral maintenance doses comprises about 300 mg of 9-[(2,2-dimethyl-propyl amino)-methyl]-minocycline or salt thereof, such that said subject is treated.

2. The method of claim 1, comprising administering to said subject one oral dose of 300 mg of 9-[(2,2-dimethyl-propyl amino)-methyl]-minocycline or salt thereof once every 24 hours, for a total of 5-14 days.

3. The method of claim 1, comprising administering to said subject one oral dose of 450 mg of 9-[(2,2-dimethyl-propyl amino)-methyl]-minocycline or salt thereof once every 24 hours, for a total of 5-14 days.

4. The method of claim 1, wherein said one or more maintenance doses are administered on the $2^{nd}$-$5^{th}$ day of treatment.

5. The method of claim 1, wherein said UTI is uncomplicated urinary tract infection (uUTI) or cystitis; is complicated urinary tract infection (cUTI) or pyelonephritis; is community-acquired; or is hospital-acquired or healthcare-associated.

6. The method of claim 1, wherein said UTI is characterized by the presence of a pathogen selected from the group consisting of: Escherichia coli (ESBL$^+$, ESBL$^-$, FQS, FQR, Carbapenem-resistant, Carbapenem-susceptible), Staphylococcus saprophyticus, Klebsiella pneumoniae (ESBL$^+$, ESBL$^-$, FQS, FQR), and Enterococcus (E. faecalis VS, E. faecalis VNS, E. faecalis Vancomycin-Resistant (VRE), E. faecium VS, E. faecium VNS, E. faecium Vancomycin-Resistant (VRE)), MSSA, MRSA, MSCoNS, MRCoNS, Streptococcus agalactiae (group B streptococci), K. oxytoca, E. cloacae CeftazS, E. cloacae CeftazR, Citrobacter spp., S. marcescens, and Acinetobacter.

7. The method of claim 6, wherein said pathogen has a titer of $\geq 10^5$ CFU/mL in a urine culture from said subject.

8. The method of claim 1, wherein said subject is treated as demonstrated by a post treatment reduction of at least 10-fold in pathogen titer of a urine culture from said subject.

9. The method of claim 1, wherein said subject has a post treatment pathogen titer of less than $10^4$ CFU/mL on the urine culture from said subject.

10. The method of claim 1, wherein said subject is a female.

11. The method of claim 1, wherein each of said oral dose is administered independently as two or three 150-mg tablets.

12. The method of claim 1, wherein each of said IV dose is administered continuously over about 30 minutes.

13. The method of claim 1, comprising administering to said subject one oral dose of 300 mg of 9-[(2,2-dimethyl-propyl amino)-methyl]-minocycline or salt thereof once every 24 hours, for a total of 4 or 5 days.

14. The method of claim 1, comprising administering to said subject one IV dose of about 200 mg of 9-[(2,2-dimethyl-propyl amino)-methyl]-minocycline or salt thereof, followed by administering to said subject oral maintenance doses each comprising about 300 mg of 9-[(2, 2-dimethyl-propyl amino)-methyl]-minocycline or salt thereof administered about 24 hours apart, for a total of 5 days.

15. The method of claim 1, wherein said one or more maintenance doses are administered on the $2^{nd}$-$14^{th}$ day of treatment.

16. A method of treating urinary tract infection (UTI) in a subject in need of treatment thereof, comprising administering to said subject: two oral loading doses, at the first day of treatment, each about 300 mg of 9-[(2,2-dimethyl-propyl amino)-methyl]-minocycline or salt thereof, and one or more oral maintenance doses of 9-[(2,2-dimethyl-propyl amino)-methyl]-minocycline or salt thereof administered about 24 hours apart, wherein each of said one or more oral maintenance doses comprises about 300 mg of 9-[(2,2-dimethyl-propyl amino)-methyl]-minocycline or salt thereof, such that said subject is treated.

17. The method of claim 16, comprising administering to said subject one oral dose of 300 mg of 9-[(2,2-dimethyl-propyl amino)-methyl]-minocycline or salt thereof once every 24 hours, for a total of 5 days, and further comprising administering to said subject an additional oral dose of 300 mg of 9-[(2,2-dimethyl-propyl amino)-methyl]-minocycline or salt thereof about 12 hours after the first oral dose.

18. The method of claim 16, comprising administering to said subject one oral dose of 300 mg of 9-[(2,2-dimethyl-propyl amino)-methyl]-minocycline or salt thereof once every 24 hours, for a total of 5-14 days, and further comprising administering to said subject an additional oral dose of 300 mg of 9-[(2,2-dimethyl-propyl amino)-methyl]-minocycline or salt thereof about 12 hours after the first oral dose.

19. A method of treating urinary tract infection (UTI) in a subject in need of treatment thereof, comprising administering to said subject: two oral loading doses, at the first day of treatment, each about 450 mg of 9-[(2,2-dimethyl-propyl amino)-methyl]-minocycline or salt thereof, and one or more oral maintenance doses of 9-[(2,2-dimethyl-propyl amino)-methyl]-minocycline or salt thereof administered about 24 hours apart, wherein each of said one or more oral maintenance doses comprises about 450 mg of 9-[(2,2-dimethyl-propyl amino)-methyl]-minocycline or salt thereof, such that said subject is treated.

20. The method of claim 19, comprising administering to said subject one oral dose of 450 mg of 9-[(2,2-dimethyl-propyl amino)-methyl]-minocycline or salt thereof once every 24 hours, for a total of 5-14 days, and further comprising administering to said subject an additional oral dose of 450 mg of 9-[(2,2-dimethyl-propyl amino)-methyl]-minocycline or salt thereof about 12 hours after the first oral dose.

21. The method of claim 19, comprising administering to said subject one oral dose of 450 mg of 9-[(2,2-dimethyl-propyl amino)-methyl]-minocycline or salt thereof once every 24 hours, for a total of 4 or 5 days.

22. The method of claim 19, comprising administering to said subject one oral dose of 450 mg of 9-[(2,2-dimethyl-propyl amino)-methyl]-minocycline or salt thereof once every 24 hours, for a total of 5 days, and further comprising administering to said subject an additional oral dose of 450 mg of 9-[(2,2-dimethyl-propyl amino)-methyl]-minocycline or salt thereof about 12 hours after the first oral dose.

* * * * *